US012642859B2

(12) United States Patent
Ramirez et al.

(10) Patent No.: US 12,642,859 B2
(45) Date of Patent: Jun. 2, 2026

(54) MACROPINOCYTOSIS SELECTIVE MONOBODY-DRUG CONJUGATES

(71) Applicant: NEW YORK UNIVERSITY, New York, NY (US)

(72) Inventors: Craig Ramirez, Austin, TX (US); Andrew Hauser, New York, NY (US); Nathan Beals, New York, NY (US); Dafna Bar-Sagi, New York, NY (US); Akiko Koide, New York, NY (US); Shohei Koide, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 610 days.

(21) Appl. No.: 18/251,712

(22) PCT Filed: Nov. 10, 2021

(86) PCT No.: PCT/US2021/058807
§ 371 (c)(1),
(2) Date: May 3, 2023

(87) PCT Pub. No.: WO2022/103856
PCT Pub. Date: May 19, 2022

(65) Prior Publication Data
US 2024/0016944 A1     Jan. 18, 2024

Related U.S. Application Data

(60) Provisional application No. 63/112,039, filed on Nov. 10, 2020.

(51) Int. Cl.
| | |
|---|---|
| *A61K 47/64* | (2017.01) |
| *A61K 38/00* | (2006.01) |
| *A61K 41/00* | (2020.01) |
| *A61K 47/65* | (2017.01) |
| *A61K 49/00* | (2006.01) |
| *A61K 51/08* | (2006.01) |
| *A61P 19/08* | (2006.01) |
| *A61P 25/28* | (2006.01) |
| *C07K 14/52* | (2006.01) |
| *C07K 14/78* | (2006.01) |

(52) U.S. Cl.
CPC ...... *A61K 47/6435* (2017.08); *A61K 41/0057* (2013.01); *A61K 47/65* (2017.08); *A61K 49/0002* (2013.01); *A61K 49/0056* (2013.01); *A61K 51/08* (2013.01); *A61K 51/088* (2013.01)

(58) Field of Classification Search
None
See application file for complete search history.

(56) References Cited

U.S. PATENT DOCUMENTS

| | | | |
|---|---|---|---|
| 6,673,901 | B2 | 1/2004 | Koide |
| 9,512,199 | B2 | 12/2016 | Loew et al. |
| 10,377,815 | B2 | 8/2019 | Chandran et al. |
| 2011/0059076 | A1 | 3/2011 | Mcdonagh et al. |
| 2014/0271467 | A1 | 9/2014 | Hackel et al. |
| 2018/0127485 | A1 | 5/2018 | Hastewell et al. |
| 2018/0244755 | A1 | 8/2018 | Camphausen et al. |
| 2018/0265572 | A1 | 9/2018 | Camphausen et al. |
| 2018/0334491 | A1 | 11/2018 | Schmidt et al. |
| 2020/0325210 | A1 | 10/2020 | Anderson et al. |
| 2024/0025969 | A1 | 1/2024 | Ramirez et al. |

FOREIGN PATENT DOCUMENTS

| | | | |
|---|---|---|---|
| CA | 2710835 | A1 | 7/2009 |
| CN | 104053670 | A | 9/2014 |
| EP | 2141243 | A2 | 1/2010 |
| WO | 2002/004523 | A2 | 1/2002 |
| WO | 2010/096394 | A2 | 8/2010 |
| WO | 2012/016245 | A2 | 2/2012 |
| WO | 2017/053617 | A1 | 3/2017 |
| WO | 2017/053619 | A1 | 3/2017 |
| WO | 2019/165017 | A1 | 8/2019 |
| WO | 2020/028533 | A1 | 2/2020 |

OTHER PUBLICATIONS

Extended Search Report for Europe Application No. 21892741.6, dated Sep. 12, 2024.
Zhu et al., "A Fibronectin Peptide Redirects PDGF-BB/PDGFR Complexes to Macropinocytosis-Like Internalization and Augments PDGF-BB Survival Signals," J. Invest. Dermatol. 134(4):921-929 (2013).
King et al., "The Marburg Virus-Neturalizing Human Monoclonal Antibody MR191 Targets a Conserved Site to Block Virus Receptor Binding," Cell Host & Microbe 23(1): 101-109 (2018).
Notice of Reasons for Rejection issued in Japanese Application No. 2023-527718, dated Oct. 20, 2025.
International Search Report and Written Opinion for corresponding Application No. PCT/US2021/058807 (mailed Mar. 24, 2022).
Wojick et al., "A Potent and Highly Specific FN3 Monobody Inhibitor of the Abl SH2 Domain," Nat. Struct. Mol. Biol. 17(4):519-527 (2010).
International Search Report and Written Opinion for Application No. PCT/US2021/058783 (mailed May 16, 2022).

(Continued)

*Primary Examiner* — Manjunath N Rao
*Assistant Examiner* — Jae W Lee
(74) *Attorney, Agent, or Firm* — Troutman Pepper Locke LLP (Rochester)

(57) ABSTRACT

The present disclosure is directed to pharmaceutical and diagnostic compositions comprising macropinocytosis selective non-binding protein-drug conjugates. These non-binding protein-drug conjugates comprise a non-binding fibronectin type III (FN3) domain coupled to a pharmaceutically active moiety or a diagnostic moiety. The disclosure is also directed to methods of treatment and diagnosis that involve administering the pharmaceutical compositions described herein to a subject in need.

17 Claims, 38 Drawing Sheets

Specification includes a Sequence Listing.

(56) References Cited

OTHER PUBLICATIONS

Leao et al., "Production and Characterization of a Monoclonal Antibody Against Niemann Pick Type C Protein," Hybridoma 25:216-217 (2006).

Yelton et al., Hypotheical Protein AMDU2_EPLC00006G0330 [Thermoplasmatales Archaeon E-plasma], Genbank Accession EQB66773.1, National Center for Biotechnology Information (2013).

Daniloski et al., "Identification of Required Host Factors for SARS-CoV-2 Infection in Human Cells," Cell 184(1):92-105 (2021).

Infante et al., "Purified NPC1 Protein," J. Biol. Chem. 283(2):1052-1063 (2008).

Chandler and Buckle, "Development and Differentiation in Monobodies Based on the Fibronectin Type 3 Domain," Cells 9(3):610 (2020).

Lipovsek et al., "Adnectin-Drug Conjugates for Glypican-3-Specific Delivery of a Cytotoxic Payload to Tumors," Protein Eng. Des. Sel. 31(5):159-171 (2018).

Donnelly et al., "Synthesis and Biologic Evaluation of a Novel 18F-Labeled Adnectin as a PET Radioligand for Imaging PD-L1 Expression," J. Nucl. Med. 59(3):529-535 (2018).

Mahalingam et al., "Evaluation of a Centyrin-Based Near-Infrared Probe for Fluorescence-Guided Surgery of Epidermal Growth Factor Receptor Positive Tumors," Bioconjug. Chem. 28(11):2865-2873 (2017).

Koide et al., "High-Affinity Single-Domain Binding Proteins with a Binary-Code Interface," PNAS 104(16):6632-6637 (2007).

Potts amd Campbell, "Fibronectin Structure and Assembly," Curr. Opin. Cell Biol. 6(5):648-655 (1994).

B cervical cancer cells

A

KPC 1203$^{KRasMut}$

FITC-Dextran    Cy5.5-Monobody    Merge

Control

50uM EIPA mouse PDAC cells

B colorectal cancer cells

C

A

Cy5.5-COOH (MW519)

FN-Cy5.5 (MW10740)

90nm PEGyalted nanoparticle

Overall CDC (classical dendritic cell) Cy5+ Positivity:

tdLN

Brachial LN

Overall pDC (plasmacytoid dendritic cell) Cy5+ Positivity:

tdLN brachial LN

B

*With false coloring for Gd³⁺ MRI signal
*Black region marked is acellular cyst

15min post treatment-2nmol

MACROPINOCYTOSIS SELECTIVE MONOBODY-DRUG CONJUGATES

This application is a national stage application under 35 U.S.C. § 371 of International Application No. PCT/US2021/058807, filed Nov. 10, 2021, which claims priority benefit of U.S. Provisional Patent Application No. 63/112,039, filed Nov. 10, 2020, which is hereby incorporated by reference in its entirety.

This invention was made with government support under R35 CA210263, and R41 CA250616 awarded by the National Institutes of Health. The government has certain rights in the invention.

FIELD

The present disclosure is directed to pharmaceutical and diagnostic compositions comprising macropinocytosis selective non-binding protein-drug conjugates. These non-binding protein-drug conjugates comprise a non-binding fibronectin type III (FN3) domain coupled to a pharmaceutically active moiety or a diagnostic moiety. The disclosure is also directed to methods of treatment and diagnosis that involve administering the pharmaceutical compositions described herein to a subject in need.

The instant application contains a computer readable Sequence Listing which has been submitted electronically in ASCII format ("Sequence Listing ASCII") and is hereby incorporated by reference in its entirety. The Sequence Listing ASCII, created on Nov. 18, 2025, is named 147462_002262_ST25_.txt and is 32,840 bytes in size. No new matter is introduced.

BACKGROUND

It has been known for over 30 years that about one-third of all human cancers arise from mutations in KRas proteins. This includes a high percentage of lung (~25%), pancreatic (~95%), and colon (~45%) cancers. When KRas proteins are mutated, cells grow uncontrollably, evade death signals, and even make cells resistant to a number of available cancer therapies. Although great strides have been made over the past 30 years toward understanding the biology of KRas cancers, current therapies against these cancers remain relatively ineffective. A major obstacle in developing a new drug candidate and gaining FDA approval are the toxicity issues that often arise from off-target effects.

The present disclosure is directed to overcoming this and related limitations in the art.

SUMMARY

A first aspect of the present disclosure is directed to a pharmaceutical composition comprising a non-binding protein-drug conjugate and a pharmaceutically acceptable carrier. The non-binding protein-drug conjugate of the pharmaceutical composition comprises a first portion, an amino acid linker, and a second portion. The first portion of the protein-drug conjugate comprises a non-binding fibronectin type III (FN3) domain, and the second portion of the protein-drug conjugate, which is coupled to the first portion via the amino acid linker, is selected from a pharmaceutically active moiety or a diagnostic moiety.

Another aspect of the present disclosure relates to a method of treating cancer in a subject. This method involves administering to the subject having cancer, a composition comprising a non-binding protein-drug conjugate as described herein in an amount effective to treat the cancer.

Another aspect of the present disclosure relates to a method of imaging a tumor in a subject. This method involves selecting a subject having a tumor and administering to the subject a composition comprising a non-binding protein-drug conjugate as described herein.

Another aspect of the present disclosure relates to a method of modulating a subject's immune response. This method involves administering to a subject having a condition that would benefit from immune system modulation, a composition comprising a non-binding protein-drug conjugate as described herein in an amount effective to modulate the subject's immune response.

Another aspect of the present disclosure relates to a method of treating a neurodegenerative condition in a subject. This method involves administering to the subject having the neurodegenerative condition a non-binding protein-drug conjugate as described herein comprising a pharmaceutically active moiety suitable for treating the neurodegenerative condition.

Another aspect of the present disclosure relates to a method of treating an inflammatory condition in a subject. This method involves administering to the subject having the inflammatory condition a non-binding protein-drug conjugate as described herein comprising a pharmaceutically active moiety suitable for treating the inflammatory condition.

Another aspect of the present disclosure relates to a method of treating a bone condition in a subject. This method involves administering to the subject having the bone condition a non-binding protein-drug conjugate as described herein comprising a pharmaceutically active moiety suitable for treating the bone condition.

Another aspect of the present disclosure relates to a method of treating an infectious disease or condition in a subject. This method involves administering to the subject having the infectious disease a non-binding protein-drug conjugate as described herein comprising a pharmaceutically active moiety suitable for treating the infectious disease.

BRIEF DESCRIPTION OF THE DRAWINGS

FIG. 1A shows a schematic design of the monobody-small molecule conjugate. FIG. 1B is a gel shift assay showing a shift after conjugation of monomethyl auristatin E (MMAE). Conjugation of MMAE was determined to be >95%. FIG. 1C shows a SDS-PAGE gel imaged at 800 nm to confirm conjugation of the Cy5.5 to the monobody. FIG. 1D shows an Ellman's test to observe the percentage of MMAE conjugation to the monobody. Ellman's reagent measures free available thiols within the solution.

FIG. 2A and FIG. 2B show the uptake of the fluorescently-tagged monobody and MP marker in human PDAC MIA PaCa and HeLa or HeLa KRas$^{V12}$ cells. Co-localization of the fluorescently-tagged monobody (green) and MP marker (dextran, red) in. DAPI, blue. Boxed region is enlarged, inset. FIG. 2C shows the flow cytometry analysis of monobody (FN-Cy5.5) in oncogenic Ras (HeLaKRas$^{V12}$ and MIAPaCa-2) cells.

FIG. 3A shows the uptake of the fluorescently-tagged monobody and MP marker in mouse PDAC KPC 1203 cells. Co-localization of the fluorescently-tagged monobody (red) and MP marker (dextran, green) in. DAPI, blue. Boxed region is enlarged, inset. FIG. 3B shows the uptake of the fluorescently-tagged monobody and MP marker in WT Ras and mutant Ras human colorectal cancer cells. Co-localization of the fluorescently-tagged monobody (green) and MP marker (dextran, red) with DAPI, blue.

FIG. 4A tracks cell viability as monitored by the infrared dye Syto60 in HeLa (-KRas) and HeLa KRas$^{V12}$ (+KRas) cells treated with increasing concentrations of FN-MMAE. FIG. 4B shows the wild type Ras cell lines (above dashed line, open circles) and oncogenic Ras cell lines (below dashed line, solid circles) from different tissues were treated with increasing concentrations of FN-MMAE and MMAE. FN-MMAE IC$_{50}$ values were normalized to MMAE values. FIG. 4C shows the wildtype Ras cell line (BxPC3) and oncogenic Ras cell line (MiaPaca-2) were treated with increasing concentrations of FN-SN38.

In FIG. 5A, established (100-150 mm$^3$) subcutaneous MiaPaCa and BxPC3 tumors were treated with, PBS (negative control), 0.2 mg/kg of MMAE alone, or 0.2 mg/kg of FN-MMAE non-binding protein conjugate on Days 0, 7, and 14 (yellow arrows). Tumor growth as assessed by volume was slower in FN-MMAE treated animals compared to MMAE treated alone. n=4 per treatment group. Error bars represent SEM of tumor volume. FIG. 5B shows the H&E of ex vivo organs of MIA PaCa tumor bearing mice showing no apparent toxicity for FN-MMAE while MMAE alone saw visual liver damage.

FIG. 6A shows the ex vivo analysis of kidneys from MIA PaCa tumor bearing mice treated with PBS, MMAE, and FN-MMAE with a number of apoptotic markers (i.e., CC3, HMGB1, and cleaved Parp1). Marker expression in these images indicates that FN-MMAE showed little or no difference as compared to PBS, whereas the free MMAE had substantial increase in non-specific toxicity. The images of FIG. 6B show that MMAE's mode of action is through tubulin destabilization. Tubulin staining was drastically reduced in kidneys of MMAE treated mice, whereas FN-MMAE showed no apparent effect.

FIG. 7A shows that biodistribution was detected using IVIS over a time course of 24 hr in MIA PaCa tumor bearing mice with PBS, Cy5.5-COOH, or FN-Cy5.5 treatment. FIG. 7B shows biopsied tissues were analyzed ex vivo by IVIS imaging at 24 hr timepoint. MIA PaCa2 and BxPC3 xenografts were treated with FN-Cy5.5 and ex vivo imaging was used to observe the KRas selective uptake of FN-Cy5.5 (FIG. 7C). FIG. 7D shows after 6 hr, mice were sacrificed, and essential organs were isolated and imaged ex-vivo by IVIS to analyze tumor uptake and accumulation of the monobody, systemic clearance, and tissues with potential toxicities. FIG. 7E shows tumor sections imaged to depict tumor uptake, retention, and co-localization of Cy5.5 and FN-Cy5.5 with a cancer cell maker (CK8).

FIG. 9A provides schematics of Cy5.5-COOH, FN-Cy5.5, and pegylated nanoparticles with Cy5.5 conjugated to the surface that were administered to orthotopic implanted KPC tumor bearing mice. In FIG. 9B, ex vivo IVIS imaging showed FN-Cy5.5 had a 2-fold preference for PDAC lymph nodes (PLN) compared to bronchial lymph nodes (BLN). FIG. 9C are graphs showing Cy5.5 uptake in dendritic cells (DCs), i.e., classic dendritic cells (top graphs) and plasmacytoid dendritic cells (bottom graphs). As shown, a 2-fold increase in cellular uptake of FN was observed.

In FIGS. 10C-10D, ex vivo images (6 hr) depict tumor uptake, retention, and colocalization with a cancer cell maker (CK8).

FIG. 12A is a schematic showing a chelator (DOTA) alone (left) or conjugated to the lone cysteine at the C-terminus of a linker molecule (right). In FIG. 12B, DOTA-Gd$^{3+}$ and FN-DOTA-Gd$^{3+}$ were injected into KPC orthotopic tumor bearing mice at 2 μmol/kg. Increased signal and longer retention were observed in the tumor for FN-DOTA-Gd$^{3+}$. FIG. 12C shows a FN-DOTA-Gd$^{3+}$ that was injected via tail vein in a 4-month-old autochthonous KPC mouse. MRI imaging of FN-DOTA-Gd$^{3+}$ pre-injection(left) and post-injection (right) at 2 anatomical planes across the ventral to dorsal direction (top and bottom, respectively) are shown. Red arrows point to detection of signal in kidneys; red arrowheads point to possible pancreatic tumor. Outlines in top show Ki, kidney; Pa, pancreas; Sp, spleen, St, stomach.

FIGS. 14A and 14B are images showing co-localization of the fluorescently-tagged monobody (red) and MP marker (dextran, green) in KMS11 WT Ras, L363

Mutant NRAS, and RPMI 8226 Mutant KRas cells. DAPI, blue. FN-Cy5.5 showed increased uptake in mutant Ras cell lines which was abolished with the addition of macropinocytosis inhibitor EIPA and KH7. FIG. 14C shows the uptake of FN-Cy5.5 in mutant KRas RPMI 8226 cells at 37° C. and 4° C.

FIG. 15A shows a western blot and FIG. 15B shows a membrane ruffling assay confirming mutant KRas expression with the treatment of doxycycline. FIG. 15C shows that with the addition of doxycycline, the KMS11 cells displayed uptake of FN-Cy5.5 which wasn't observed in the minus doxycycline. This again highlights the selective uptake of FN-Cy5.5 in mutant Ras cells.

DETAILED DESCRIPTION

Figure 1A:
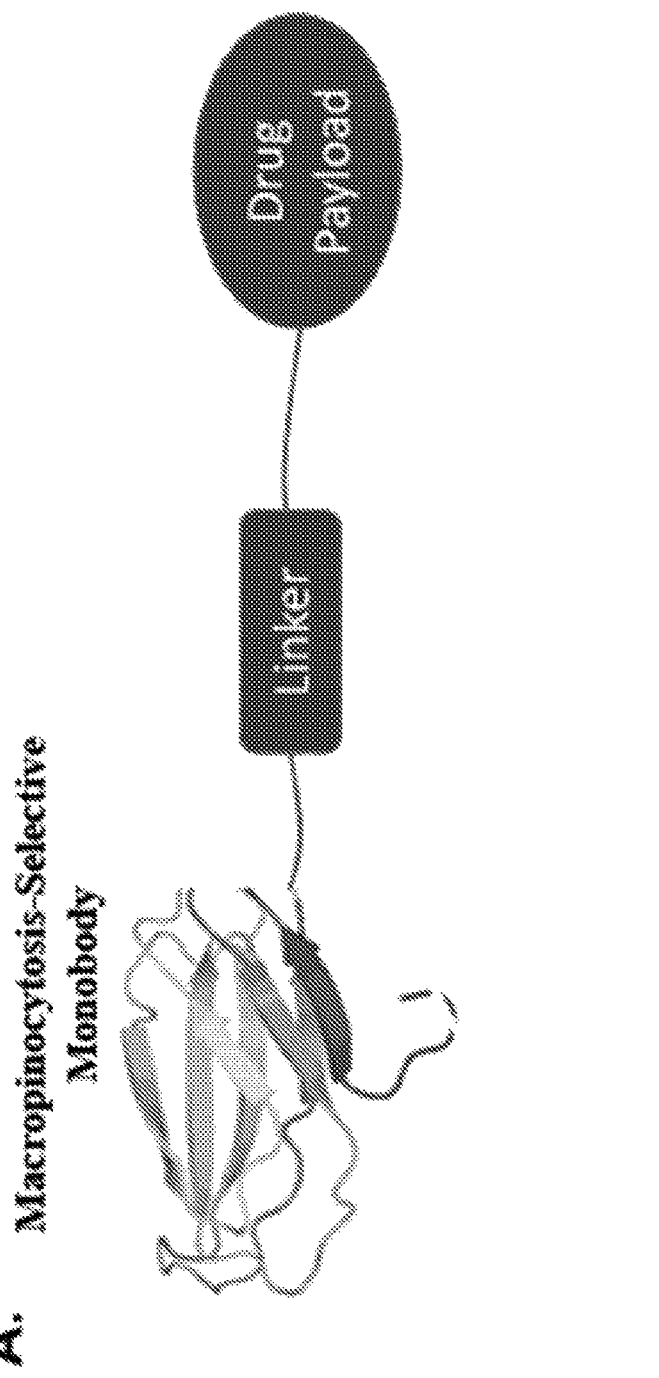
FIGS. 1A-1D show the characterization of MC-small molecule (monobody) conjugation and efficiency.

A first aspect of the present disclosure is directed to a pharmaceutical composition comprising a non-binding protein-drug conjugate and a pharmaceutically acceptable carrier. The non-binding protein-drug conjugate of the pharmaceutical composition comprises a first portion, an amino acid linker, and a second portion. The first portion of the non-binding protein-drug conjugate comprises a non-binding fibronectin type III (FN3) domain, and the second portion of the non-binding protein-drug conjugate, which is coupled to the first portion via the amino acid linker, is selected from a pharmaceutically active moiety or a diagnostic moiety.

The FN3 domain is an evolutionary conserved protein domain that is about 100 amino acids in length and possesses a beta sandwich structure. The beta sandwich structure of human FN3 comprises seven beta-strands, referred to as strands A, B, C, D, E, F, G, with six connecting loops, referred to as loops AB, BC, CD, DE, EF, and FG that exhibit structural homology to immunoglobulin binding domains. Three of the six loops, i.e., loops DE, BC, and FG, correspond topologically to the complementarity determining regions of an antibody, i.e., CDR1, CDR2, and CDR3. The remaining three loops are surface exposed in a manner similar to antibody CDR3. While many naturally occurring FN3 domains and modified FN3 domains contain loop and strand regions that enable binding to a particular target protein or target domain of a protein (i.e., monobodies), the FN3 domain of the protein-drug conjugate of the present disclosure is a non-binding FN3 domain. As used herein, a "non-binding FN3 domain" encompasses naturally occurring and modified FN3 domains that do not bind to or interact with any other protein or protein domain, i.e., the domain lacks an RGD binding domain and any other protein interacting region.

The non-binding FN3 domain of the protein-drug conjugate of the present disclosure can be a FN3 domain derived from any of the wide variety of animal, yeast, plant, and bacterial extracellular proteins containing these domains. In one embodiment, the FN3 domain is a mammalian FN3 domain or a non-binding variant thereof. Exemplary FN3 domains include, for example and without limitation, any one of the FN3 domains present in human tenascin C, or the FN3 domains present in human fibronectin (FN). In some embodiments, the FN3 domain is a non-binding FN3 domain of human fibronectin (UniProtKB Accession No. P02751) selected from an amino acid sequence of SEQ ID NOs: 6-21 as shown in Table 1 or a non-binding variant or derivative thereof. In some embodiments, the FN3 domain of the non-binding protein-drug conjugate is a variant of the $10^{th}$ fibronectin type III domain of human fibronectin (i.e., a variant of SEQ ID NO: 1 or SEQ ID NO: 37). In some embodiments, the FN3 domain of the non-binding protein-drug conjugate is a non-binding FN3 domain of human tenascin (UniProtKB Accession No. P24821) selected from an amino acid sequence of SEQ ID NOs: 22-36 (Table 1) or a variant or derivative thereof. In some embodiments, the FN3 domain of the non-binding protein-drug conjugate is a non-natural synthetic non-binding FN3 domain, such as those described in U.S. Pat. Publ. No. 2010/0216708 to Jacobs et al., which is hereby incorporated by reference in its entirety. Individual FN3 domains are referred to by domain number and protein name, e.g., the $10^{th}$ FN3 domain of fibronectin (10FN3).

TABLE 1

| Exemplary FN3 domains from Human Fibronectin and Tenascin | | |
|---|---|---|
| Domain* | SEQ ID NO | Sequence |
| 1st FN3 of Fibronectin | 6 | GPVEVFITETPSQPNSHPIQWNAPQPSHISKYILRWRPKNSVGRWKEA TIPGHLNSYTIKGLKPGVVYEGQLISIQQYGHQEVTRFDFTTTST |
| 2nd FN3 of Fibronectin | 7 | VATSESVTEITASSFVVSWVSASDTVSGFRVEYELSEEGDEPQYLDLP STATSVNIPDLLPGRKYIVNVYQISEDGEQSLILSTSQTTAPD |
| 3rd FN3 of Fibronectin | 8 | APPDTTVDQVDDTSIVVRWSRPQAPITGYRIVYSPSVEGSSTELNLPE TANSVTLSDLQPGVQYNITIYAVEENQESTPVVIQQETTGTPRS |
| 4th FN3 of Fibronectin | 9 | SPRDLQFVEVTDVKVTIMWTPPESAVTGYRVDVIPVNLPGEHGQRLP ISRNTFAEVTGLSPGVTYYFKVFAVSHGRESKPLTAQQTTKLD |
| 5th FN3 of Fibronectin | 10 | APTNLQFVNETDSTVLVRWTPPRAQITGYRLTVGLTRRGQPRQYNV GPSVSKYPLRNLQPASEYTVSLVAIKGNQESPKATGVFTTLQPG |
| 6th FN3 of Fibronectin | 11 | SSIPPYNTEVTETTIVITWTPAPRIGFKLGVRPSQGGEAPREVTSDSGSI VVSGLTPGVEYVYTIQVLRDGQERDAPIVNKVVTPLS |

TABLE 1-continued

Exemplary FN3 domains from Human Fibronectin and Tenascin

| Domain* | SEQ ID NO | Sequence |
|---|---|---|
| 7th FN3 of Fibronectin | 12 | PPTNLHLEANPDTGVLTVSWERSTTPDITGYRITTTPTNGQQGNSLEE<br>VVHADQSSCTFDNLSPGLEYNVSVYTVKDDKESVPISDTIIPEVPQL |
| EDB domain of Fibronectin | 13 | TDLSFVDITDSSIGLRWTPLNSSTIIGYRITVVAAGEGIPIFEDFVDSSV<br>GYYTVTGLEPGIDYDISVITLINGGESAPTTLTQQTAVP |
| 8th FN3 of Fibronectin | 14 | PPTDLRFTNIGPDTMRVTWAPPPSIDLTNFLVRYSPVKNEEDVAELSI<br>SPSDNAVVLTNLLPGTEYVVSVSSVYEQHESTPLRGRQKTGLDSP |
| 9th FN3 of Fibronectin | 15 | TGIDFSDITANSFTVHWIAPRATITGYRIRHHPEHFSGRPREDRVPHSR<br>NSITLTNLTPGTEYVVSIVALNGREESPLLIGQQSTVSD |
| 10th FN3 of Fibronectin | 37† | VPRDLEVVAATPTSLLISWDAPAVTVRYYRITYGETGGNSPVQEFTV<br>PGSKSTATISGLKPGVDYTITVYAVTGRGDSPASSKPISINYRTEID |
| 11th FN3 of Fibronectin | 16 | KPSQMQVTDVQDNSISVKWLPSSSPVTGYRVTTTPKNGPGPTKTKTA<br>GPDQTEMTIEGLQPTVEYVVSVYAQNPSGESQPLVQTAVTNIDRP |
| EDA domain of Fibronectin | 17 | KGLAFTDVDVDSIKIAWESPQGQVSRYRVTYSSPEDGIHELFPAPDGE<br>EDTAELQGLRPGSEYTVSVVALHDDMESQPLIGTQSTAIP |
| 12th FN3 of Fibronectin | 18 | APTDLKFTQVTPTSLSAQWTPPNVQLTGYRVRVTPKEKTGPMKEINL<br>APDSSSVVVSGLMVATKYEVSVYALKDTLTSRPAQGVVTTLENVSP<br>P |
| 13th FN3 of Fibronectin | 19 | RRARVTDATETTITISWRTKTETITGFQVDAVPANGQTPIQRTIKPDV<br>RSYTITGLQPGTDYKIYLYTLNDNARSSPVVIDASTAID |
| 14th FN3 of Fibronectin | 20 | APSNLRFLATTPNSLLVSWQPPRARITGYIIKYEKPGSPPREVVPRPRP<br>GVTEATITGLEPGTEYTIYVIALKNNQKSEPLIGRKKTDELP |
| 15th FN3 of Fibronectin | 21 | PGLNPNASTGQEALSQTTISWAPFQDTSEYIISCHPVGTDEEPLQFRVP<br>GTSTSATLTGLTRGATYNVIVEALKDQQRHKVREEVVTVGNSVNEG |
| 1st FN3 of Tenascin | 22 | PPKDLVVTEVTEETVNLAWDNEMRVTEYLVVYTPTHEGGLEMQFR<br>VPGDQTSTIIQELEPGVEYFIRVFAILENKKSIPVSARVATYLPAP |
| 2nd FN3 of Tenascin | 23 | EGLKFKSIKETSVEVEWDPLDIAFETWEIIFRNMNKEDEGEITKSLRRP<br>ETSYRQTGLAPGQEYEISLHIVKNNTRGPGLKRVTTTRLD |
| 3rd FN3 of Tenascin | 24 | APSQIEVKDVTDTTALITWFKPLAEIDGIELTYGIKDVPGDRTTIDLTE<br>DENQYSIGNLKPDTEYEVSLISRRGDMSSNPAKETFTTGLD |
| 4th FN3 of Tenascin | 25 | APRNLRRVSQTDNSITLEWRNGKAAIDSYRIKYAPISGGDHAEVDVP<br>KSQQATTKTTLTGLRPGTEYGIGVSAVKEDKESNPATINAATELDTP<br>KD |
| 5th FN3 of Tenascin | 26 | LQVSETAETSLTLLWKTPLAKFDRYRLNYSLPTGQWVGVQLPRNTT<br>SYVLRGLEPGQEYNVLLTAEKGRHKSKPARVKASTEQAP |
| 6th FN3 of Tenascin | 27 | ELENLTVTEVGWDGLRLNWTAADQAYEHFIIQVQEANKVEAARNL<br>TVPGSLRAVDIPGLKAATPYTVSIYGVIQGYRTPVLSAEASTGET |
| 7th FN3 of Tenascin | 28 | NLGEVVVAEVGWDALKLNWTAPEGAYEYFFIQVQEADTVEAAQNL<br>TVPGGLRSTDLPGLKAATHYTITIRGVTQDFSTTPLSVEVLTEEV |
| 8th FN3 of Tenascin | 29 | DMGNLTVTEVSWDALRLNWTTPDGTYDQFTIQVQEADQVEEAHNL<br>TVPGSLRSMEIPGLRAGTPYTVTLHGEVRGHSTRPLAVEVVTEDLPQ<br>L |
| 9th FN3 of Tenascin | 30 | GDLAVSEVGWDGLRLNWTAADNAYEHFVIQVQEVNKVEAAQNLT<br>LPGSLRAVDIPGLEAATPYRVSIYGVIRGYRTPVLSAEASTAKEP |
| 10th FN3 of Tenascin | 31 | EIGNLNVSDITPESFNLSWMATDGIFETFTIEIIDSNRLLETVEYNISGA<br>ERTAHISGLPPSTDFIVYLSGLAPSIRTKTISATATTEALPL |
| 11th FN3 of Tenascin | 32 | ENLTISDINPYGFTVSWMASENAFDSFLVTVVDSGKLLDPQEFTLSGT<br>QRKLELRGLITGIGYEVMVSGFTQGHQTKPLRAEIVTEAEP |
| 12th FN3 of Tenascin | 33 | EVDNLLVSDATPDGFRLSWTADEGVFDNFVLKIRDTKKQSEPLEITL<br>LAPERTRDITGLREATEYEIELYGISKGRRSQTVSAIATTAMG |
| 13th FN3 of Tenascin | 34 | SPKEVIFSDITENSATVSWRAPTAQVESFRITYVPITGGTPSMVTVDGT<br>KTQTRLVKLIPGVEYLVSIIAMKGFEESEPVSGSFTTALDG |

TABLE 1-continued

Exemplary FN3 domains from Human Fibronectin and Tenascin

| Domain* | SEQ ID NO | Sequence |
|---|---|---|
| 14th FN3 of Tenascin | 35 | PSGLVTANITDSEALARWQPAIATVDSYVISYTGEKVPEITRTVSGNT VEYALTDLEPATEYTLRIFAEKGPQKSSTITAKFTTDLD |
| 15 FN3 of Tenascin | 36 | SPRDLTATEVQSETALLTWRPPRASVTGYLLVYESVDGTVKEVIVGP DTTSYSLADLSPSTHYTAKIQALNGPLRSNMIQTIFTTIGLL |

*Domain nomenclature for human fibronectin is the conventional nomenclature as set forth in Potts and Campbell, "Fibronectin Structure and Assembly," Curr. Opin. Cell Biol. 6:648-655 (1994). Domain nomenclature for human tenascin is the nomenclature provided in UniProt Accession No. P24821

In some embodiments, the FN3 domain of the non-binding protein-drug conjugate is a FN3 domain known to have little or no functional binding activity. Suitable non-binding FN3 domains include the $1^{st}$, $2^{nd}$, $3^{th}$, $4^{th}$, $5^{th}$, $6^{th}$, $7^{th}$, $11^{th}$, $12^{th}$, and $13^{th}$ type III fibronectin domains of human fibronectin (SEQ ID NOs: 6-12, 16, 18, and 19) and the EDB and EDA domains of human fibronectin (SEQ ID NOs: 13 and 17). Suitable FN3 domains also encompass non-binding domains having an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% similar to an amino acid sequence of SEQ ID NO: 6-12, 16, 18, or 19.

In some embodiments, a suitable FN3 domain of the non-binding protein-drug conjugate comprises any one of the $1^{st}$, $2^{nd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, and $15^{th}$ type III fibronectin domains of human tenascin (SEQ ID NOs: 22, 23, 25-36). Suitable FN3 domains of the non-binding protein-drug conjugate also encompass non-binding domains having an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% similar to an amino acid sequence of SEQ ID NO: 22, 23, and 25-36.

In some embodiments, the FN3 domain of the non-binding protein-drug conjugate is a non-binding variant of the $8^{th}$, $9^{th}$, $10^{th}$, $14^{th}$ and $15^{th}$ type III fibronectin domains of human fibronectin or a non-binding variant of the $3^{rd}$ type III fibronectin domain of human tenascin. These non-binding variants contain at least one amino acid residue modification in the amino acid sequence of SEQ ID NOs: 1, 14, 15, 20, 21, and 24. Accordingly, suitable FN3 domains include FN3 domains having an amino acid sequence that is 80%, 81%, 82%, 83%, 84%, 85%, 86%, 87%, 88%, 89%, 90%, 91%, 92%, 93%, 94%, 95%, 96%, 97%, 98% or 99% similar in sequence to the amino acid sequence of SEQ ID NO: 1, 14, 15, 20, 21, or 24. Suitable FN3 domains include FN3 domains having an amino acid sequence that is <100% similar in sequence to the amino acid sequence of any one of SEQ ID NO: 1, 14, 15, 20, 21, or 24.

In some embodiments, the FN3 domain of the non-binding protein-drug conjugate is derived from the $10^{th}$ FN domain of fibronectin ($^{10}$FN3). In some embodiments, the FN3 domain of the non-binding protein-drug conjugate is derived from the human $^{10}$FN3 domain. The human $^{10}$FN3 domain has the amino acid sequence of SEQ ID NO: 1 as shown below. The locations of the BC (residues 24-30), CD (residues 40-45), DE (residues 51-55), and FG (residues 75-86) loops are underlined within the wild-type sequence of SEQ ID NO: 1. In accordance with the present disclosure, the non-binding FN3 domain of the non-binding protein-drug conjugate is a non-binding variant of SEQ ID NO: 1, i.e., it comprises one or more amino acid additions, substitutions, or deletions within the amino acid sequence of SEQ ID NO:1.

(SEQ ID NO: 1)
VSDVPRDLEVVAATPTSLLISWDA$_{24}$PAVTVR$_{30}$YYR$_{33}$ITYGETG$_{40}$GNSP
V$_{45}$QEFTVP$_{51}$GSKS$_{55}$TATISGLKPGVDYTITVYAV$_{75}$TGRGDSPASSK$_{86}$
PISINYRT

In accordance with the present disclosure, the non-binding FN3 domain of the protein-drug conjugate of the present disclosure comprises a variant SEQ ID NO: 1 containing at least one modification within the RGD amino acid sequence of the FG loop of the FN3 domain, i.e., amino acid residues 75-86 of SEQ ID NO: 1. Suitable modifications include amino acid residue substitutions, insertions, and/or deletions. In some embodiments, at least one of, at least two of, or at least three of the RGD amino acid residues of the FG loop of the FN3 domain are modified to eliminate RGD mediated binding. In some embodiments, the non-binding FN3 domain of the present disclosure comprises a variant of SEQ ID NO: 1, wherein the arginine (R) at the position corresponding to position 78 of SEQ ID NO: 1 (R78) is substituted or deleted. Suitable amino acid substitutions include, without limitation, substitution with a residue selected from serine (S), alanine (A), glutamic acid (E), glycine (G), lysine (K), asparagine (N), aspartic acid (D), and glutamine (Q). In some embodiments, the amino acid substitution is an arginine to serine substitution at the amino acid residue corresponding to the arginine at position 78 (R78S) of SEQ ID NO: 1. In some embodiments, the non-binding FN3 domain of the present disclosure comprises a variant of SEQ ID NO: 1, wherein the glycine (G) at the position corresponding to position 79 of SEQ ID NO: 1 (G79) is substituted or deleted. Suitable amino acid substitutions include, without limitation, substitution with a residue selected from S, A, E, D, K, N, or Q. In some embodiments, the amino acid substitution is a glycine to serine substitution at the amino acid residue corresponding to the glycine at position 79 (G79S) of SEQ ID NO: 1. In some embodiments, the non-binding FN3 domain of the present disclosure comprises a variant of SEQ ID NO: 1, wherein the aspartic acid (D) at the position corresponding to position 80 of SEQ ID NO: 1 (D80) is substituted or deleted. Suitable amino acid substitutions include, without limitation, substitution with a residue selected from S, A, E, G, K, N, or Q. In some embodiments, the amino acid substitution is an aspartic acid to serine substitution at the amino acid residue corresponding to the aspartic acid at position 80 (D80S) of SEQ ID NO: 1.

In some embodiments, the non-binding FN3 domain of the protein-drug conjugate of the present disclosure comprises one more additional amino acid modifications in the FG loop, i.e., corresponding to amino acid residues 75-86 of SEQ ID NO: 1. Suitable amino acid substitutions include, without limitation, substitution with a residue selected from S, A, E, G, K, N, or Q. In some embodiments, the non-binding FN3 domain of the protein-drug conjugate comprises a variant of SEQ ID NO: 1, wherein the FG loop comprises the amino acid sequence of SSSSSSSS (SEQ ID NO: 4).

In some embodiments, the non-binding FN3 domain of the protein-drug conjugate, further comprises one or more amino acid substitutions in the amino acid sequence of the BC loop, i.e., amino acid residues 24-30 of SEQ ID NO: 1. Suitable amino acid substitutions include, without limitation, substitution with a residue selected from S, A, E, G, K, N, or Q. In some embodiments, the non-binding FN3 domain of the protein-drug conjugate comprises a variant of SEQ ID NO: 1, wherein the BC loop comprises the amino acid sequence of SSSSSVS (SEQ ID NO: 5).

In some embodiments, the non-binding FN3 domain of the protein-drug conjugate comprises an amino acid sequence of SEQ ID NO: 2 as shown below.

(SEQ ID NO: 2)
$VSX_3VPTX_7LEVVAATPTSLLISWDX_{24}X_{25}X_{26}X_{27}X_{28}VX_{30}YYRITYG$
$ETGGNSPVQEFTVPGSKSTATISGLKPGVDYTITVYAX_{75}X_{76}X_{77}X_{78}X_{79}$
$X_{80}X_{81}X_{82}X_{83}SSKPISINYRT$

Wherein, $X_3$ is selected from D, S, A, E, G, K, N, and Q
$X_7$ is selected from D, S, A, E, G, K, N, and Q
$X_{24}$ is selected from S, A, E, G, K, N, D and Q
$X_{25}$ is selected from P, S, A, E, G, K, N, D and Q
$X_{26}$ is selected from A, S, E, G, K, N, D, and Q
$X_{27}$ is selected from V, S, A, E, G, K, N, D, and Q
$X_{28}$ is selected from T, S, A, E, G, K, N, D, and Q
$X_{30}$ is selected from R, S, A, E, G, K, N, D, and Q
$X_{75}$ is selected from V, S, A, E, G, K, N, D, and Q
$X_{76}$ is selected from T, S, A, E, G, K, N, D, and Q
$X_{77}$ is selected from G, S, A, E, K, N, D, and Q
$X_{78}$ is selected from R, S, A, E, G, K, N, D, and Q
$X_{79}$ is selected from G, S, A, E, K, N, D, and Q
$X_{80}$ is selected from D, S, A, E, G, K, N, and Q
$X_{81}$ is selected from S, A, E, G, K, N, D, and Q
$X_{82}$ is selected from P, S, A, E, G, K, N, D, and Q
$X_{83}$ is selected from A, S, E, G, K, N, D, and Q With the proviso, that the non-binding FN3 domain does not comprise the amino acid sequence of SEQ ID NO: 1.

In some embodiments, the non-binding FN3 domain of the protein-drug conjugate comprises the amino acid sequence of SEQ ID NO: 3.

(SEQ ID NO: 3)
VSSVPTKLEVVAATPTSLLISWDASSSSVSYYRITYGETGGNSPVQEFT
VPGSKSTATISGLKPGVDYTITVYASSSSSSSSSSSKPISINYRT.

In some embodiments, the first portion of the non-binding protein-drug conjugate comprises two or more non-binding FN3 domains linked together in tandem. In some embodiments, the first portion of the non-binding protein-drug conjugate comprises, two, three, four, five, six, or more non-binding FN3 domains as described herein linked together in tandem.

In some embodiments, the first portion of the non-binding protein-drug conjugate further comprises one or more tag sequences, e.g., a poly-histidine ($His_{6-}$) tag, a glutathione-S-transferase (GST–) tag, biotinylation tag, or maltose-binding protein (MBP–) tag for purification/production purposes, and/or one or more protease cleavage sites. The tags and cleavage sites can be incorporated into the amino or carboxy termini of the non-binding FN3 domain.

The non-binding protein-drug conjugate of the present disclosure further comprises an amino acid linker that couples the first portion of the non-binding protein-drug conjugate to the second portion of the conjugate. In some embodiments, the amino acid linker is a cleavable linker. In some embodiments, the amino acid linker is a non-cleavable linker. Suitable linkers include peptides composed of repetitive modules of one or more of the amino acids, such as glycine and serine or alanine and proline. Exemplary linker peptides include, e.g., $(Gly-Gly)_n$, $(Gly-Ser)_n$, $(Gly_3-Ser)_n$, $(Ala-Pro)_n$ wherein $n$ is an integer from 1-25. The length of the linker may be appropriately adjusted as long as it does not affect the function of the non-binding protein-drug conjugate. The standard 15 amino acid $(Gly_4-Ser)_3$ linker peptide has been well-characterized and has been shown to adopt an unstructured, flexible conformation. In addition, this linker peptide does not interfere with assembly and activity of the domains it connects (Freund et al., "Characterization of the Linker Peptide of the Single-Chain Fv Fragment of an Antibody by NMR Spectroscopy," *FEBS* 320:97 (1993), the disclosure of which is hereby incorporated by reference in its entirety).

Well known chemical coupling methods may be used to attach the first and second portions using a peptide or other linker to produce non-binding protein-drug conjugates. For example, covalent conjugation of the first and second portions can be accomplished via lysine side chains using an activated ester or isothiocyanate, or via cysteine side chains with a maleimide, haloacetyl derivative or activated disulfide. Site specific conjugation of the first and second portions can also be accomplished by incorporating unnatural amino acids, self-labeling tags (e.g., SNAP or DHFR), or a tag that is recognized and modified specifically by another enzyme such as sortase A, lipoic acid ligase, and formylglycine-generating enzyme. In some embodiments, site specific conjugation of the first and second portions is achieved by the introduction of cysteine residue either at the C-terminus of the non-binding FN3 portion or at a specific site as described by Goldberg et al., "Engineering a Targeted Delivery Platform Using Centyrins," *Protein Engineering, Design & Selection* 29(12):563-572 (2016) and U.S. Patent Application Publication No. 20200325210 to Anderson et al., which are hereby incorporated by reference in their entirety.

In some embodiments, the second portion of the non-binding protein-drug conjugate as described herein is a pharmaceutically active moiety. Suitable pharmaceutically active moieties include small molecules, nucleic acid molecules, antibodies, proteins or polypeptide fragments thereof, and a proteolysis targeting chimeras (PROTAC).

In some embodiments, the pharmaceutically active moiety is a cancer therapeutic. Suitable cancer therapeutics include, without limitation, an antimetabolite, an alkaloid, an alkylating agent, an anti-mitotic agent, an antitumor antibiotic, a DNA binding drug, a toxin, an antiproliferative drug, a DNA antagonist, a radionuclide, a thermoablative agent a proteolysis targeting chimera (PROTAC), a nucleic acid inhibitor, and an immune-modulatory agent.

In some embodiments, the cancer therapeutic is an alkaloid. Suitable alkaloids include, without limitation, duocarmycin, docetaxel, etoposide, irinotecan, paclitaxel, teniposide, topotecan, vinblastine, vincristine, vindesine, and analogs and derivatives thereof.

In some embodiments, the cancer therapeutic is an alkylating agent. Suitable alkylating agents include, without limitation, busulfan, improsulfan, piposulfan, benzodepa, carboquone, meturedepa, uredepa, altretamine, triethylenemelamine, triethylenephosphoramide, triethylenethiophosphorarnide, chlorambucil, chloranaphazine, cyclophosphamide, estramustine, ifosfamide, mechlorethamine, mechlorethamine oxide HCl, melphalan, novemebichin, perfosfamide phenesterine, prednimustine, trofosfamide, uracil mustard, carmustine, chlorozotocin, fotemustine, lomustine, nimustine, semustine ranimustine, dacarbazine, mannomustine, mitobronitol, mitolactol, pipobroman, temozolomide, and analogs and derivatives thereof.

In some embodiments, the cancer therapeutic is an antitumor antibiotic. Suitable antitumor antibiotics include, without limitation, aclacinomycin, actinomycin, anthramycin, azaserine, bleomycin, cactinomycin, calicheamicin, carubicin, carzinophilin, cromomycin, dactinomycin, daunorubicin, 6-diazo-5-oxo-1-norleucine, doxorubicin, epirabicin, idarubicin, menogaril, mitomycin, mycophenolic acid, nogalamycine, olivomycin, peplomycin, pirarubicin, plicamycin, porfiromycin, puromycine, pyrrolobenzodiazepine, streptonigrin, streptozocin, tubercidin, zinostatin, zorubicin, and analogs and derivatives thereof.

In some embodiments, the cancer therapeutic is an antimetabolite agent. Suitable antimetabolite agents include, without limitation, SN-38, denopterin, edatrexate, mercaptopurine (6-MP), methotrexate, piritrexim, pteropterin, pentostatin (2'-DCF), tomudex, trimetrexate, cladridine, fludarabine, thiamiprine, ancitabine, azacitidine, 6-azauridine, carmofur, cytarabine, doxifluridine, emitefur, floxuridine, fluorouracil, gemcitabine, tegafur, hydroxyurea, urethane, and analogs and derivatives thereof.

In some embodiments, the cancer therapeutic is an antiproliferative drug. Suitable anti-proliferative drugs include, without limitation, aceglatone, amsacrine, bisantrene, camptothecin, defosfamide, demecolcine, diaziquone, diflomotecan, eflornithine, elliptinium acetate, etoglucid, etopside, fenretinide, gallium nitrate, hydroxyurea, lamellarin D, lonidamine, miltefosine, mitoguazone, mitoxantrone, mopidamol, nitracrine, pentostatin, phenamet, podophillinic acid 2-ethyl-hydrazide, procarbazine, razoxane, sobuzoxane, spirogermanium, teniposide, tenuazonic acid, triaziquone 2,2',2"-trichlorotriethylamine, and analogs and derivatives thereof.

In some embodiments, the cancer therapeutic is an antimitotic agent. Suitable antimitotic agents include, without limitation, auristatin, a maytansinoid, a dolastatin, a tubulysin, a taxane, a epothilone, a vinca alkaloid, and analogs and derivatives thereof. In some embodiments, the antimitotic agent is an auristatin. In some embodiments, the auristatin is monomethyl auristatin E (MMAE).

In some embodiments, the cancer therapeutic is a PROTAC. Suitable PROTACs include, without limitation BET degraders, such as that disclosed by Pillow et al., "Antibody Conjugation of a Chimeric BET Degrader Enables In vivo Activity," *Chem Med Chem* 15(1): 17-25 (2020), which is hereby incorporated by reference in its entirety. Suitable PROTACs also include Ras degraders.

In some embodiments, the pharmaceutically active moiety of the non-binding protein-drug conjugate as described herein is an immunomodulatory agent. In some embodiments, the immunomodulatory agent is an agent that modifies the phenotype of one or more types of immune cells, e.g., type-1 macrophages, type-2 macrophages, dendritic cells, neutrophils, B cells, and T cells. For example, in some embodiments, the immunomodulatory agent is an agent that modifies the phenotype of an immune cell to result in immune cell activation. In some embodiments, the immunomodulatory agent is an agent that modifies the phenotype of an immune cell to result in immune cell suppression.

In some embodiments, the immunomodulatory agent is a macrophage type-1 stimulating agent. Suitable macrophage type-I stimulating agents include, without limitation, paclitaxel, a colony stimulating factor-1 (CSF-1) receptor antagonist, an IL-10 receptor antagonist, a Toll-like receptor (TLR)-2 agonist, a TLR-3 agonist, a TLR-4 agonist, a TLR-7 agonist, a TLR-8 agonist, and a TLR-9 agonist.

In some embodiments, the macrophage type-1 stimulating agent is a CSF-1 receptor antagonist. Suitable CSF-1 receptor antagonists include, without limitation ABT-869 (Guo et al., "Inhibition of Phosphorylation of the Colony-Stimulating Factor-1 Receptor (c-Fms) Tyrosine Kinase in Transfected Cells by ABT-869 and Other Tyrosine Kinase Inhibitors," *Mol. Cancer. Ther.* 5(4):1007-1012 (2006), which is hereby incorporated by reference in its entirety), imatinib (Guo et al., "Inhibition of Phosphorylation of the Colony-Stimulating Factor-I Receptor (c-Fms) Tyrosine Kinase in Transfected Cells by ABT-869 and Other Tyrosine Kinase Inhibitors," *Mol. Cancer. Ther.* 5(4):1007-1012 (2006), which is hereby incorporated by reference in its entirety), PLX3397 (Mok et al., "Inhibition of CSF1 Receptor Improves the Anti-tumor Efficacy of Adoptive Cell Transfer Immunotherapy," *Cancer Res.* 74(1):153-161 (2014), which is hereby incorporated by reference in its entirety), PLX5622 (Dagher et al., "Colony-stimulating Factor 1 Receptor Inhibition Prevents Microglial Plaque Association and Improves Cognition in 3×Tg-AD Mice," *J. Neuroinflamm.* 12:139 (2015), which is hereby incorporated by reference in its entirety), DCC-3014 (Deciphera Pharmaceuticals), BLZ945 (Krauser et al., "Phenotypic and Metabolic Investigation of a CSF-1R Kinase Receptor Inhibitor (BLZ945) and its Pharmacologically Active Metabolite," *Xenobiotica* 45(2): 107-123 (2015), which is hereby incorporated by reference in its entirety), and GW2580 (Olmos-Alonso et al., "Pharmacological Targeting of CSF1R Inhibits Microglial Proliferation and Prevents the Progression of Alzheimer's-like Pathology," *Brain* 139:891-907 (2016), which is hereby incorporated by reference in its entirety.

In some embodiments, the macrophage type-1 stimulating agent is an IL-10 receptor antagonist. Suitable IL-10 receptor antagonists include, without limitation peptide antagonists as described in Naiyer et al., "Identification and Characterization of a Human L-10 Receptor Antagonist," *Hum. Immunol.* 74(1):28-31 (2013), which is hereby incorporated by reference in its entirety, and IL-10 receptor antagonistic antibodies as described in U.S. Pat. No. 7,553,932 to Von Herrath et al., which is hereby incorporated by reference in its entirety.

In some embodiments, the macrophage type-1 stimulating agent is a TLR agonist, i.e., a TLR2, TLR3, TLR4, TLR7, TLR8, or TLR9 agonist. Suitable TLR-2 agonists for use in the methods described herein include Pam3CSK4, a synthetic triacylated lipoprotein, and lipoteichoic acid (LTA) (Brandt et al., "TLR2 Ligands Induce NF-κB Activation from Endosomal Compartments of Human Monocytes" *PLoS One* 8(12):e80743, which is hereby incorporated by reference in its entirety). A suitable TLR-3 agonist includes, without limitation, polyinosinic:polycytidylic acid (poly I:C) (Smole et al., "Delivery System for the Enhanced Efficiency of Immunostimulatory Nucleic Acids," *Innate Immun.* 19(1):53-65 (2013), which is hereby incorporated by reference in its entirety). Suitable TLR-4 agonists include, without limitation, MPL (Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety), Glucopyranosyl Lipid-A (Matzner et al., "Perioperative treatment with the new synthetic TLR-4 agonist GLA-SE reduces cancer metastasis without adverse effects," *Int. J. Cancer* 138(7):1754-64 (2016), which is hereby incorporated by reference in its entirety), and Immunomax® (Ghochikyan et al., "Targeting TLR-4 with a novel pharmaceutical grade plant derived agonist, Immunomax®, as a therapeutic strategy for metastatic breast cancer," *J. Trans. Med.* 12:322 (2014), which is hereby incorporated by reference in its entirety)

Suitable TLR-7 agonists include, without limitation, uridine/guanidine-rich single-stranded RNA (Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety), 852A (Dudek et al., "First in Human Phase I Trial of 852A, a Novel Systemic Toll-like Receptor 7 Agonist, to Activate Innate Immune Responses in Patients With Advanced Cancer," *Clin. Cancer Res.* 13(23):7119-7125 (2007), which is hereby incorporated by reference in its entirety), resiquimod (Chang et al., "Topical resiquimod Promotes Priming of CTL to Parenteral Antigens," *Vaccine* 27(42):5791-5799 (2009), which is hereby incorporated by reference in its entirety), imidazoquinolines (Itoh et al., "The Clathrin-mediated Endocytic Pathway Participates in dsRNA-induced IFN-beta Production," *J. Immunol.* 181:5522-9 (2008), which is hereby incorporated by reference in its entirety), ANA975 (Fletcher et al., "Masked oral Prodrugs of Toll-like Receptor 7 Agonists: a New Approach for the Treatment of Infectious Disease," *Curr. Opin. Investig. Drugs* 7(8):702-708 (2006), which is hereby incorporated by reference in its entirety), and imiquimod (Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety).

Suitable TLR-8 agonists include, without limitation, resiquimod (Chang et al., "Topical resiquimod Promotes Priming of CTL to Parenteral Antigens," *Vaccine* 27(42): 5791-5799 (2009), which is hereby incorporated by reference in its entirety), and imidazoquinolines (Itoh et al., "The Clathrin-mediated Endocytic Pathway Participates in dsRNA-induced IFN-beta Production," *J. Immunol.* 181: 5522-9 (2008), which is hereby incorporated by reference in its entirety), Suitable TLR-9 agonists include, without limitation, CpG-ODN (Yao et al., "Late Endosome/Lysosome-localized Rab7b Suppresses TLR-9-initiated Proinflammatory Cytokine and Type I IFN Production in Macrophages," *J. Immunol.* 183:1751-8 (2009), which is hereby incorporated by reference in its entirety). Specific CpG-ODNs suitable for use are described in Engel et al., "The Pharmacokinetics of Toll-like Receptor Agonists and the Impact on the Immune System," *Expert Rev. Clin. Pharmacol.* 4(2):275-289 (2011), which is hereby incorporated by reference in its entirety.

Other agents known in the art to reprogram type-2 macrophages to type-1 macrophages (i.e., macrophage type-1 stimulating agent) include, manganese dioxide nanoparticles (see e.g., Song et al., "Bioconjugated Manganese Dioxide Nanoparticles Enhance Chemotherapy Response by Priming Tumor-Associated Macrophages toward M1-like Phenotype and Attenuating Tumor Hypoxia" *ACS Nano.* 10:633-647 (2016), which is hereby incorporated by reference in its entirety), ferumoxytal nanoparticles (Zanganeh, et al. "Iron oxide nanoparticles inhibit tumour growth by inducing pro-inflammatory macrophage polarization in tumour tissues," *Nat. Nanotechnol.* 11:986-994 (2016), which is hereby incorporated by reference in its entirety), mannosylated nanoparticles encapsulating siRNA against IκBα (Ortega et al. "Manipulating the NF-kappaB pathway in macrophages using mannosylated, siRNA-delivering nanoparticles can induce immunostimulatory and tumor cytotoxic functions," *Int. J. Nanomed.* 2163-2177 (2016), which is hereby incorporated by reference in its entirety). In accordance with the present disclosure, these agents can be coupled to a non-binding FN3 domain described herein to form a non-binding protein-drug conjugate.

In some embodiments, the immunomodulatory agent is a macrophage type-2 stimulating agent. Suitable macrophage type-2 stimulating agents include, without limitation, IL-33, IL-4 receptor agonists, glucocorticoids, IL-10 receptor agonists, and IL-1 receptor agonists.

Suitable IL-4 receptor agonists include, without limitation, mutant IL-4 proteins. Exemplary mutant IL-4 proteins include, but are not limited to those described in U.S. Pat. No. 5,723,118 to Sebald, which is hereby incorporated by reference in its entirety.

Glucocorticoids are a class of corticosteroids, which are well known in the art and suitable for inducing a macrophage type-2 phenotype. Exemplary glucocorticoids for incorporation into the non-binding protein-drug conjugate of the present disclosure include, without limitation, cortisol, cortisone, prednisone, prednisolone, methylprednisolone, dexamethasone, betamethasone, triamcinolone, beclomethasone, fludrocortisone, deoxycorticosterone, and aldosterone.

IL-10 receptor agonists are also capable of inducing a macrophage type-2 phenotype in accordance with the conjugates and methods described herein. Suitable IL-10 receptor agonists include, without limitation, mutant IL-10 proteins as described in U.S. Pat. No. 7,749,490 to Sommer et al., which is hereby incorporated by reference in its entirety.

IL-1 receptor agonists are also capable of inducing a macrophage type-2 phenotype and, therefore, can be incorporated as the drug component of the non-binding protein-conjugates described herein. Suitable IL-i receptor agonists include, without limitation, IL-1α, IL-1β, IL-18, IL-33, IL-36α, IL-36β, and IL-36γ (Palomo et al., "The Interleukin (IL)-1 Cytokine Family-Balance Between Agonists and Antagonists in Inflammatory Diseases," Cytokine 76(1):25-37 (2015), which is hereby incorporated by reference in its entirety).

In some embodiments, the immunomodulatory agent is a macrophage type-2 depleting agent. Suitable macrophage depleting agents include, without limitation clodronate, zoledronic acid, alendronate, and trabectedin.

In some embodiments, the immunomodulatory agent is a T cell stimulating agent. Suitable T cell stimulating agents include, without limitation stimulator of interferon genes (STING) agonists. STING agonists include, without limitation, cyclic dinucleotides (CDNs), such as cyclic dimeric guanosine monophosphate (c-di-GMP), cyclic dimeric adenosine monophosphate (c-di-AMP), cyclic GMP-AMP (cGAMP), and dithio-(R$_P$,R$_p$)-[cyclic[A(2',5')pA(3',5')p (ADU-S100, Aduro Biotech) and small molecules, such as 5,6-dimethylxanthenone-4-acetic acid (DMXAA) and linked amidobenzimidazole. Other STING agonists under development that are also suitable immunomodulatory agents in accordance with the present disclosure include BMS-986301, E7766, GSK3745417, MK-1454, MK-2118, and SB11285.

In some embodiments, the immunomodulatory agent is a dendritic cell stimulating agent. Suitable dendritic cell stimulating agents for inclusion in the non-binding protein-drug conjugate as described herein include, without limitation, CpG oligonucleotide, imiquimod, topoisomerase I inhibitors (e.g., camptothecin and derivatives thereof), microtubule depolymerizing drugs (e.g., colchicine, podophyllotoxin, and derivatives thereof).

In some embodiments, the immunomodulatory agent is a neutrophil stimulating agent. Suitable neutrophil stimulating agents include, without limitation, recombinant granulocyte colony stimulating factor protein (filgrastim) or a pegylated recombinant granulocyte colony stimulating factor protein.

In some embodiments, the pharmaceutically active moiety of the non-binding protein-drug conjugate of the present disclosure is an oligonucleotide. Suitable oligonucleotides include, without limitation, an siRNA, an aptamer, an miRNA, an immunostimulatory oligonucleotide, a splice-switching oligonucleotide, and guide RNA.

In some embodiments, the pharmaceutically active moiety of the non-binding protein-drug conjugate of the present disclosure is a wound healing agent. Suitable wound healing agents in accordance with this aspect of the disclosure include, without limitation, an agent that stimulates a proinflammatory phenotype of an immune cell. In some embodiments, the pharmaceutically active moiety for the treatment of wound healing is a macrophage type-I stimulating agent as described supra.

In some embodiments, the pharmaceutically active moiety of the non-binding protein-drug conjugate of the present disclosure is a therapeutic moiety suitable for treating a neurodegenerative disease. Exemplary neurodegenerative diseases include, without limitation, amyotrophic lateral sclerosis, Parkinson's disease, Huntington's disease, Alzheimer's disease, and analogs and derivatives thereof.

In any embodiment, the pharmaceutically active moiety of the non-binding protein-drug conjugate is an ALS therapeutic suitable for treating ALS in a subject. Suitable ALS therapeutics include, without limitation, glutamate blockers (e.g. Riluzole, Rilutek, and other derivatives), Endaravone, Radicava, muscle relaxants (e.g. Baclofen, Tizanidine, and other derivatives), and analogs and derivatives thereof.

In any embodiment, the pharmaceutically active moiety of the non-binding protein-drug conjugate is a Parkinson's disease therapeutic to treat Parkinson's disease in a subject. Suitable therapeutics to treat Parkinson's disease include, without limitation, dopamine promoters (e.g., Carbidopa, Levodopa, Carbidopa-levodopa, Entacapone, Cabergoline, Tolcapone, Bromocriptine, Amantadine, and other derivatives), dopamine agonists (e.g. pramipexole, Mirapex, ropinirole, Requip, rotigotine, Neupro, apomorphine, Apokyn), cognition-enhancing medication (Rivastigmine, and other derivatives), anti-tremor drugs (e.g. Benzotropine, and other derivatives), MAO B inhibitors (selegiline, Zelapar, rasagiline, Azilect, safinamide, Xadago, and other derivatives), catechol O-methyl transferase (COMT) inhibitors (e.g. entacapone, Comtan, opicapone, Ongentys, tolcapone, Tasmar, anticholinergics (e.g. benzotropine, Cogentin, trihexyphenidyl, and other derivatives), and analogs and combinations thereof.

In any embodiment, the pharmaceutically active moiety of the non-binding protein-drug conjugate is a Huntington's disease therapeutic to treat Huntington's disease in a subject. Suitable therapeutics to treat symptoms of Huntington's disease include, without limitation, movement controlling drugs (e.g. tetrabenazine, Xenazine, deutetrabenazine, Austedo, and other derivatives) antipsychotic drugs (e.g. haloperidol, Haldol, fluphenazine, risperidone, Risperdal, olanzapine, Zyprexa, quetiapine, Seroquel, and other derivatives), chorea suppressants (e.g. amantadine, Gocovri ER, Osmolex ER, levetiracetam, Keppra, Elepsia XR, Spritam, clonazepam, Klonopin, and other derivatives), and analogs and derivatives thereof.

In any embodiment, the pharmaceutically active moiety of the non-binding protein-drug conjugate is an Alzheimer's disease therapeutic to treat Alzheimer's disease in a subject. Suitable therapeutics to treat Alzheimer's disease include, without limitation, cognition-enhancing medication (e.g. memantine, Namenda, and other derivatives), cholinesterase inhibitors (e.g. donepezil, Aricept, galantamine, Razadyne, rivastigmine, Exelon, and other derivatives), aducanumab, Aduhelm, and analogs and derivatives thereof.

In some embodiments, the pharmaceutically active moiety of the non-binding protein-drug conjugate of the present disclosure is a therapeutic moiety suitable for treating an inflammatory condition. Exemplary inflammatory conditions that can be treated utilizing this non-binding protein-drug conjugate include, without limitation, rheumatoid arthritis, atherosclerosis, macular degeneration, osteoporosis, immune inflammation, non-immune inflammation, renal inflammation, tuberculosis, multiple sclerosis, arthritis, chronic obstructive pulmonary disease (COPD), and Alzheimer's disease, In any embodiment, the pharmaceutically active moiety of the non-binding protein-drug conjugate is a nonsteroidal anti-inflammatory drug (NSAID) (e.g. ibuprofen, Advil, Motrin IB, naproxen sodium, Aleve, and other derivatives), a corticosteroid medication (e.g. prednisone and other derivatives), a conventional disease-modifying antirheumatic drug (DMARDs) (e.g. methotrexate, Trexall, Otrexup, leflunomide, Arava, hydroxychloroquine, Plaquenil, sulfasalazine Azulfidine, and other derivatives), a biologic DMARD (abatacept, Orencia, adalimumab, Humira, anakinra, Kineret, certolizumab, Cimzia, etanercept, Enbrel, golimumab, Simponi, infliximab, Remicade, rituximab, Rituxan, sarilumab, Kevzara, tocilizumab, Actemra, and other derivatives), a targeted synthetic DMARD (e.g.baricitinib, Olumiant, tofacitinib, Xeljanz, upadacitinib, Rinvoq, and other derivatives), and analogs and derivatives thereof.

In any embodiment, the pharmaceutically active moiety of the non-binding protein-drug conjugate is an anti-inflammatory therapeutic selected from statins (e.g. Atorvastatin, Lovastatin, Simvastatin, Pravastatin, and other derivatives) and other cholesterol medications (e.g. exetimibe, Zetia, Fenofibrate, Gemfibrozil, and other derivatives), anticoagulants (e.g. aspirin and other derivatives), blood thinners, and analogs and derivatives thereof.

In any embodiment, the pharmaceutically active moiety of the non-binding protein-drug conjugate is a therapeutic is suitable for treating a bone condition. Suitable bone conditions that can be treated using this non-binding protein-drug conjugate include, for example, osteoporosis and Paget's Bone disease.

In any embodiment, the pharmaceutically active moiety of the non-binding protein-drug conjugate is an osteoporosis therapeutic suitable for treating osteoporosis in a subject. Suitable osteoporosis therapeutics include, without limitation, bisphosphonates (e.g. Alendronate, Binosto, Fosamax, Ibandronate, Boniva, Risedronate, Actonel, Atelvia, Zoledronic acid, Reclast, Zometa, and other derivatives), denosumab (e.g. Prolia, Xgeva, and other derivatives), hormone-related therapy (e.g. estrogen, raloxifene, Evista, testosterone, and other derivatives), bone-building medications (e.g. Teriparatide, Bonsity, Forteo, Abaloparatide, Tymlos, Romosozumab, Evenity, and other derivatives), and analogs and derivatives thereof.

In any embodiment, the pharmaceutically active moiety of the non-binding protein-drug conjugate is a Paget's bone disease therapeutic suitable for treating Paget's bone disease a subject. Suitable therapeutics for Paget's Bone disease include, without limitation, bisphosphonates (e.g. Zoledronic acid, Reclast, Zometa, Pamidronate, Aredia, Ibandronate, Boniva, and other derivatives), and oral bisphosphonates (e.g. Alendronate, Binosto, Risedronate, Actonel, Atelvia, and other derivatives), and analogs and derivatives thereof.

In any embodiment, the pharmaceutically active moiety of the non-binding protein-drug conjugate is an anti-viral therapeutic suitable for treating infectious disease in a subject. Suitable anti-viral therapeutics include, without limitation, oseltamivir, zanamivir, peramivir, baloxavir, penciclovir, Abacavir, Acyclovir, Adefovir, Amantadine, Amprenavir, Umifenovir, Atazanavir, Atripla, Baloxavir marboxil, Biktarvy, Boceprevir, Bulevirtide, Cidofovir, Combivir, Daclatasvir, Darunavir, Delavirdine, Descovy, Docosanol, Dolutegravir, Ibacitabine, Idoxuridine, Imiquimod, Imunovir, Letermovir, Lopinavir, Maraviroc, Methisazone, Moroxydine, Nelfinavir, Nitazoxanide, Oseltamivir, Remdesivir, Ribavirin, Rimantadine, Ritonavir, Saquinavir, Sofosbuvir, Tipranavir, Valaciclovir, Vicriviroc, and Zanamivir, In any embodiments, the subject having the infectious disease has a filovirus. In some embodiments, the filovirus is ebola virus or Marburg virus. Ebola and other filoviruses attach and enter a host cell via endocytosis. The internalized virus is localized in late endosomes/lysosomes and is cleaved by cysteine proteases. In accordance with this embodiment, the pharmaceutically active moiety of the non-binding protein-drug conjugate is an anti-viral therapeutic suitable for treating filovirus in a subject. Suitable anti-viral therapeutics include, without limitation, remdesivir, mAb 114 (Kugelman et al. "Emergence of Ebola virus escape variants in infected nonhuman primates treated with the MB-003 antibody cocktail," *Cell Rep* 2015; 12: 2111-20, which is hereby incorporated by reference in its entirety), REGN-EB3 (Pascal et al. "Development of clinical-stage human monoclonal antibodies that treat advanced Ebola virus disease in nonhuman primates," *J Infect Dis* 2018; 218 (suppl 5): S612-26, which is hereby incorporated by reference in its entirety), and ZMapp (Qiu et al. "Reversion of advanced Ebola virus disease in nonhuman primates with ZMapp," *Nature* 2014; 514: 47-53, which is hereby incorporated by reference in its entirety)

In some embodiments, the subject having the infectious disease has a coronavirus. In some embodiments, the coronavirus is Severe Acute Respiratory Syndrome Coronavirus-2 (SARS-CoV-2) or Middle East Respiratory Syndrome Coronavirus (MERS-CoV). In accordance with this embodiment, the pharmaceutically active moiety of the non-binding protein-drug conjugate is an anti-viral therapeutic suitable for treating coronavirus in a subject. Suitable anti-viral therapeutics include, without limitation, chloroquine, hydroxychloroquine, ivermectin, remdesivir, baricitinib, and paxlovid.

Accordingly, the NPC1 binding molecules described herein can be administered to a subject that has or is at risk of having a coronavirus infection as a therapeutic means of inhibiting infection, inhibiting the progression of infection, and/or decreasing infection in the subject.

In some embodiments, the second portion of the non-binding protein-drug conjugate of the present disclosure is a diagnostic moiety. Suitable diagnostic moieties are those that facilitate the detection, quantitation, separation, and/or purification of the non-binding protein-drug conjugate. Suitable diagnostic moieties include, without limitation, purification tags (e.g., poly-histidine ($His_{6-}$), glutathione-S-transferase (GST–), maltose-binding protein (MBP–)), fluorescent dyes or tags (e.g., chelates (europium chelates), fluorescein and its derivatives, rhodamine and its derivatives, dansyl, Lissamine, phycoerythrin and Texas Red, an enzymatic tag, a radioisotope or radioactive label (e.g., $^4C$, $^{11}C$, $^{14}N$, $^{35}S$ $^3H$, $^{32}P$, $^{99m}Tc$ $^{111}In$, $^{62/64}Cu$ $^{125}I$, $^{18}F$, $^{67/68}Ga$, $^{90}Y$, $^{177}Lu$ and $^{186/188}Re$), a radionucleotide with chelator (e.g., MAG3, DTPA, and DOTA, see also, Liu S., "Bifunctional Coupling Agents for Radiolabeling of Biomolecules and Target Specific Delivery of Metallic Radionuclides," *Adv. Drug Deli. Ref* 60(12):1347-1370 (2008), which is hereby incorporated by reference in its entirety), a microbubble (Abou-Elkacem et al., "Ultrasound molecular imaging of the breast cancer neovasculature using engineered fibronectin scaffold ligands: A novel class of targeted contrast ultrasound agent," *Theranostics* 6:1740-1752 (2016), which is hereby incorporated by reference in its entirety), a contrast agent suitable for imaging, or a photosensitize.

In some embodiments, the diagnostic moiety is a radiolabel, radionuclide or radioisotope bound to a chelating agent. Particularly useful diagnostic radiolabels, radionuclides, or radioisotopes that can be bound to a chelating agent include, without limitation $^{110}In$, $^mIn$, $^{177}Lu$, $^{18}F$, $^{52}Fe$, $^{62}Cu$, $^{64}Cu$ $^{67}Cu$, $^{67}Ga$, $^{68}Ga$, $^{86}Y$, $^9V$, $^{89}Zr$, $^{94}Tc$, $^{94}Tc$, $^{99m}Tc$, $^{120}I$, $^{123}I$, $^{124}I$, $^{125}I$, $^{131}I$, 154Gd, $^{158}Gd$, $^{32}p$, $^nC$, $^{13}N$, $^{15}O$, $^{186}Re$, $^{188}Re$, $^{51}Mn$, $^{52m}Mn$, $^{55}Co$, $^{72}As$, $^{75}Br$, $^{76}Br$, $^{82m}Rb$, $^{83}Sr$, or other gamma-, beta-, or positron-emitters. The diagnostic radiolabels include a decay energy in the range of 25 to 10,000 keV, more preferably in the range of 25 to 4,000 keV, and even more preferably in the range of 20 to 1,000 keV, and still more preferably in the range of 70 to 700 keV. Total decay energies of useful positron-emitting radionuclides are preferably <2,000 keV, more preferably under 1,000 keV, and most preferably <700 keV.

Chelators such as NOTA (1, 4, 7-triaza-cyclononane-N, N',N"-triacetic acid), DOTA (1, 4, 7, 10-tetraazacyclododecane-1, 4, 7, 10-tetraacetic acid), DTP A (1, 1, 4, 7, 7-Diethylenetriaminepentaacetic acid), TETA (p-bromoacetamido-benzyl-tetraethylaminetetraacetic acid), and Df (desferrioxamine B) are of use with a variety of radiolabels, radionuclides, radioisotopes, metals and radiometals. DOTA-type chelators, where the ligand includes hard base chelating functions such as carboxylate or amine groups, are most effective for chelating hard acid cations. Such metal-chelate complexes can be made very stable by tailoring the ring size to the metal of interest. Also, more than one type of chelator may be conjugated to the targetable construct to bind multiple metal ions, e.g., diagnostic radionuclides and/or therapeutic radionuclides.

Chelators are covalently bound to the non-binding FN3 domain of the conjugate using standard methods of bioconjugation. Amine containing residues (e.g., lysine) in the FN3 domain undergo amide bond formation with a chelator containing an activated ester (e.g., an N-hydroxysuccinimidyl ester). Sulfur containing residues (e.g., cysteine) undergo conjugation with chelators containing an activated ester or maleimide moiety. Alternatively, bioconjugates are formed when activated carboxylate residues of the FN3 domain undergo amide or thoiester formation with amine or thiol groups, respectively, on the chelator. Bifunctional linkers, such as, for example, PEG-maleimide (PEG-Mal), succinimidyl-4-(N-maleimidomethyl)cyclohexane-1-carboxylate (SMCC) or N-succinimidyl 3-(2-pyridylthio)propionate (SPDP) can be alternatively used.

In some embodiments, the non-binding protein-drug conjugate of the present disclosure further comprises a third portion. In some embodiments, the third portion of the protein-drug conjugate of the present disclosure comprises a half-life extending moiety. Exemplary half-life extending moieties include, without limitation, albumin, albumin variants (see e.g., U.S. Pat. No. 8,822,417 to Andersen et al., U.S. Pat. No. 8,314,156 to Desai et al., and U.S. Pat. No. 8,748,380 to Plumridge et al., which are hereby incorporated by reference in their entirety), albumin-binding proteins and/or domains, transferrin and fragments and analogues thereof (see e.g., U.S. Pat. No. 7,176,278 to Prior et al., which are hereby incorporated by reference in their entirety), Fc regions and variant Fc regions (see e.g., U.S. Pat. No. 8,546,543 to Lazar et al., U.S. Patent Publication No. 20150125444 to Tsui, and U.S. Pat. No. 8,722,615 to Seehra et al., which are hereby incorporated by reference in their entirety).

Other half-life extending moieties of the non-binding protein-drug conjugate include, without limitation, polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. A pegyl moiety may for example be added to the first portion, i.e., the non-binding FN3 portion, by adding a cysteine residue to the C-terminus of the molecule and attaching a pegyl group to the cysteine using methods well known in the art.

For therapeutic or diagnostic use, the non-binding protein-drug conjugates as described herein are prepared as pharmaceutical or diagnostic compositions containing an effective amount of the protein-drug conjugate as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of non-binding protein-drug conjugate as described herein in such pharmaceutical formulation can vary widely, i.e., from less than about 0.5%, usually at or at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. REMINGTON: THE SCIENCE AND PRACTICE OF PHARMACY, 21$^{st}$ Edition, Troy, D. B. ed., Lipincott Williams and Wilkins, 2006, Part 5, Pharmaceutical Manufacturing pp 691-1092, see especially pp. 958-989, which is hereby incorporated by reference in its entirety.

The non-binding protein-drug conjugates described herein can be used in non-isolated or isolated form. Furthermore, the non-binding protein-drug conjugates described herein can be used alone or in a mixture comprising at least one other non-binding protein-drug conjugate as described herein. In other words, the non-binding protein-drug conjugates can be used in combination, e.g., as a pharmaceutical composition comprising two or more non-binding protein-drug conjugates. For example, non-binding protein-drug conjugates having different, but complementary activities can be combined in a single therapy to achieve a desired therapeutic effect, but alternatively, non-binding protein-drug conjugates having identical activities can also be combined in a single therapy to achieve a desired therapeutic or diagnostic effect. Optionally, the mixture further comprises at least one other therapeutic agent.

Another aspect of the present disclosure relates to a method of treating cancer in a subject. This method involves administering to the subject having cancer a non-binding protein-drug conjugate as described herein or pharmaceutical composition comprising the non-binding protein-drug conjugate to the subject in an amount effective to treat the cancer.

In accordance with all of the methods described herein a "subject" refers to any animal. In some embodiments, the subject is a mammal. Exemplary mammalian subjects include, without limitation, humans, non-human primates, dogs, cats, rodents (e.g., mouse, rat, guinea pig), horses, cattle and cows, sheep, and pigs. In some embodiments, the subject is a human.

In some embodiments, the subject has a type of cancer that is characterized by cancerous cells having enhanced macropinocytosis relative to their corresponding non-cancerous cells. In some embodiments, the cancer is characterized by cancerous cells having an oncogenic mutation in ras, i.e., an oncogenic mutation in H-ras, N-ras, or K-ras. In some embodiments, the subject has a cancer selected from pancreatic cancer, lung cancer, breast cancer, colon cancer, glioma, solid tumor, melanoma, glioblastoma multiforme, leukemia, renal cell carcinoma, hepatocellular carcinoma, prostate cancer, and myeloma.

In some embodiments the subject has a type of cancer that is or has become resistant to primary cancer therapeutic treatment, e.g., resistant to chemotherapy treatment, prior to administering the non-binding protein-drug conjugate or pharmaceutical composition comprising the same. Administering the non-binding protein-drug conjugate comprising a cancer therapeutic or pharmaceutical composition comprising the same is carried out in an amount effective to directly target and kill cancerous cells. Suitable non-binding protein-drug conjugates comprising a cancer therapeutic, e.g., an antimetabolite, an alkaloid, an alkylating agent, an anti-mitotic agent, an antitumor antibiotic, a DNA binding drug, a microtubule targeting drug, a toxin, an antiproliferative drug, a DNA antagonist, radionuclide, a thermoablative agent or a PROTAC are described supra.

In some embodiments, the subject has a type of cancer that is or has become immune tolerant. Administering the non-binding protein-drug conjugate comprising an immunomodulatory agent or pharmaceutical composition comprising the same is carried out in an amount effective to enhance the antitumor immune response. Suitable non-binding protein-drug conjugates comprising an immunomodulatory agent, e.g., a macrophage type-I stimulating agent, a macrophage type-2 depleting agent, a T cell stimulating agent, a dendritic cell stimulating agent, and/or a neutrophil stimulating agent are described supra.

In some embodiments, the method of treating a subject having cancer further involves administering an additional cancer therapeutic in conjunction with the non-binding protein-drug conjugate, or pharmaceutical composition comprising the same. Suitable cancer therapeutics that can be administered in combination with the non-binding protein-drug conjugates described herein as a combination therapy include, for example and without limitation, chemotherapeutic agents. Suitable chemotherapeutics include, without limitation, alkylating agents (e.g., chlorambucil, cyclophophamide, CCNU, melphalan, procarbazine, thiotepa, BCNU, and busulfan), antimetabolites (e.g., methotraxate, 6-mercaptopurine, and 5-fluorouracil), anthracyclines (daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes (e.g. paclitaxel), and epipodophyllotoxins). In some embodiments, the cancer chemotherapeutic is selected from cyclophosphamide, gemcitabine, vorinostat, temozolomide, bortezomib, carmustine, and paclitaxel.

In accordance with the methods described herein, administration of the non-binding protein-drug conjugates or pharmaceutical composition comprising the same, alone or in combination with one or more additional cancer therapeutics, is carried out by systemic or local administration. Suitable modes of systemic administration of the protein-drug conjugates and/or combination therapeutics disclosed herein include, without limitation, orally, topically, transdermally, parenterally, intradermally, intrapulmonary, intramuscularly, intraperitoneally, intravenously, subcutaneously, or by intranasal instillation, by intracavitary or intravesical instillation, intraocularly, intra-arterially, intralesionally, or by application to mucous membranes. In certain embodiments, the therapeutic agents of the methods described herein are delivered orally. Suitable modes of local administration of the therapeutic agents and/or combinations disclosed herein include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of cancer therapeutic being delivered and the type of cancer to be treated.

A therapeutically effective amount of the non-binding protein-drug conjugate or a pharmaceutical composition comprising the same, alone or in combination with an additional cancer therapeutic, in the methods disclosed herein is an amount that, when administered over a particular time interval, results in achievement of one or more therapeutic benchmarks (e.g., slowing or halting of tumor growth, tumor regression, cessation of symptoms, etc.). The non-binding protein-drug conjugate or a pharmaceutical composition comprising the same for use in the presently disclosed methods may be administered to a subject one time or multiple times. In those embodiments where the therapeutic composition is administered multiple times, it may be administered at a set interval, e.g., daily, every other day, weekly, or monthly. Alternatively, it can be administered at an irregular interval, for example on an as-needed basis based on symptoms, patient health, and the like. For example, a therapeutically effective amount may be administered once a day (q.d.) for one day, at least 2 days, at least 3 days, at least 4 days, at least 5 days, at least 6 days, at least 7 days, at least 10 days, or at least 15 days. Optionally, the status of the cancer or the regression of the cancer is monitored during or after the treatment, for example, by a multiparametric ultrasound (mpUS), multiparametric magnetic resonance imaging (mpMRI), and nuclear imaging (positron emission tomography [PET]) of the subject. The dosage of the non-binding protein-drug conjugate or combination therapy administered to the subject can be increased or decreased depending on the status of the cancer or the regression of the cancer detected.

The skilled artisan can readily determine this amount, on either an individual subject basis (e.g., the amount of a non-binding protein-drug conjugate necessary to achieve a particular therapeutic benchmark in the subject being treated) or a population basis (e.g., the amount of non-binding protein-drug conjugate necessary to achieve a particular therapeutic benchmark in the average subject from a given population). Ideally, the therapeutically effective amount does not exceed the maximum tolerated dosage at which 50% or more of treated subjects experience side effects that prevent further drug administrations.

A therapeutically effective amount may vary for a subject depending on a variety of factors, including variety and extent of the symptoms, sex, age, body weight, or general health of the subject, administration mode and salt or solvate type, variation in susceptibility to the drug, the specific type of the disease, and the like.

Another aspect of the present disclosure is directed to a method of modulating a subject's immune response. This method involves administering to the subject having a condition that would benefit from immune system modulation, a non-binding protein-drug conjugate as described herein in an amount effective to modulate the subject's immune response. In accordance with this aspect of the disclosure, suitable non-binding protein-drug conjugates include those conjugates comprising an immunomodulatory agent as the second portion of the conjugate. Suitable immunomodulatory agents, e.g., type-1 macrophage stimulating agents, type-2 macrophage stimulating agents, T cell stimulating agents, dendritic cell stimulating agents, and neutrophil stimulating agents, are all described supra.

Modulating or modifying a subject's immune response in accordance with this aspect of the disclosure is carried out for the purpose of treating, preventing, or slowing the progression of a disease or condition that is caused or exacerbated, at least in part, by the immune response and/or cells of the immune system, e.g., type-1 macrophages, type-2 macrophages, T cells, B cells, dendritic cells, neutrophils. For example, inflammatory diseases and conditions, including but not limited to macular degeneration, atherosclerosis, osteoporosis, immune inflammation, non-immune inflammation, renal inflammation, tuberculosis, multiple sclerosis, arthritis, chronic obstructive pulmonary disease (COPD), and Alzheimer's disease, involve the undesired actions of type-1 macrophages. Employing the methods of the present invention to induce a macrophage type-2 phenotypic change in the type-1 pro-inflammatory macrophages that are involved in or contributing to these disease processes alleviates one or more symptoms or causes of the disease. Accordingly, in one embodiment, the administering is carried out in vivo or ex vivo to a population of type-1 macrophages in or from a subject having an inflammatory or autoimmune condition, including, but not limited to any of those enumerated above. Administering a type-2 macrophage stimulating agent to a population of type-1 macrophages in this context will induce a type-2 phenotypic change, thereby reducing the undesired actions of the type-1 macrophages associated with the disease.

Modulating or modifying immune cell phenotype is also therapeutically beneficial in context of treating various forms of cancer. Recent studies indicate that tumor-associated macrophages (TAMs) exhibit a macrophage type-2-like phenotype. These type-2 macrophages are important tumor-infiltrating cells and play pivotal roles in tumor growth and metastasis. In most solid tumors, the existence of TAMs is advantageous for tumor growth and metastasis. These TAMs produce interleukin IL-10 and transforming growth factor (TGF) β to suppress general antitumor immune responses. Meanwhile, TAMs promote tumor neo-angiogenesis by the secretion of pro-angiogenic factors and define the invasive microenvironment to facilitate tumor metastasis and dissemination. Therefore, employing the methods of the present disclosure to administer a non-binding protein-drug conjugate comprising a macrophage type-1 stimulating agent to induce a type-1 phenotypic change in the TAMs to enhance anti-tumor immunity will significantly alter the progression of the cancer. Cancers that typically have a type-2 macrophage-related component include, without limitation, pancreatic cancer, breast cancer, and non-small cell lung cancer. Alternatively, or in conjunction with administering a non-binding protein-drug conjugate comprising a macrophage type-1 stimulating agent, a non-binding protein-drug conjugate comprising a T cell stimulating agent, a dendritic cell simulating agent, or a neutrophil stimulating agent can be administered to activate or enhance the anti-tumor immune response.

In some embodiments, the subject in need of immune system modulation is a subject suffering from an interferonopathy. As referred to herein, an interferonopathy is a condition involving the enhanced expression of type I interferons, e.g., IFN-α, IFN-β, and IFN-Ω. Interferonopathies that can be treated in accordance with the present disclosure include, without limitation, Aicardi-Goutieres syndrome, Cree encephalitis, systemic lupus erythematosus, rheumatoid arthritis, Sjögrens syndrome, dermatomyositis, multiple sclerosis, spondyloenchondrodysplasia with immune dysregulation, stimulator of interferon genes (STING)-associated vasculopathy with onset in infancy (SAVI), Japanese autoinflammatory syndrome with lipodystrophy (JASL), ubiquitin-specific peptidase 18 deficiency, chronic atypical neutrophilic dermatitis with lipodystrophy, DNA II deficiency, Singleton-Merten syndrome, and chronic atypical neutrophilic dermatosis with lipodystrophy and elevated temperature (CANDLE). Non-binding protein-drug conjugates according to the present disclosure suitable for treating an interferonopathy comprise the non-binding FN3 domain coupled to a type I interferon antagonist. In some embodiments, the type I interferon antagonist is a type I interferon receptor antagonist, such as a janus kinase (JAK) inhibitor. Suitable JAK inhibitors include, JAK1/JAK2 inhibitors, such as and without limitation baricitinib (CAS No. 1187594-09-7), tofacitinib (CAS No. 477600-75-2), ruxolitinib (941678-49-5), AG490 (Tyrphostin family) (CAS No. 133550-30-8), Lestaurtinib (CEP-701; CAS No. 111358-88-4), WP-1034 (Tyrphostin family; CAS No. 857064-42-7), BMS-911543 (CAS No. 1271022-90-2), Fedratinib (TG101348; CAS No. 936091-26-8), Parcritinib (SB1518; CAS No. 937272-79-2), and Momelotinib (CYT387; CAS No. 1056634-68-4).

In some embodiments, the subject in need of immune system modulation is a subject having a wound or undergoing wound healing. In accordance with this embodiment, the subject having a wound or in need of wound healing is administered a non-binding protein-drug conjugate comprising a macrophage type-1 stimulating agent. Suitable type-1 stimulating agents, e.g., paclitaxel, a colony stimulating factor-1 (CSF-1) receptor antagonist, an IL-10 receptor antagonist, a Toll-like receptor (TLR)-2 agonist, a TLR-3 agonist, a TLR-4 agonist, a TLR-7 agonist, a TLR-8 agonist, and a TLR-9 agonist, are described supra.

In some embodiments, the subject in need of immune system modulation is a subject having an inflammatory condition and the non-binding protein-drug conjugate comprises a macrophage depleting agent. Suitable inflammatory conditions that can be treated with a macrophage depleting agent, e.g., clodronate, zoledronic acid, and trabectedin, include, without limitation, rheumatoid arthritis, obesity and obesity related complications, endometriosis, inflammatory conditions of the lung (e.g., chronic obstructive pulmonary disease and pulmonary tuberculosis).

Another aspect of the present disclosure relates to a method of treating a neurodegenerative condition in a subject. This method involves administering to the subject having the neurodegenerative condition a non-binding protein-drug conjugate as described herein comprising a pharmaceutically active moiety suitable for treating the neurodegenerative condition. Exemplary neurodegenerative diseases (e.g., amyotrophic lateral sclerosis, Parkinson's disease, Huntington's disease, Alzheimer's disease) and non-binding protein-drug conjugates suitable for treating these conditions are disclosed supra.

Another aspect of the present disclosure relates to a method of treating an inflammatory condition in a subject. This method involves administering to the subject having the inflammatory condition a non-binding protein-drug conjugate as described herein comprising a pharmaceutically active moiety suitable for treating the inflammatory condition. Exemplary inflammatory conditions that can be treated in accordance with this method include, without limitation, rheumatoid arthritis, atherosclerosis, macular degeneration, osteoporosis, immune inflammation, non-immune inflammation, renal inflammation, tuberculosis, multiple sclerosis, arthritis, chronic obstructive pulmonary disease (COPD), and Alzheimer's disease. Suitable non-binding protein-drug conjugates comprising pharmaceutically active moieties for treating these conditions are disclosed supra.

Another aspect of the present disclosure relates to a method of treating a bone condition in a subject. This method involves administering to the subject having the bone condition a non-binding protein-drug conjugate as described herein comprising a pharmaceutically active moiety suitable for treating the bone condition. Exemplary bone conditions include, without limitation, osteoporosis and Paget's bone disease, and non-binding protein-drug conjugates suitable for treating these conditions are disclosed supra.

Another aspect of the present disclosure relates to a method of treating an infectious disease or condition in a subject. This method involves administering to the subject having the infectious disease a non-binding protein-drug conjugate as described herein comprising a pharmaceutically active moiety suitable for treating the infectious disease. Exemplary infectious diseases (filoviral infections and coronavirus infections) and non-binding protein-drug conjugates suitable for treating these conditions are disclosed supra.

Another aspect of the present disclosure is directed to a method of imaging a tumor in a subject. This method involves selecting a subject having a tumor and administering to said subject a composition comprising a non-binding protein-drug conjugate. In accordance with this aspect of the disclosure, the second portion of the non-binding protein-drug conjugate comprises a diagnostic moiety. Suitable diagnostic moieties are described supra, e.g., fluorescent dyes, radioisotopes, radionuclides, radioisotopes, microbubbles, a contrast agent suitable for imaging, and a photosensitizer.

In accordance with this aspect of the disclosure, the tumor to be imaged is characterized by cancerous cells having enhanced macropinocytosis relative to their corresponding non-cancerous cells. In some embodiments, the tumor to be imaged is characterized by cancerous cells having an oncogenic mutation in H-ras, N-ras, or K-ras. In some embodiments, the tumor to be imaged is a pancreatic tumor, lung tumor, breast tumor, colon tumor, glioma, solid tumor, melanoma, glioblastoma multiforme, leukemia, renal cell carcinoma, hepatocellular carcinoma, prostate tumor, and myeloma.

Detecting the presence of a tumor in a subject using the diagnostic non-binding protein-drug conjugate of the present disclosure is achieved using in vivo imaging techniques. In vivo imaging involves administering to the subject the non-binding protein-diagnostic moiety conjugate described herein, and detecting the tumor cell macropinocytotic-mediated uptake of the conjugate in vivo.

In accordance with this aspect of the disclosure, diagnostic non-binding protein conjugates are administered by intravenous injection into the body of the subject, or directly into the tumor. The dosage of non-binding protein-diagnostic moiety conjugate should be within the same ranges as for treatment methods. In accordance with this embodiment, the diagnostic moiety conjugated to the non-binding FN3 domain is an imaging agent that facilitates in vivo imaging. Suitable imaging agents are described supra and include, without limitation, single photon emission computed tomography (SPECT) agents, positron emission tomography (PET) agents, magnetic resonance imaging (MRI) agents, nuclear magnetic resonance imaging (NMR) agents, x-ray agents, optical agents (e.g., fluorophores, bioluminescent probes, near infrared dyes, quantum dots), ultrasound agents and neutron capture therapy agents, computer assisted tomography agents, two photon fluorescence microscopy imaging agents, and multi-photon microscopy imaging agents. Exemplary detectable markers include radioisotypes (e.g., $^{18}$F, $^{11}$C, $^{13}$N, $^{64}$Cu, $^{124}$I, $^{76}$Br, $^{82}$Rb, $^{68}$Ga, $^{99m}$Tc, $^{111}$In, $^{201}$Tl or $^{15}$O, which are suitable for PET and/or SPECT use) and ultra-small superparamagnetic particles of iron oxide (USPIO) which are suitable for MRI.

Imaging of a tumor in a subject is performed by detecting the number, size, and/or intensity of detected non-binding protein-diagnostic moiety conjugates in the subject. In some embodiments, the level of detected diagnostic conjugate is compared to a corresponding baseline value. An appropriate baseline value can be the average level of non-binding protein diagnostic conjugate found within cells in a population of undiseased individuals. Alternatively, an appropriate baseline value may be the level of non-binding protein diagnostic conjugate found within cells of the same subject determined at an earlier time.

The diagnostic imaging methods described herein can also be used to monitor a subject's response to therapy. In this embodiment, detection of the non-binding protein diagnostic conjugate in the subject is determined prior to the commencement of treatment. The level of non-binding protein diagnostic conjugate in the subject at this time point is used as a baseline value. At various times during the course of treatment administration and detection of the non-binding protein diagnostic conjugate is repeated, and the measured values thereafter compared with the baseline values. A decrease in values relative to baseline signals a positive response to treatment.

EXAMPLES

The following examples are provided to illustrate embodiments of the present disclosure but are by no means intended to limit its scope

Example 1—Production of Non-Binding Protein Drug Conjugate

Figure 1B:
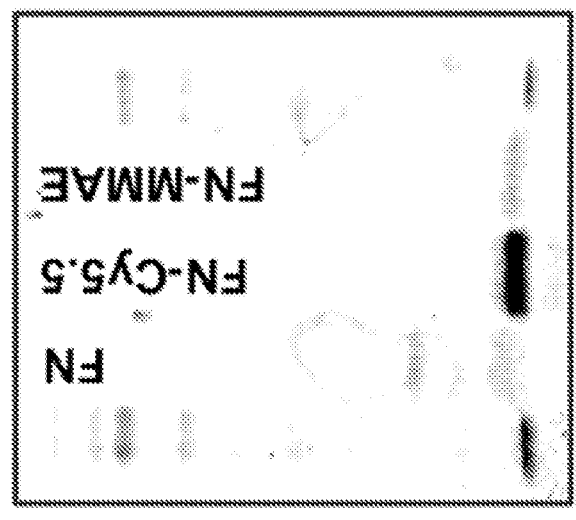
Figure 1C:
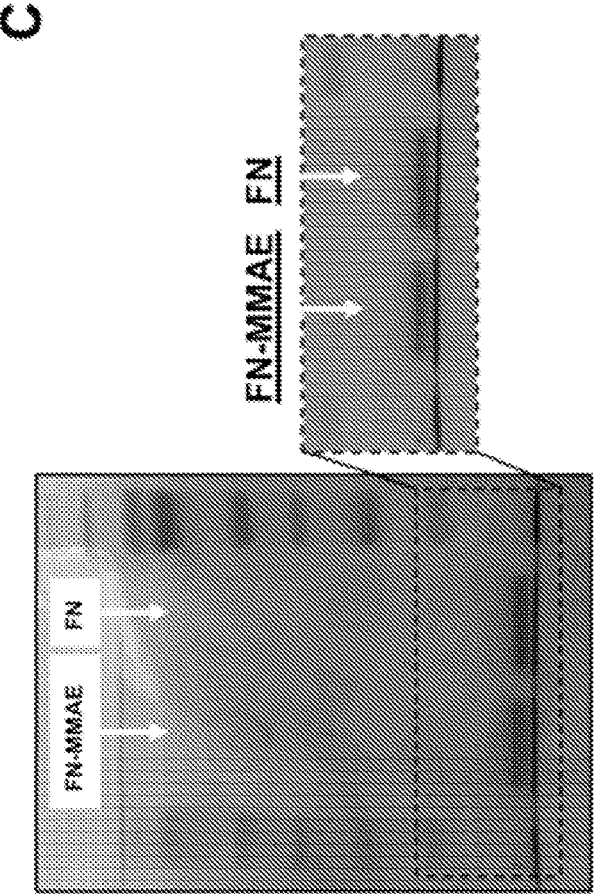
Figure 1D:
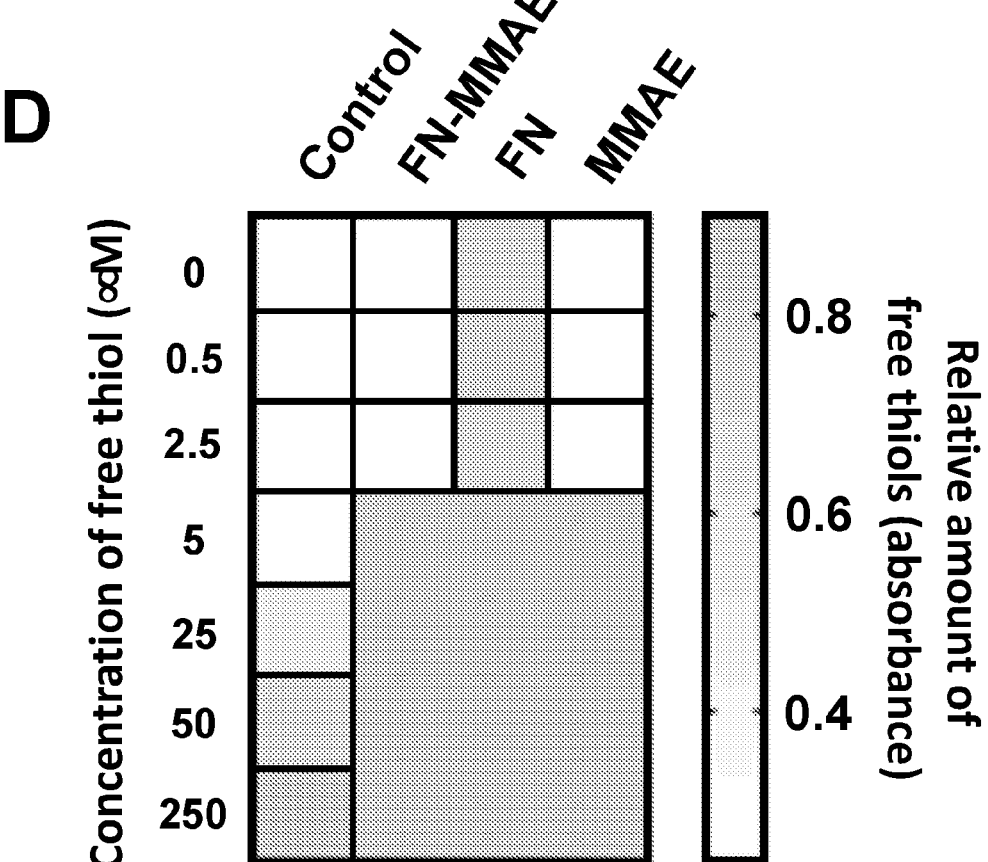

As an initial study, a non-binding FN domain (comprising the amino acid sequence of SEQ ID NO: 3 with the addition of a C-terminal serine and cysteine residues for conjugation) was conjugated to monomethyl auristatin E (MMAE) (see schematic of FIG. 1A). MMAE is a highly toxic agent commonly used in antibody drug conjugates (ADC). The MMAE molecule was attached to the non-binding FN domain with a linker that contains a cathepsin-cleavable linker and a maleimide group for conjugation to the C-terminal free cysteine on the non-binding FN domain protein (FN-MMAE). Maleimide conjugation was performed with a two-step process and 1.5 molar excess of drug. Conjugation was verified by gel shift assay (FIG. 1B), Ellman's test and spectroscopic analysis (FIG. 1D). For in vitro and in vivo imaging, Cy5.5 replaced the drug molecule to monitor pharmacokinetics of the newly designed complex (FIG. 1C).

Example 2—Macropinocytic Uptake of Non-Binding Protein Drug Conjugate

Figure 2A:
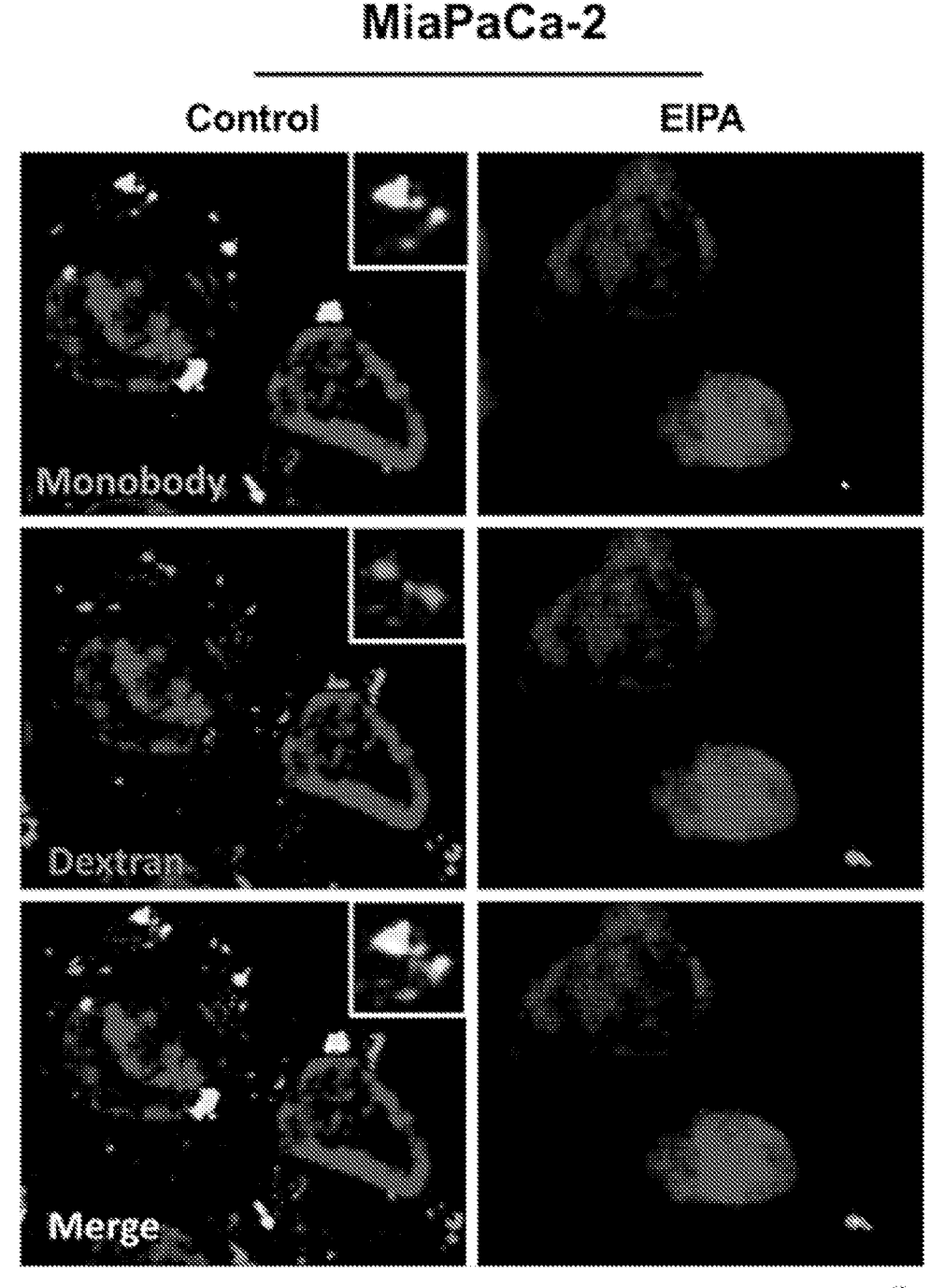
FIGS. 2A-2C show that the cellular uptake of non-binding protein-drug conjugates as disclosed herein is specifically through macropinocytosis (MP).
Figure 2B:
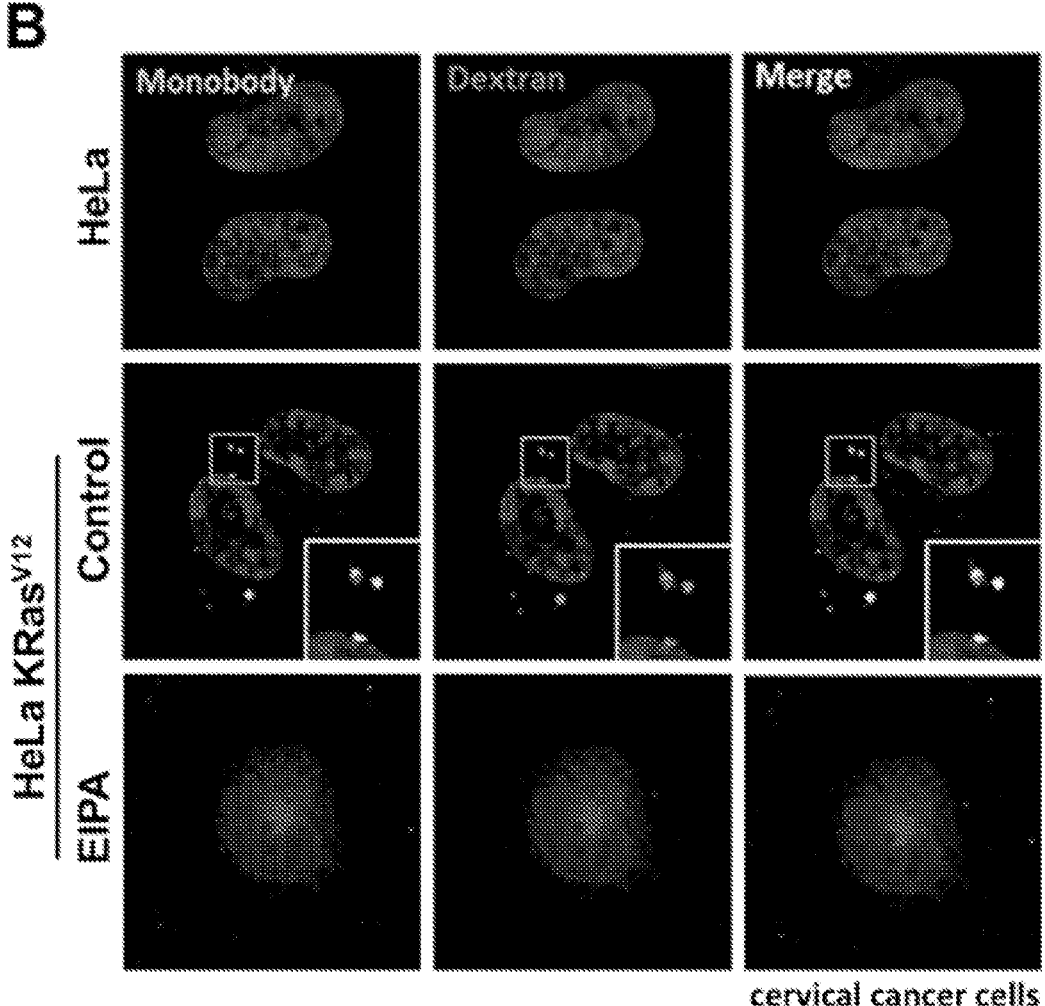
Figure 2C:
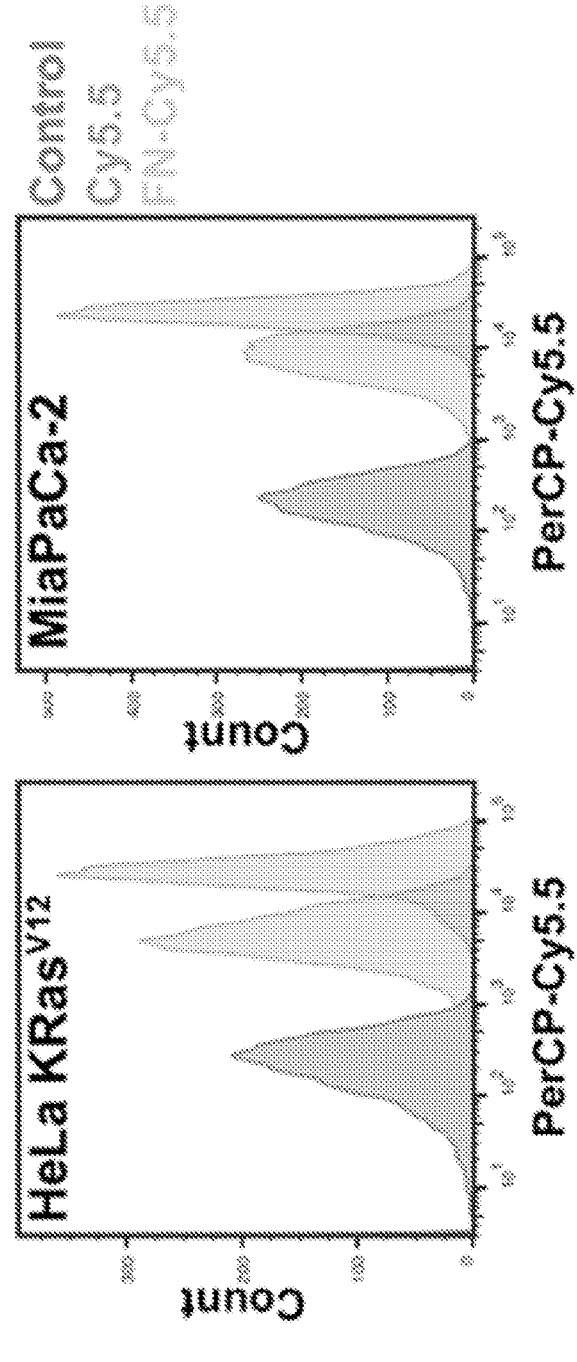
Figure 3A:
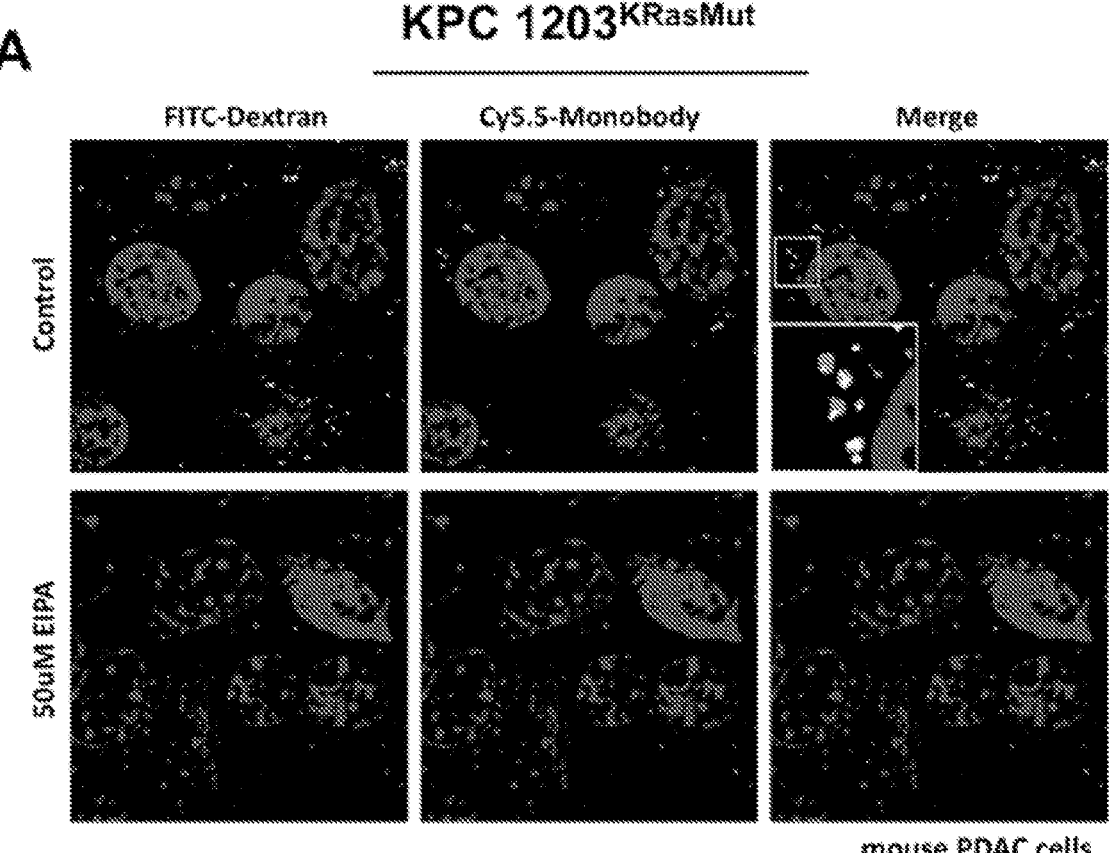
FIGS. 3A-3B show that the cellular uptake of non-binding protein-drug conjugates as disclosed herein is specifically through macropinocytosis (MP).
Figure 3B:
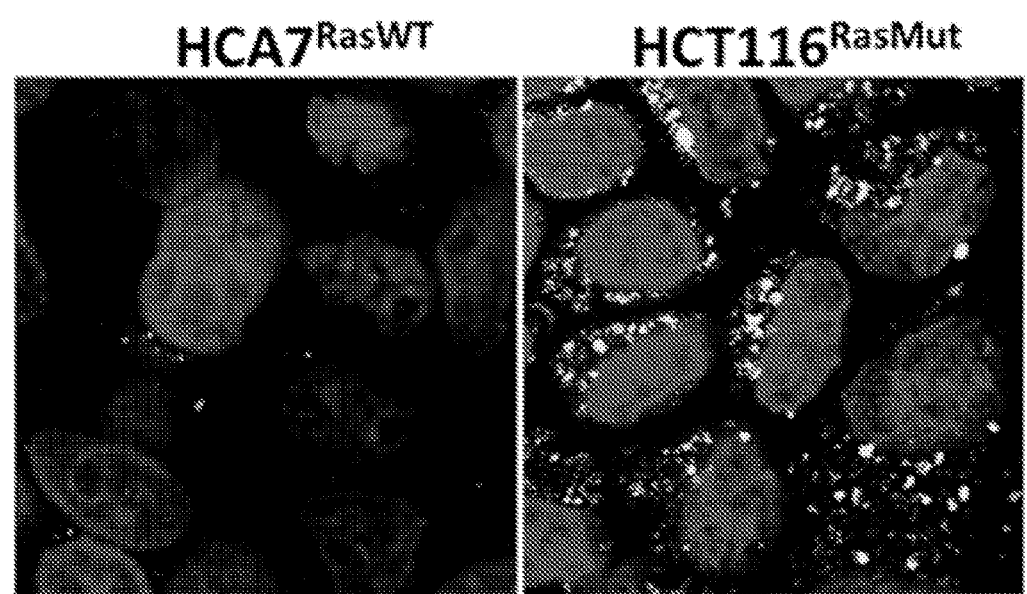

To determine if non-binding FN domains could be internalized, a well-established doxycycline-inducible mutant KRas$^{V12}$ HeLa cell system (hereafter, HeLa KRas$^{V12}$) was used in which macropinocytosis is monitored by high-molecular-weight (70 kDa) tetramethyl-rhodamine labeled (TMR–) dextran. As shown in FIG. 2B, fluorescently labeled non-binding FN domain (FN-Cy5.5) co-localized with TMR-dextran. Importantly, the internalization was dependent on oncogenic Ras, since cells in which doxycycline was not added (HeLa) did not have detectable non-binding FN domain uptake. Further, the macropinocytosis inhibitor, EIPA blocked both non-binding FN domain and dextran uptake into HeLa KRas$^{V12}$ cells (FIG. 2B). Similarly, the mutant KRas PDAC cell line MIA PaCa-2 (human, FIG. 2A) and KPC 1203 (mouse, FIG. 3A) showed co-localization occurring between dextran and FN-Cy5.5; whereas EIPA abolished uptake of both macromolecules (FIGS. 2A and 3A). In FIG. 3B, human colorectal cancer line HCT116 with Ras mutation showed co-localization occurring between dextran and FN-Cy5.5 but no uptake was seen in HCA7 cells with WT Ras. Analysis by flow cytometry of non-binding FN domain treated HeLa KTO+KRas$^{V12}$ and MIA PaCa-2 were positive for FN-Cy5.5 uptake (FIG. 2C).

Figure 14A:
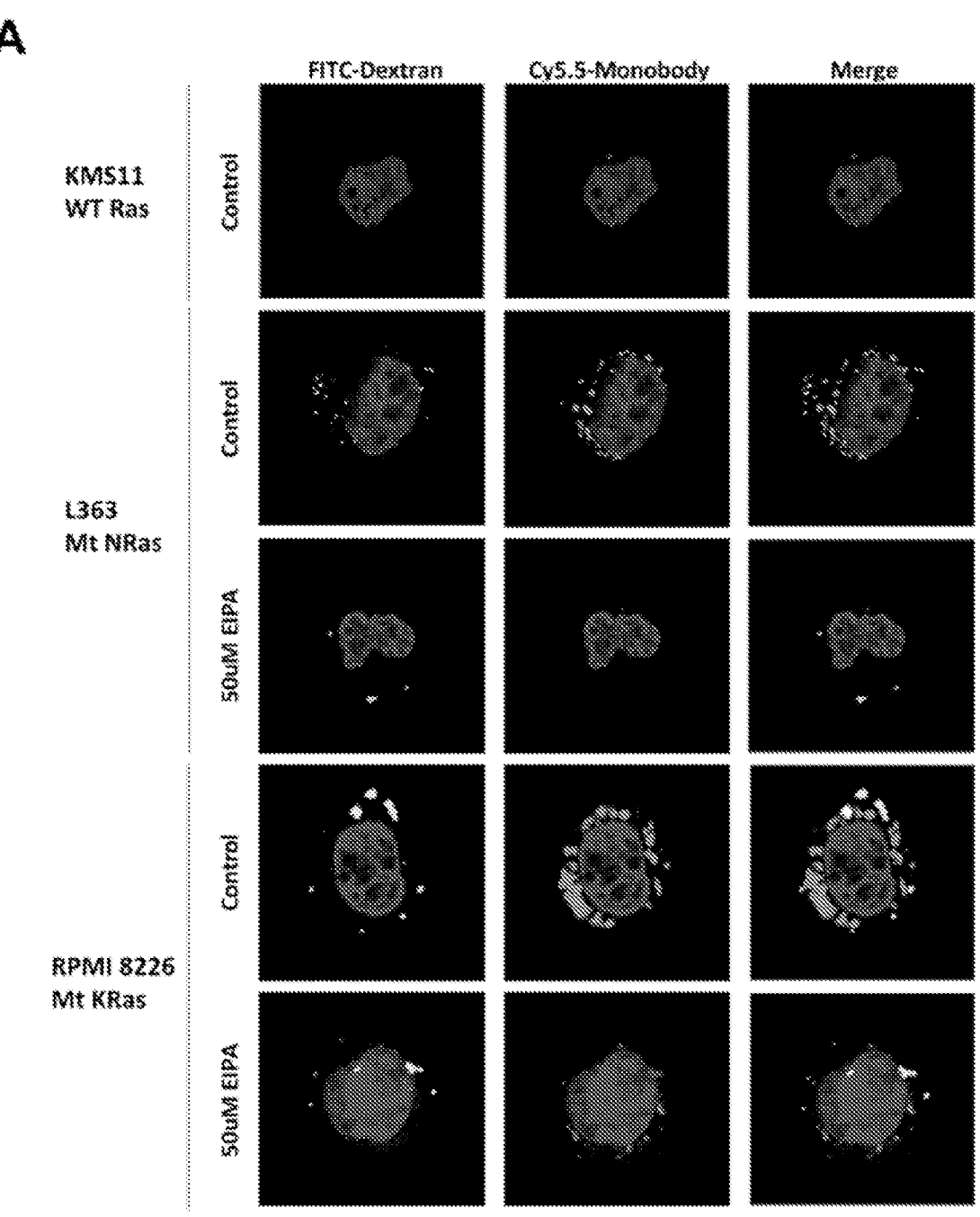
FIGS. 14A-14C show uptake of fluorescently-tagged monobody and MP marker in human multiple myeloma cancer cell lines.
Figures 14B, 14C:
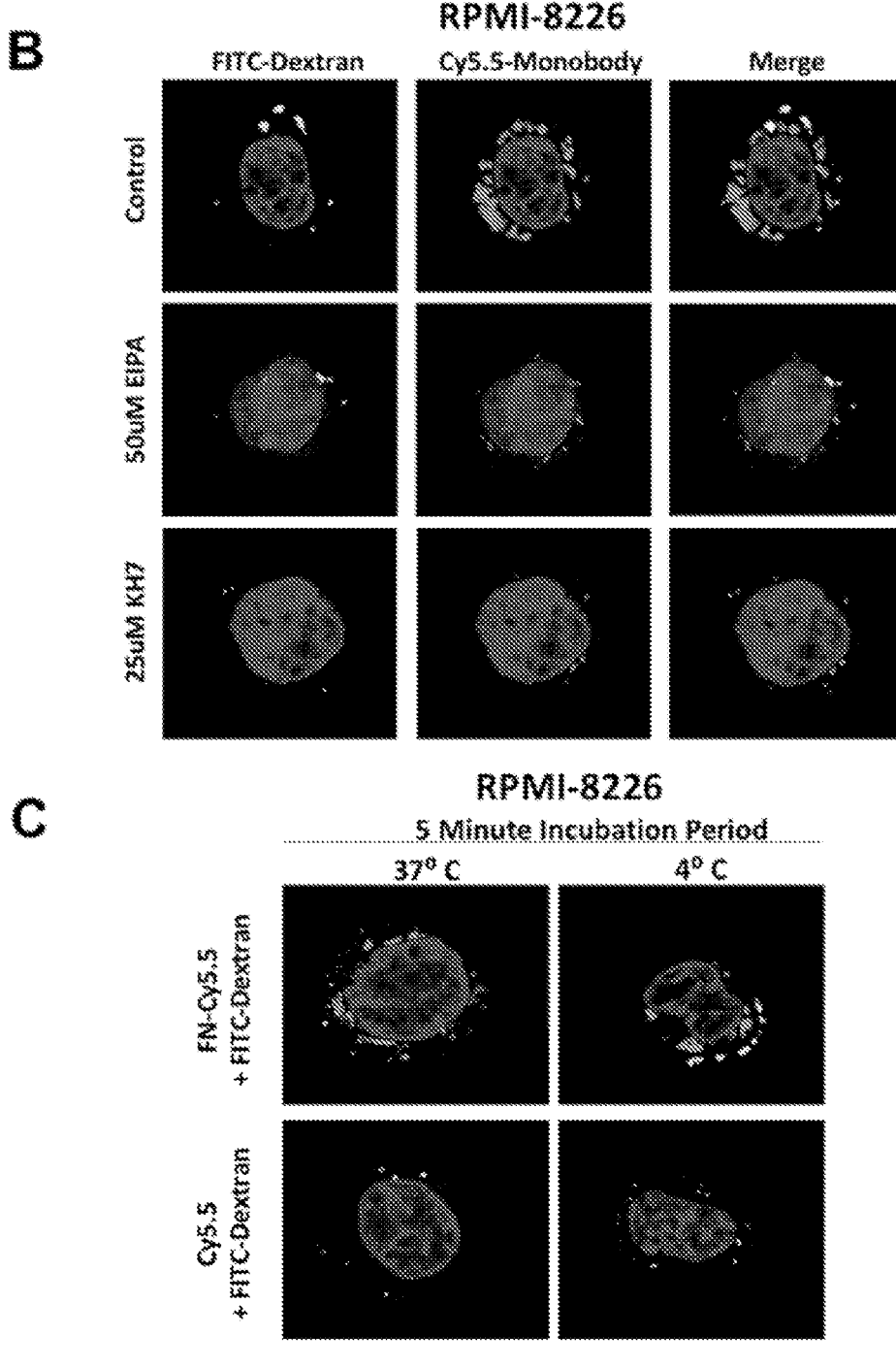
Figure 15A:
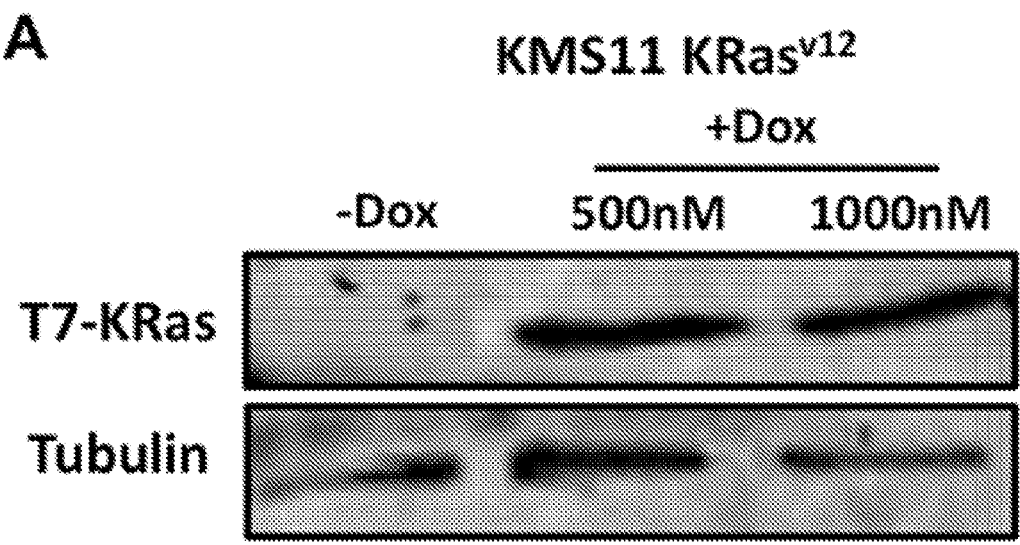
FIGS. 15A-15C shows a mutant KRas inducible system that was created in WT Ras KMS11 multiple myeloma cells.
Figure 15B:
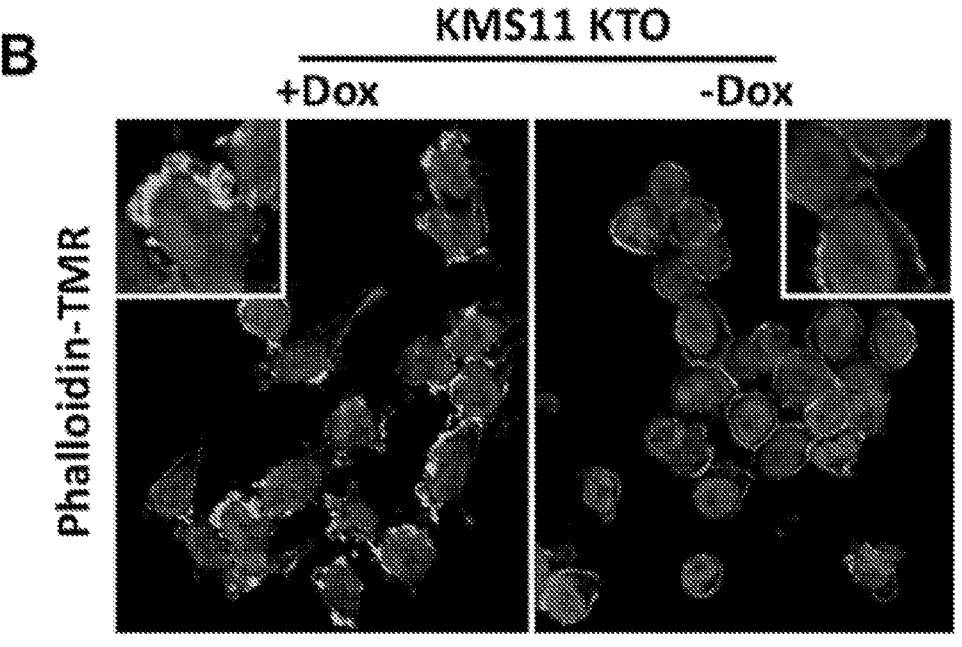
Figure 15C:
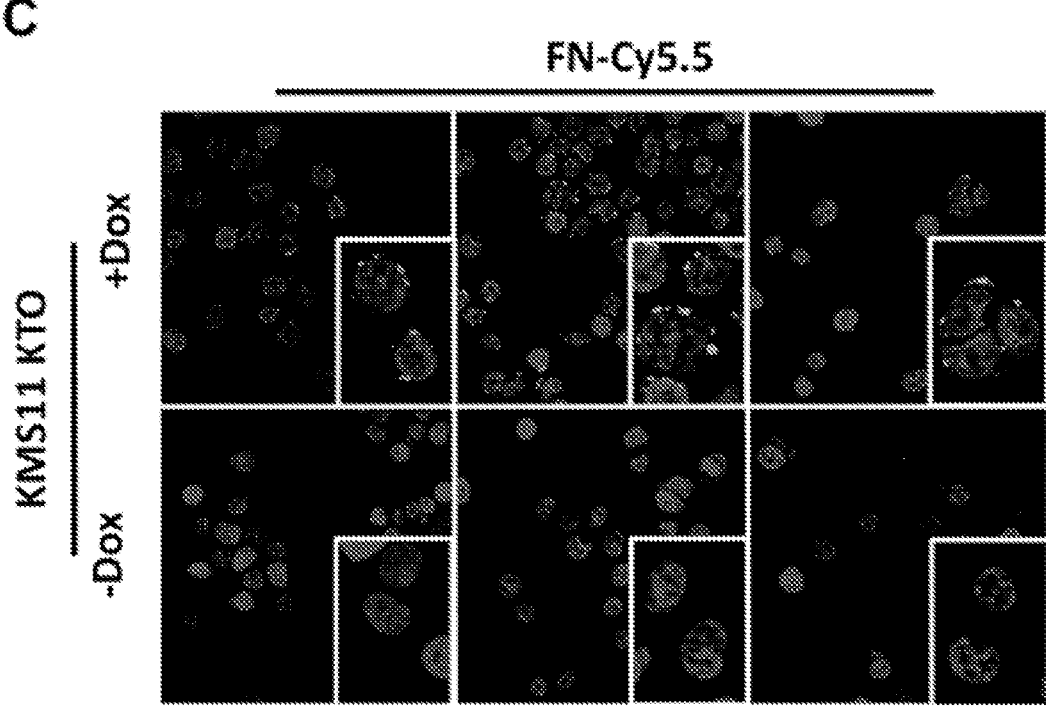
Figure 16:
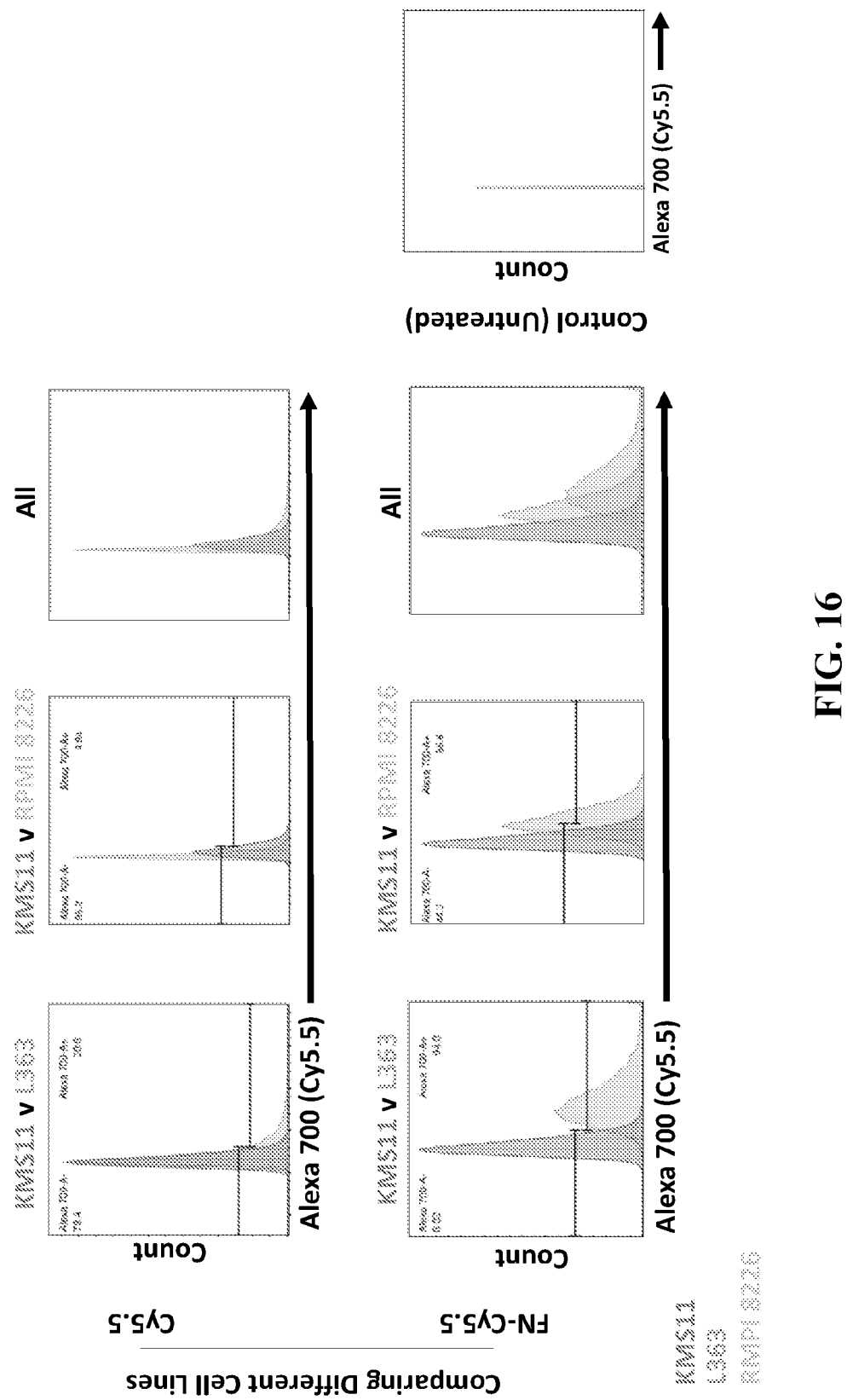
FIG. 16 shows flow cytometry analysis of Cy5.5 and FN-Cy5.5 in oncogenic Ras various multiple myeloma cell lines.

The differential uptake was established not only in cell lines of solid tumors, but also in blood cancer such as multiple myeloma. The wildtype Ras cell line (KMS11) displays little to no macropinocytosis compared to mutant NRas (L363) or mutant KRas (RPMI-8226) multiple myeloma cell lines (FIGS. 14 and 16). Using a similar system to the HeLa KRas$^{V12}$ inducible system, we created an inducible KRas$^{V12}$ cell system in wild type KRas KMS11 multiple myeloma cells. As seen in the HeLa system, KRas$^{V12}$ expression in KMS11 cells was evident with doxy-cycline treatment and dependent for FN-Cy5.5 cellular uptake (FIG. 15).

Example 3—Differential Cytotoxicity of Non-Binding Protein Drug Conjugate

Figures 4A, 4B:
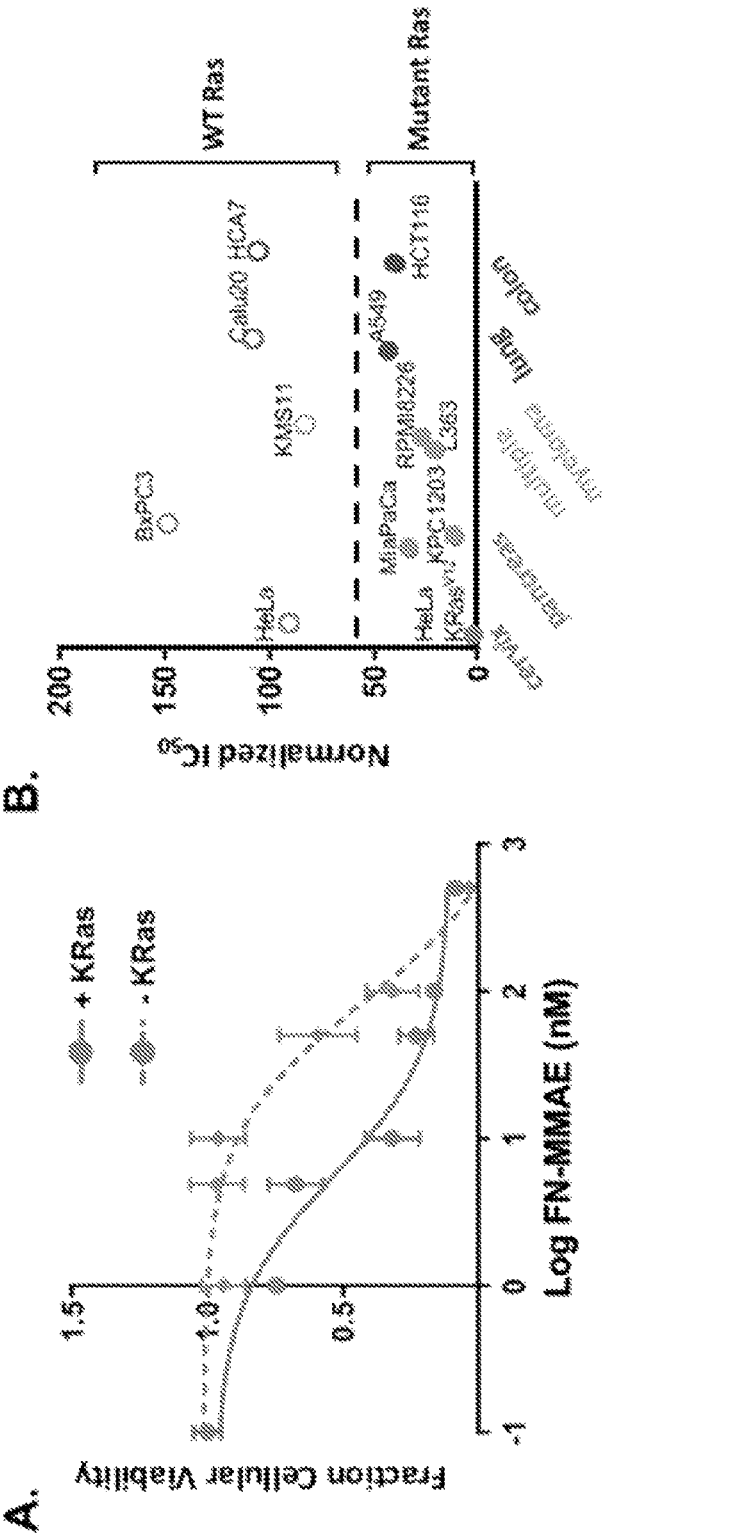
FIGS. 4A-4C show the enhanced toxicity of monobody-drug conjugates in oncogenic KRas cell lines.

By creating a cell impermeable protein complex, the ability of the non-binding FN domain to enter cells without macropinocytosis is hampered, creating a selective cellular uptake pathway. To investigate if Ras mutational status confers differential cytotoxicity, increasing concentrations of FN-MMAE conjugate on cell viability in HeLa and HeLa KRasV$^{12}$ cells were tested. Indeed, a 16-fold decrease in IC50 in HeLa KRasV$^{12}$ cells compared to HeLa cells was detected (FIG. 4A). FN-MMAE was also highly effective in mutant Ras pancreatic, multiple myeloma, lung, and colon cancer cell lines (FIG. 4B). After normalizing IC50 values of FN-MMAE to free MMAE to control for cellular differences, a significant decrease in cytotoxicity for cell lines without mutant Ras (macropinocytosis-negative) compared to cell lines with mutant Ras (macropinocytosis-positive) was observed, suggesting a macropinocytosis dependency.

Figure 4C:
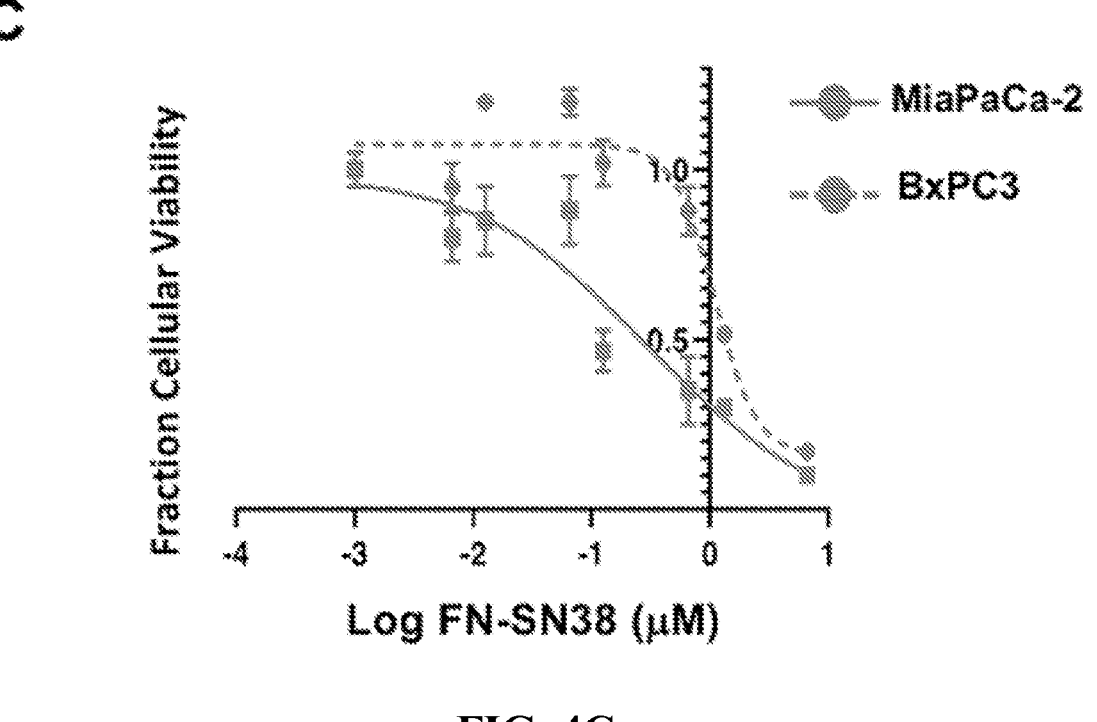

A unique attribute to the non-binding FN domain platform is the flexibility of cargo conjugation. This was tested in FIG. 4C where SN-38, an irinotecan metabolite was conjugated to FN. Similar to FN-MMAE, a mutant Ras specific cytotoxicity was observed in the PDAC cell lines treated.

Figure 5A:
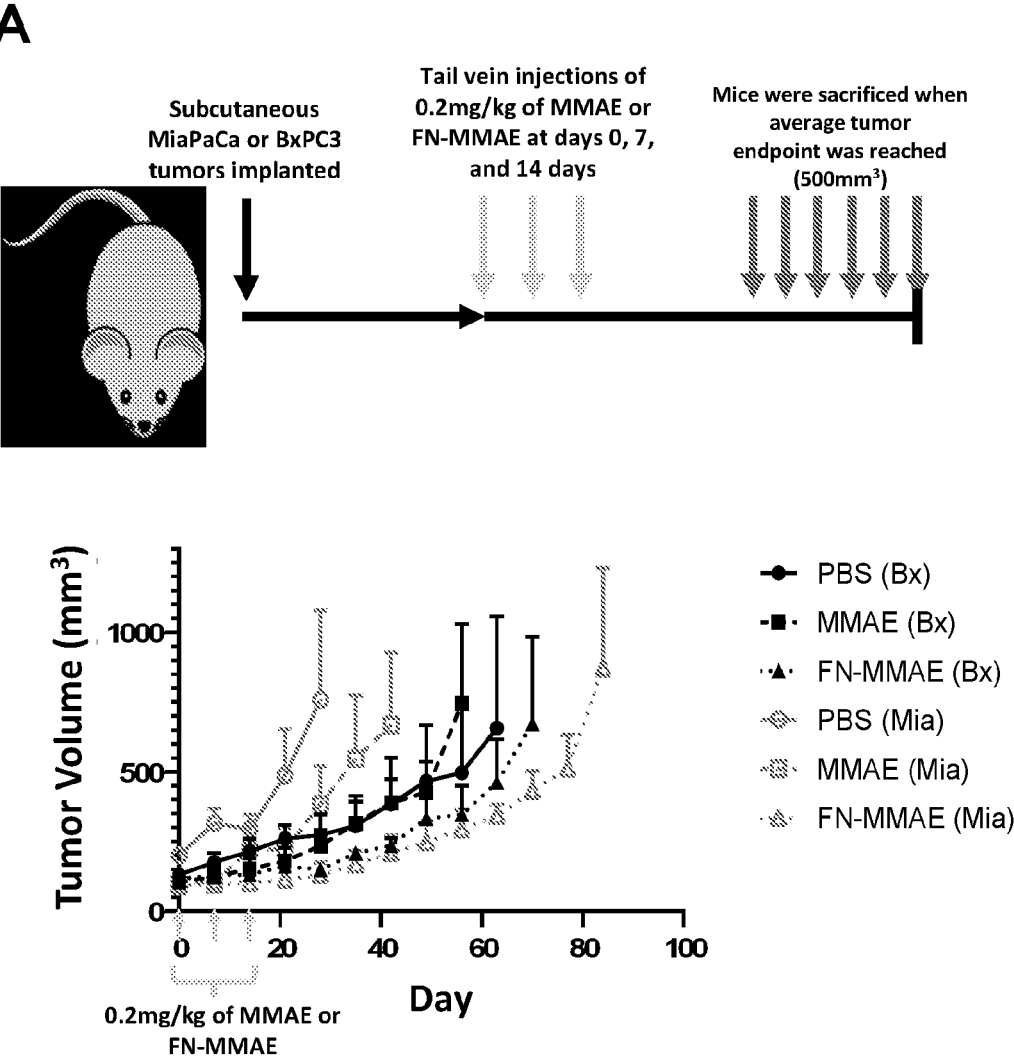
FIGS. 5A-5B show the enhanced toxicity of FN-MMAE (monobody) in oncogenic KRas cell lines in vivo.
Figure 5B:
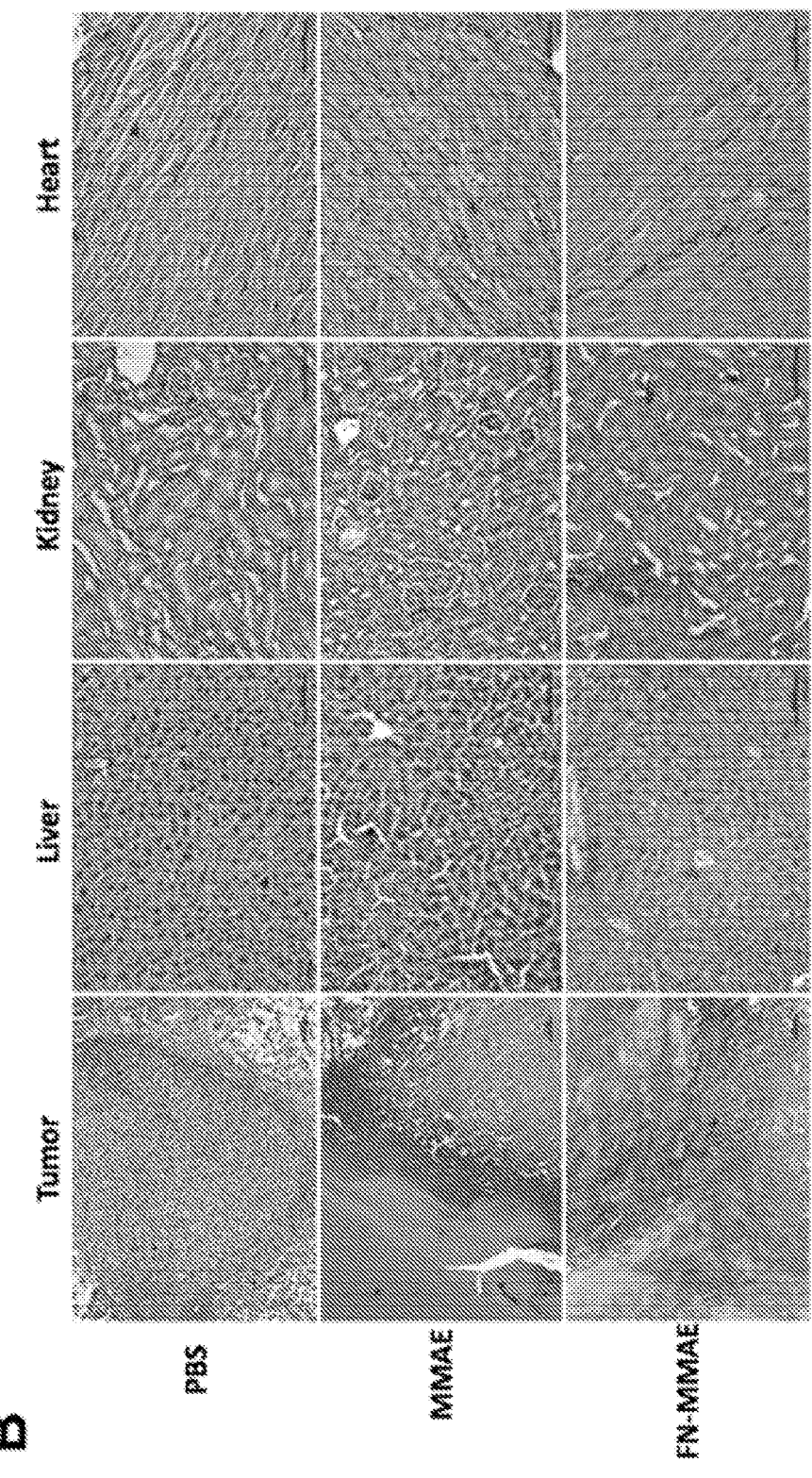
Figure 6A:
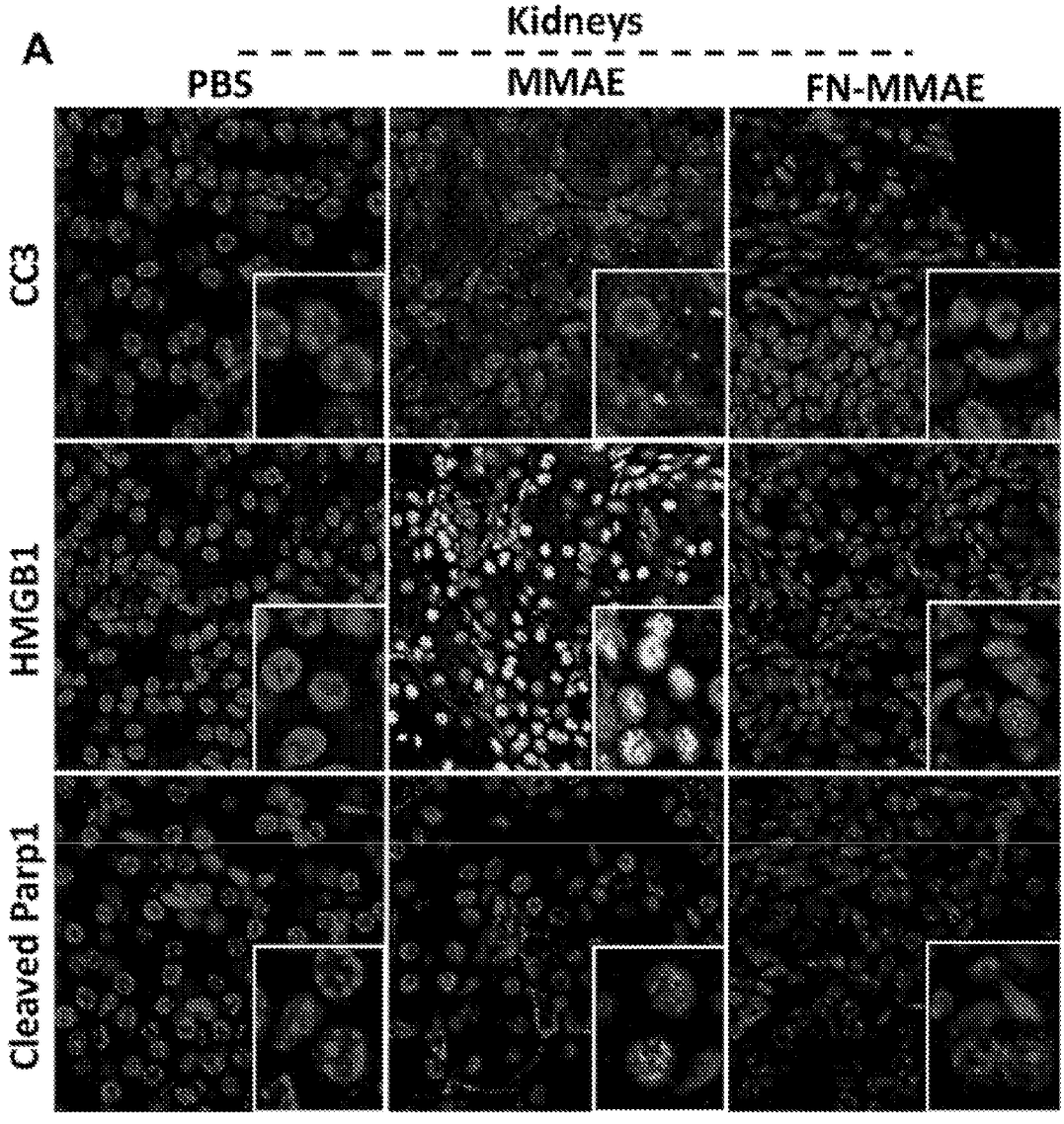
FIGS. 6A-6B show ex vivo analysis and mode of action of MMAE.
Figure 6A:
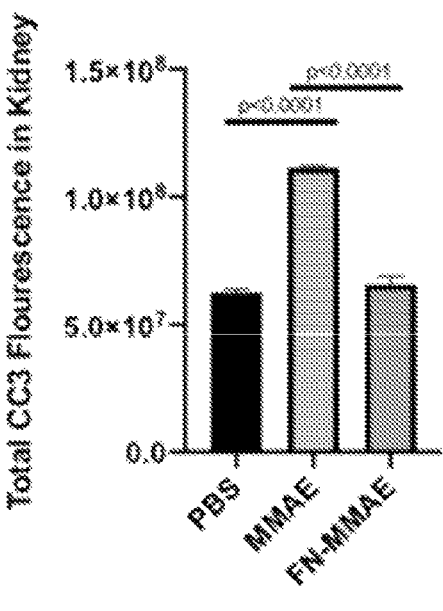
Figure 6A:
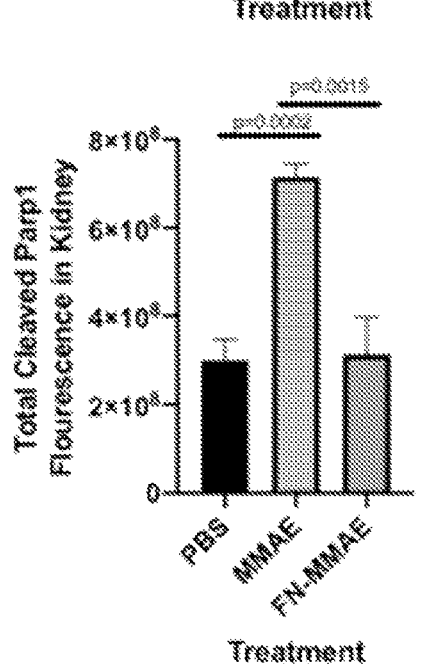
Figure 6A:
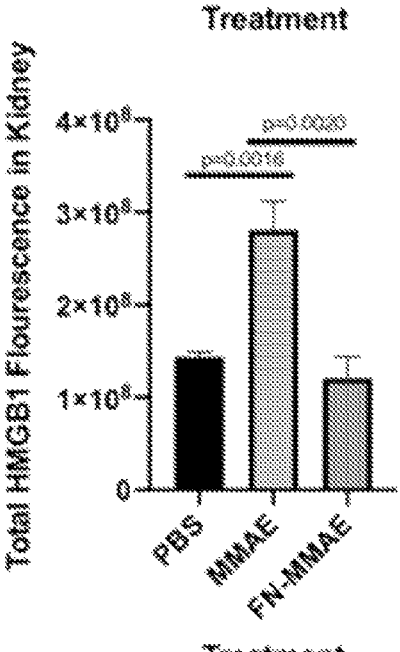
Figure 6B:
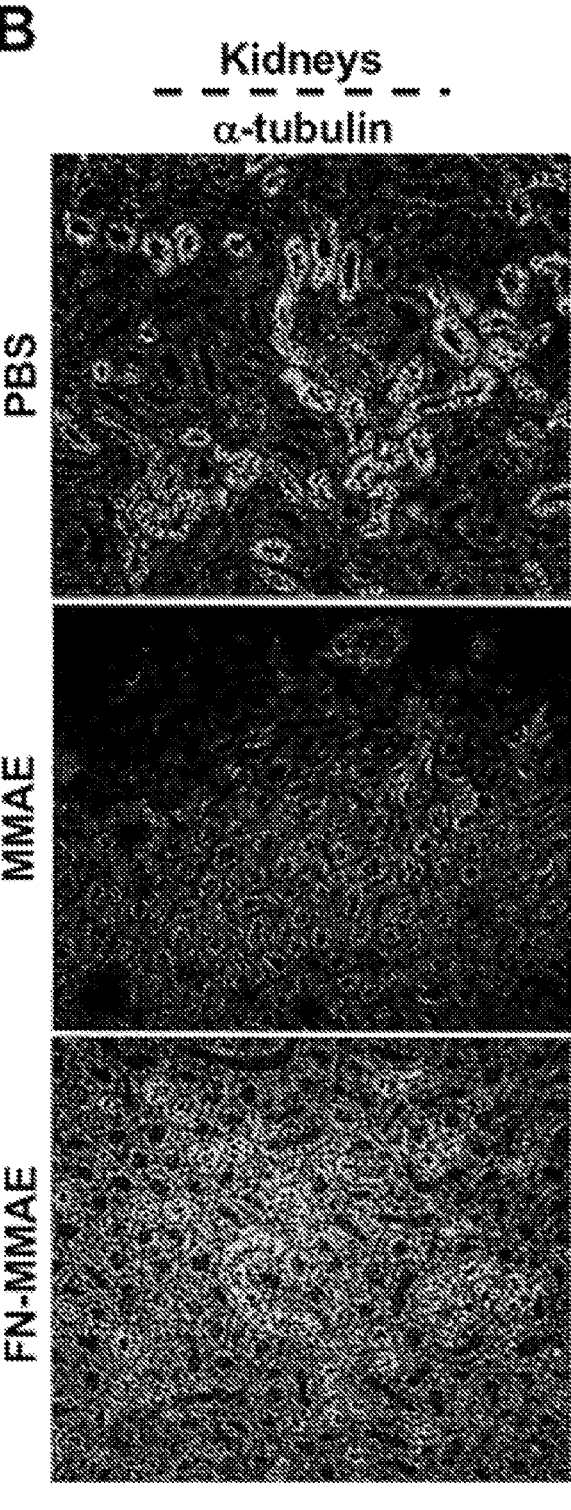

To test the effects in vivo, a MIA PaCa-2 subcutaneous tumor model was used to compare the efficacy of PBS, MMAE, and FN-MMAE (FIG. 5A). After tumors were established, three injections of 0.2 mg/kg drug with respect to MMAE concentration was administered every 7 days. Compared to MMAE, the FN-MMAE conjugate more effectively reduced tumor growth by extending the time to reach the tumor size end point by 47 days (2.2-fold increase). FN-MMAE also showed reduced non-specific toxicities, specifically reduced cleaved caspase 3, HMGB1, and increased tubulin staining (MMAE mode of cytotoxicity is as a tubulin destabilizer) in both the kidneys and liver (FIGS. 5B, 6A, and 6B). This highlights the specificity of reduced uptake by non-macropinocytic cells in relation to free drug, which contributes to the selective effect of the non-binding FN domain-drug conjugate.

Example 4—Biodistribution of Non-Binding Protein Drug Conjugate

Figures 7A, 7B:
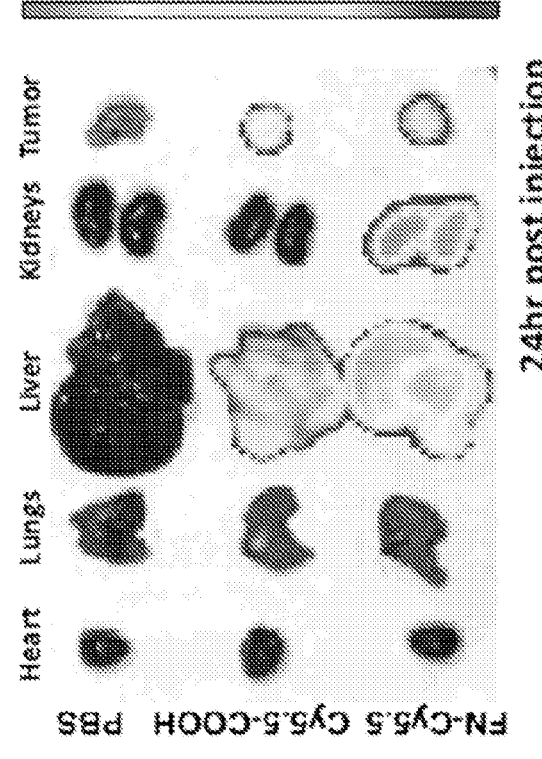
FIGS. 7A-7E show tumor specific biodistribution.
Figure 7C:
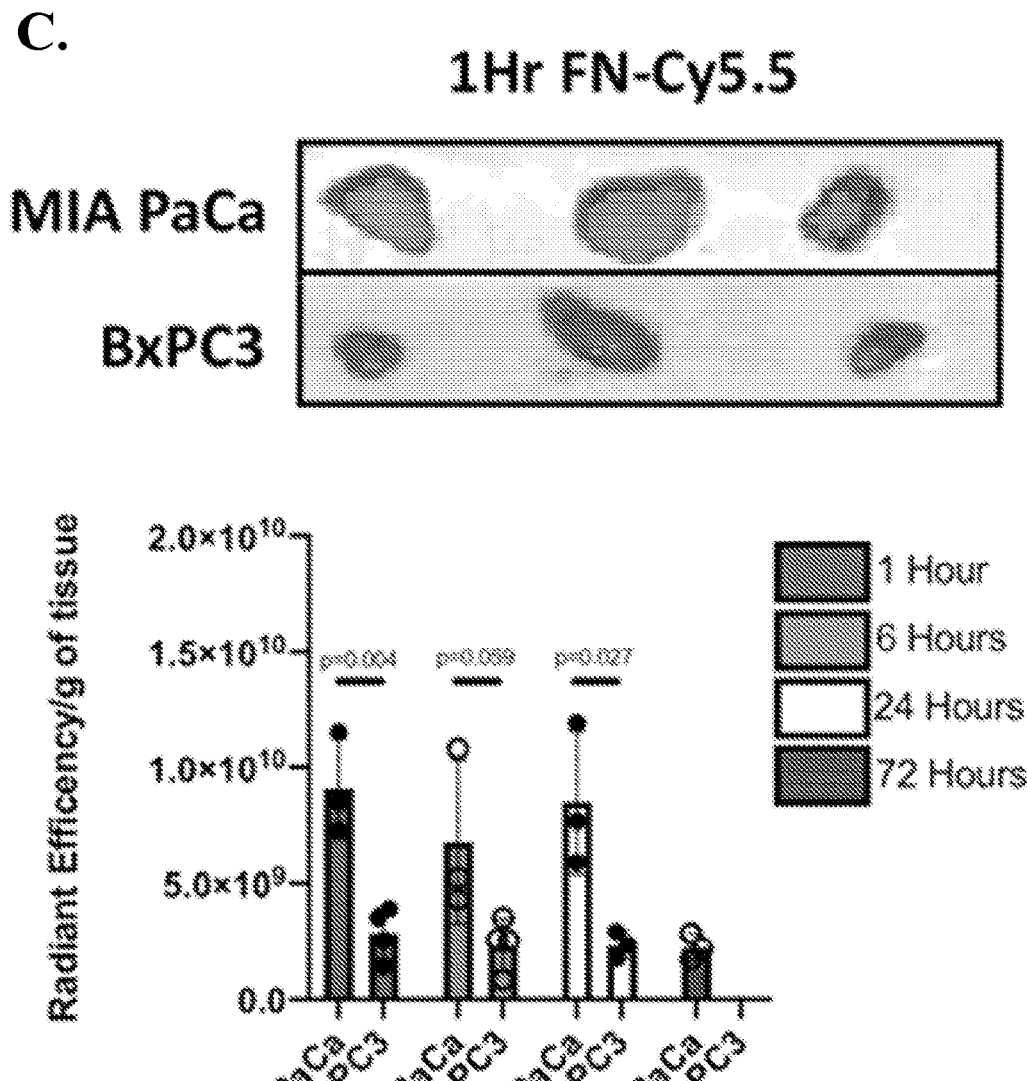
Figures 7D, 7E:
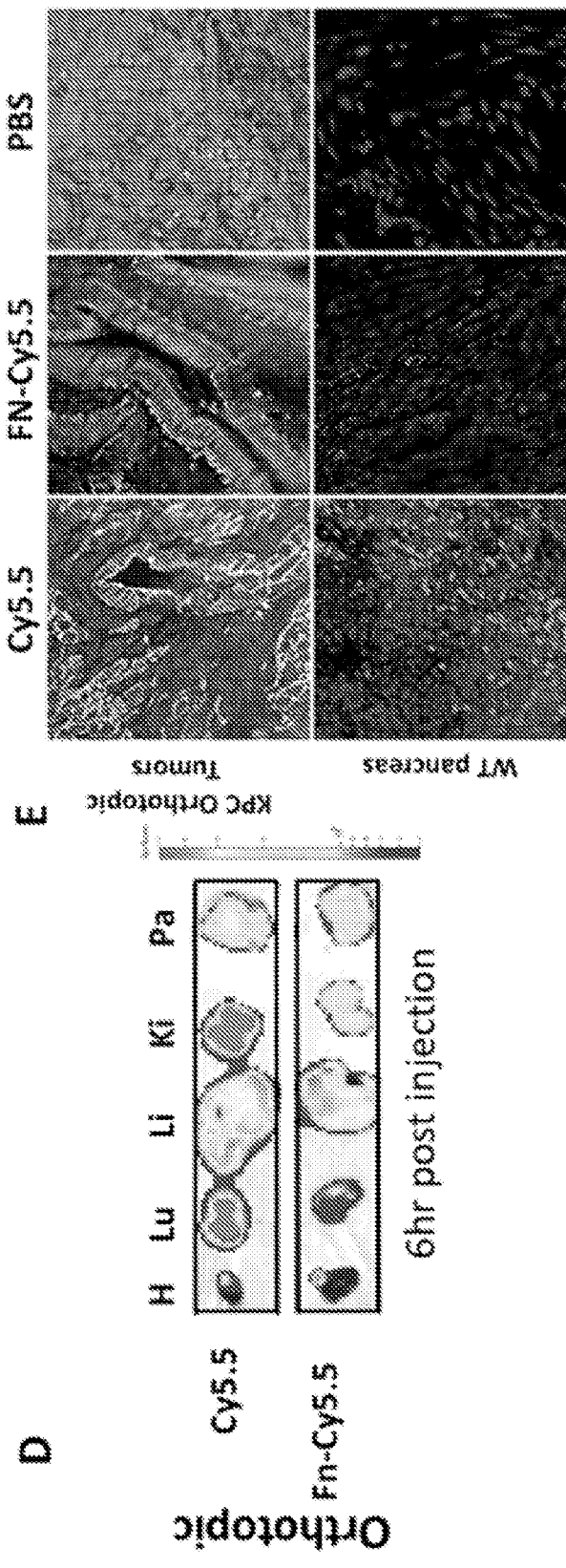

The size of the non-binding FN domain confers a very short half-life in the serum and clearance is subjected to renal excretion with high collection in the kidneys and liver. To test whether non-binding FN domain biodistribution was altered, a MIA PaCa-2 xenograft mouse model was used. After injecting mice harboring established tumors with FN-Cy5.5 or Cy5.5, an IVIS time course uncovered an altered pharmacokinetic profile of the non-binding FN domain compared to the free Cy5.5 (FIGS. 7A and 7B). Next, MIA PaCa-2 and BxPC3 xenograft mice were treated on the same time course to see if mutational status affected retention (FIG. 7C). At 1, 4, and 24 hr time points, there was over a doubling in uptake in the MIA-PaCa-2 tumors. Next, KPC cells were orthotopically injected into the pancreas of mice to assess the treatment and biodistribution of PBS, Cy5.5-COOH or FN-Cy5.5. Ex vivo imaging of whole tumors and tumor slices were analyzed at the 6 hr timepoint (FIGS. 7D and 7E) displaying selective uptake for the tumorigenic pancreas compared to wild pancreas, which was not seen in the small molecule treatment.

Figures 8A, 8B:
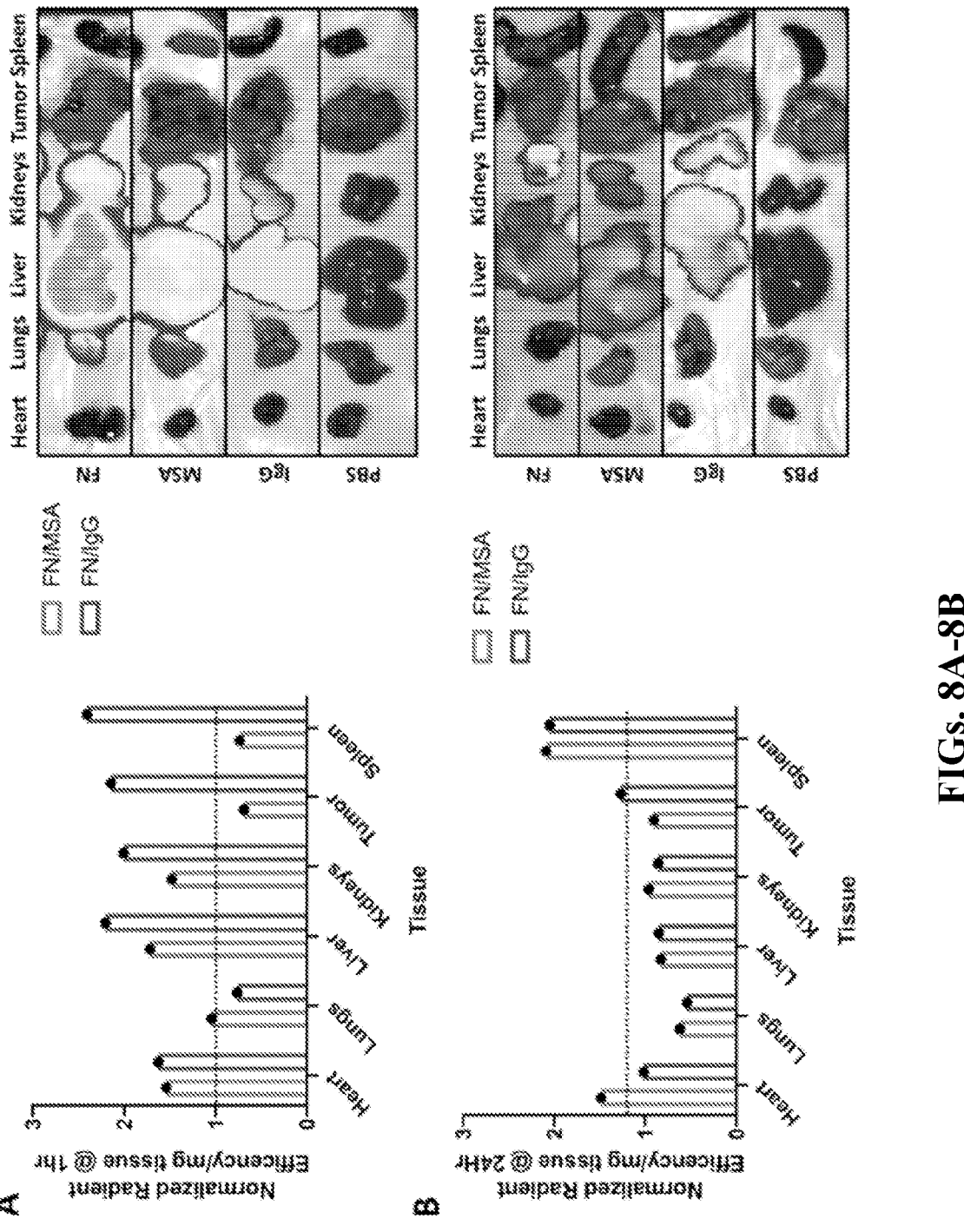
FIGS. 8A-8C show biodistribution of FN-Cy5.5 in the orthotopic implant KPC tumor bearing mice. KPC tumor bearing mice were treated with PBS or 5 nmol, in reference to Cy5.5, of FN-Cy5.5, Mouse albumin (MSA)-Cy5.5, and mouse IgG-Cy5.5. Mice were sacrificed at 1 hr (FIG. 8A) and 24 hr (FIG. 8B) to observe ex vivo biodistribution and blood fluorescence (FIG. 8C). Graphs represent normalized values comparing MSA to FN (red) and IgG to FN (blue). At 1 hr, FN had drastic 2 fold increases in the kidneys and liver, displaying quick excretion while having similar or increased tumor retention. At 24 hr, FN showed reductions in kidneys and liver while have similar tumor values (90% and 100% for MSA and IgG respectively). FN displayed a 3-fold decrease in blood fluoresce at 1 hr, again highlighting quick excretion compared to other protein conjugates.
Figure 8C:
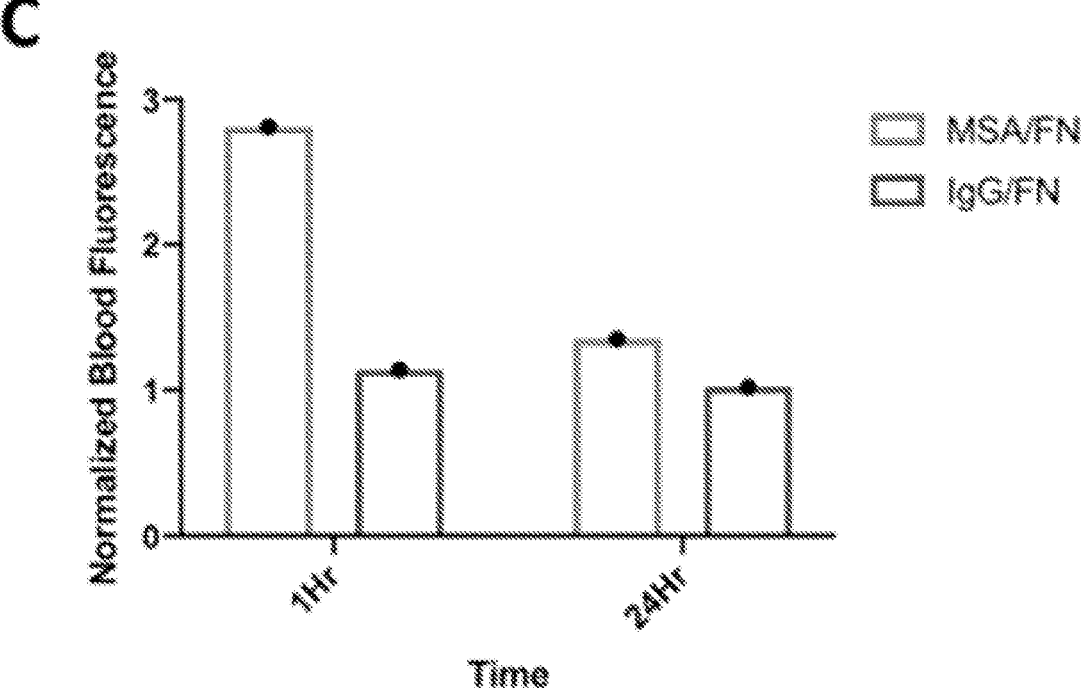
Figure 9A:
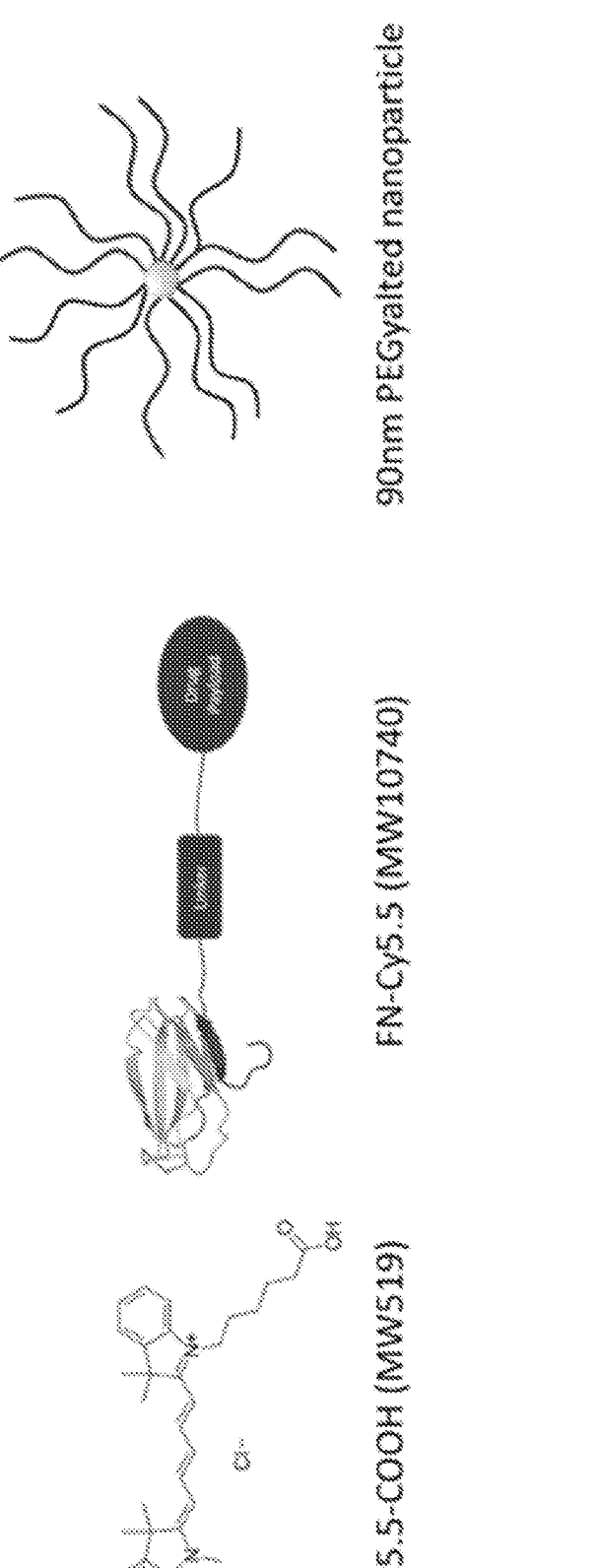
FIGS. 9A-9C show lymph node analysis of FN-Cy5.5.
Figure 9B:
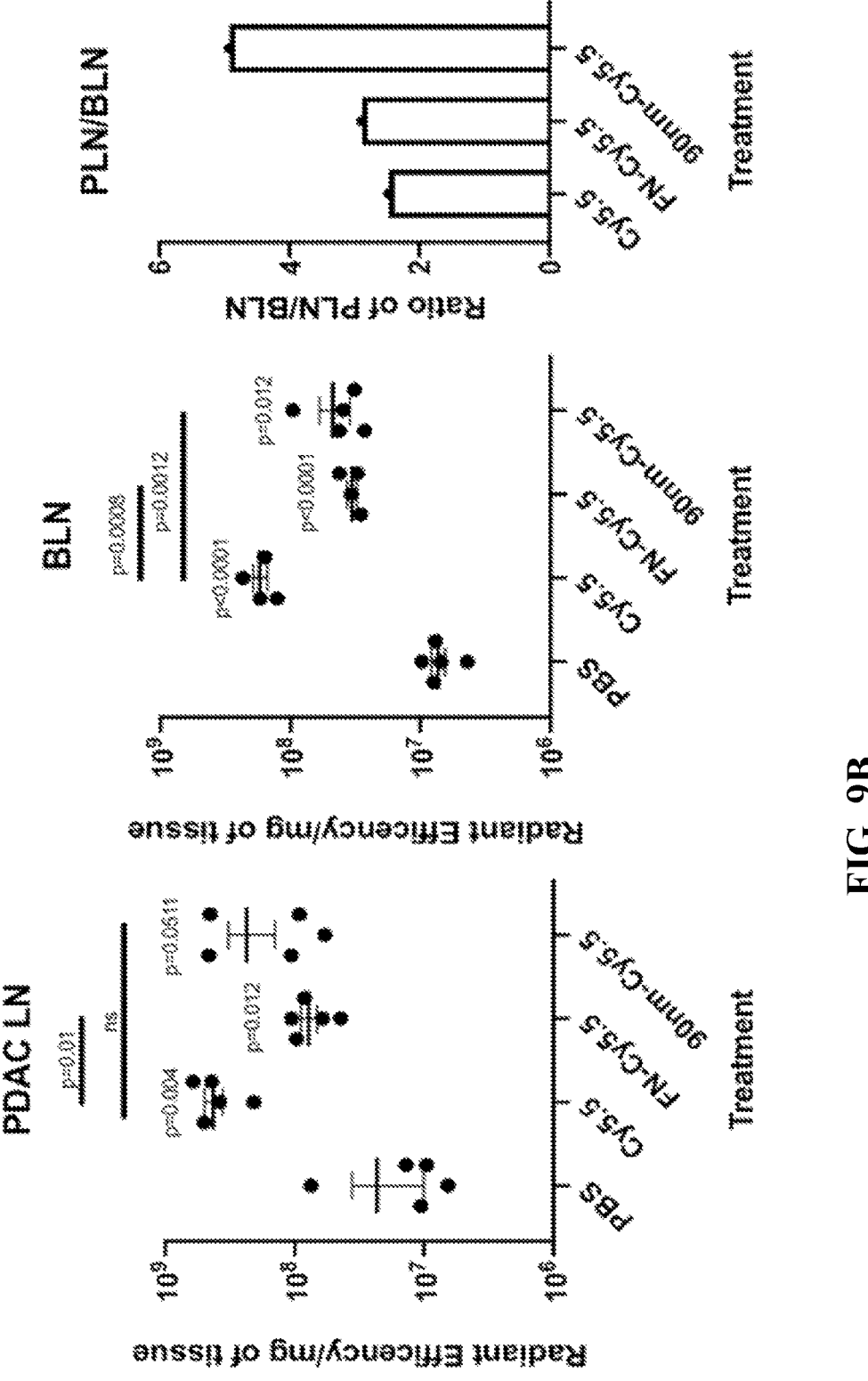
Figure 9C:
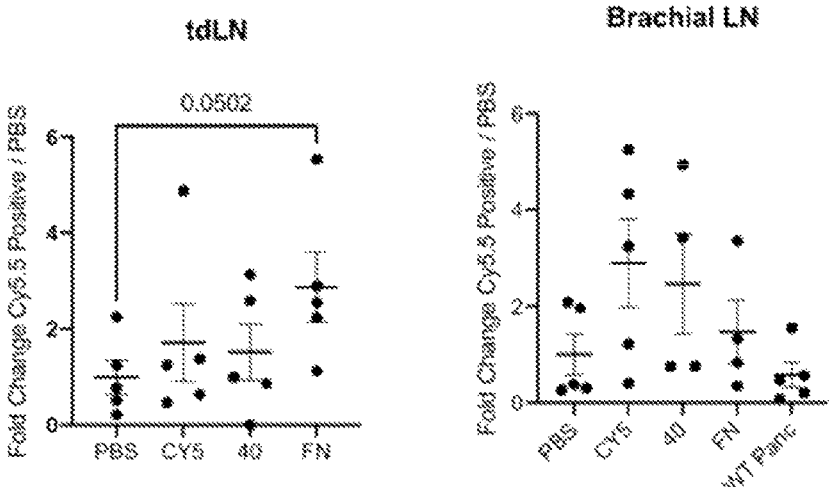
Figure 9C:
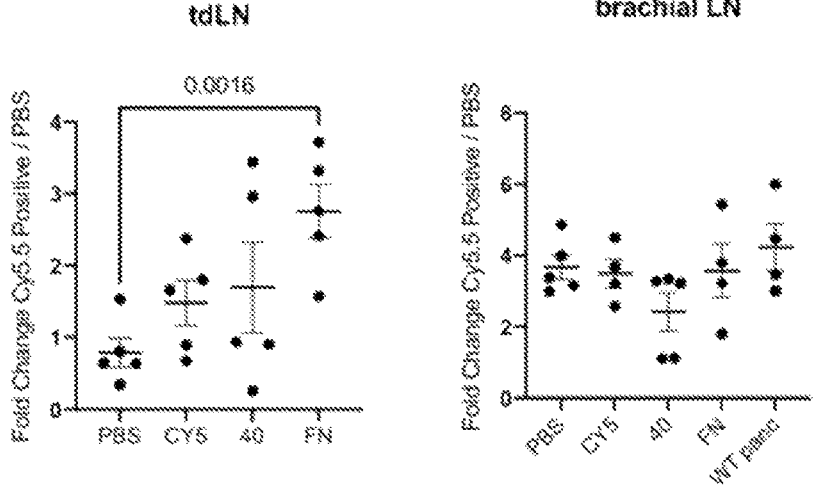

In FIG. 8, biodistribution of PBS, FN-Cy5.5, Mouse albumin (MSA)-Cy5.5, or mouse IgG-Cy5.5 was observed in orthotopic implanted KPC tumor bearing mice at 1 hr and 24 hr after IP injection. Mice were sacrificed at 1 hr (FIG. 8A) and 24 hr (FIG. 8B) to observe ex vivo biodistribution and blood fluorescence (FIG. 8C). At 1 hr, FN-Cy5.5 had drastic 2-fold increases in the kidneys and liver compared to other protein conjugates, displaying quick excretion while having similar or the increased tumor retention. At 24 hr, FN-Cy5.5 showed reductions in kidneys and liver while have similar tumor values (90% and 100% for MSA and IgG respectively). FN-Cy5.5 displayed a 3-fold decrease in blood fluoresce at 1 hr, again highlighting quick excretion compared to other protein conjugates.

In FIG. 9, the uptake of the non-binding protein drug conjugate in pancreatic draining lymph nodes was examined. There is a susceptibility for metastases within the pancreatic draining lymph node in PDAC patients, while also being a target tissue for a number of encouraging tumor immunomodulator therapies currently being developed. To assess if there is selective uptake in this tissue, and more specifically dendritic cells, orthotopic implanted KPC tumor bearing mice were treated with PBS, Cy5.5-COOH, and FN-Cy5.5. Ex vivo IVIS imaging showed FN-Cy5.5 localized within PDAC draining lymph nodes (FIG. 9A) and had a 2 fold preference for PDAC lymph nodes compared to bronchial lymph nodes. Additionally, lymph nodes were digested and flow cytometry was used to observe Cy5.5 positive cells (FIGS. 9B and 9C). There was over a 2-fold increase in positive Cy5.5 cells for FN conjugate as compared to free drug, signifying an improved dendritic cell uptake with the material delivery. Together this data indicates that not only is the FN platform selectively retained in pancreatic lymph nodes, but also the FN conjugate can significantly improve drug uptake.

Figure 10A:
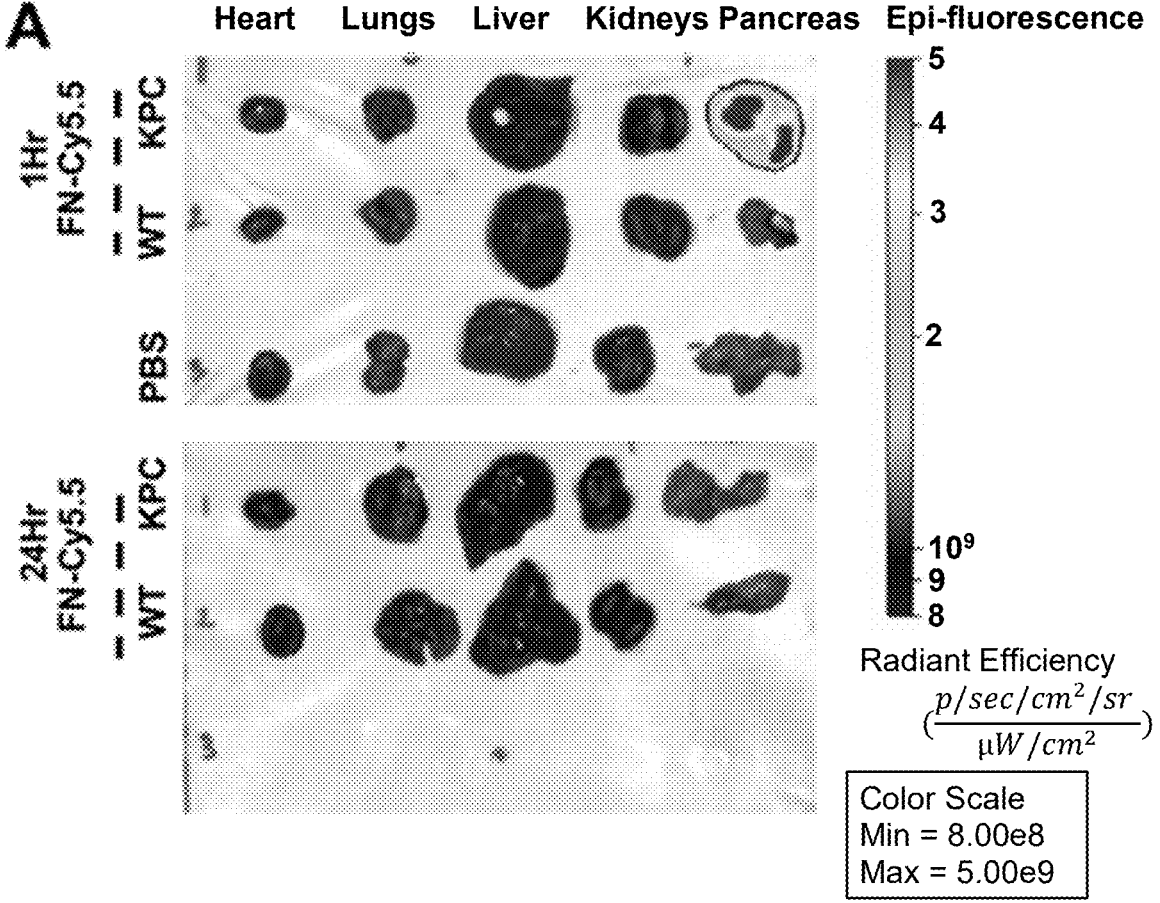
FIGS. 10A-10D show FN-Cy5.5 uptake in a genetically modified mouse model of PDAC. Autochonous LSL-KPC$^{G12V}$; LSLp53$^{R172H}$; p48Cre (KPC, 4mo) and wild type (WT, 4 mo) mice were treated with FN-Cy5.5. Ex vivo images of FIG. 10A depict biodistribution in various organs at 1 hr and 24 hr. Normalized radiant efficiency displays preference for tumor uptake in the autochonous KPC model (FIG. 10B).
Figure 10B:
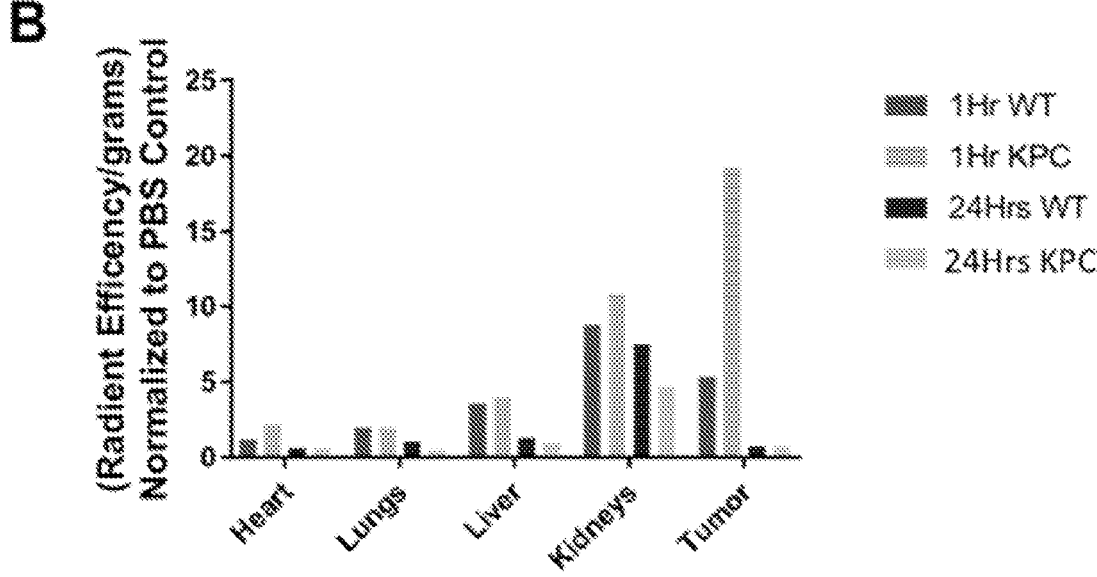
Figure 10C:
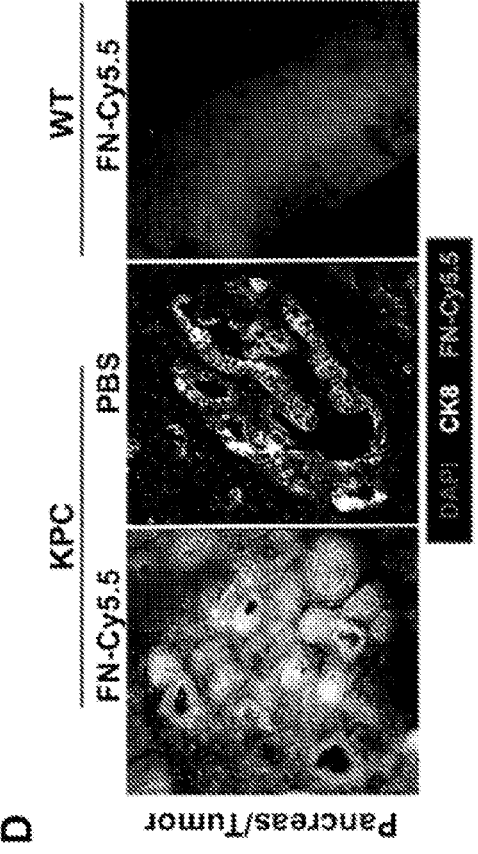
Figure 10D:
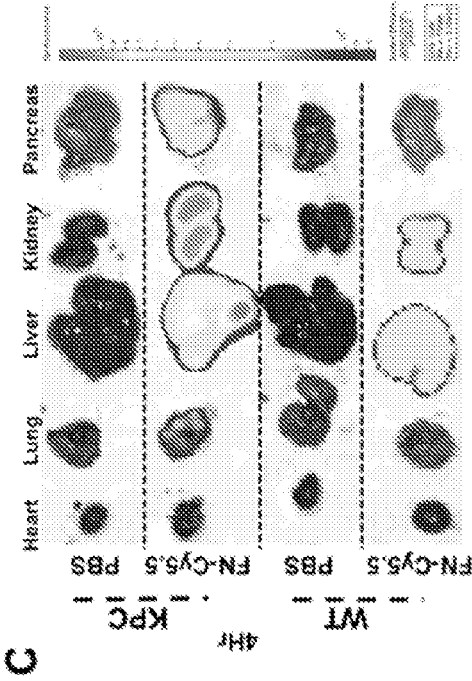
Figure 11:
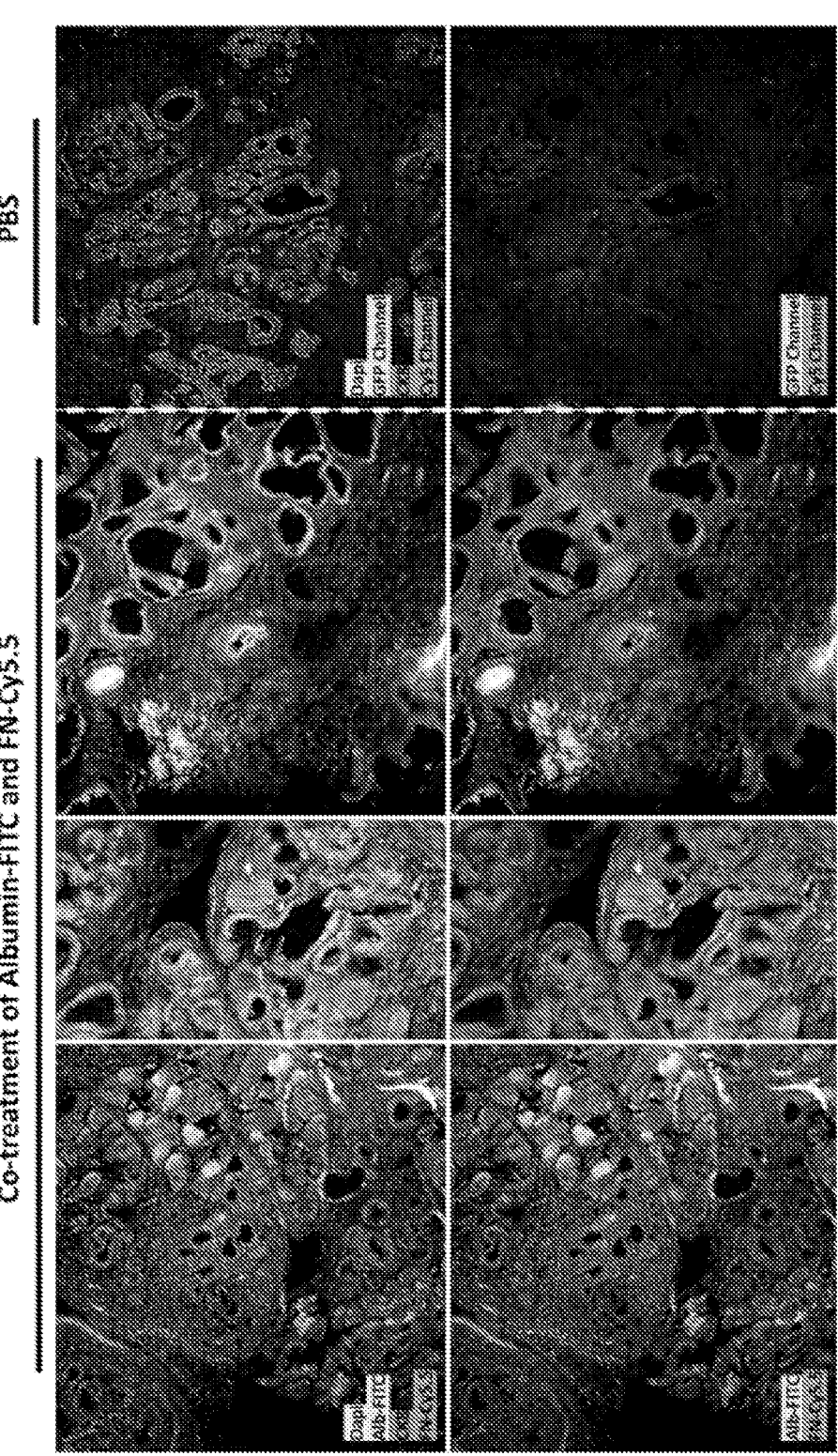
FIG. 11 shows ex vivo tumor analysis in autochonous LSL-KPC$^{G12V}$; LSLp53$^{R172H}$; p48Cre (KPC, 4mo) mice treated with FN-Cy5.5 and albumin-FITC for 2 hrs. Mice were sacrificed and ex vivo analysis was carried out on tumors displaying albumin-FITC (green), FN-Cy5.5 (purple), tumor cell marker CK8 (orange), and dapi (blue). Visually, FN-Cy5.5 was observed to potentially stain CK8 positive PDAC tumor ducts better than albumin-FITC but this observation did show some variance based on tumor location.

Further analysis using a genetically modified mouse model, KrasG12D; Trp53R172H,p48Cre (KPC), which recapitulates human PDAC progression from pancreatic intraepithelial neoplasm (PanIN) lesions to PDAC and metastasis, also displayed enhanced tumor selective uptake in the pancreas (FIGS. 10A-C). Importantly, less uptake was observed in the pancreata of wild type mice (FIGS. 10A-C). Consistent Cy5.5 staining throughout the tumor was observed, indicating good penetration and colocalization with a cancer cell marker (CK8) (FIG. 10D). Importantly, it was found that the FN-Cy5.5 complex reached the tumor and was internalized by the tumor cells. Additionally, similar experimentation was carried out with co-delivery of an albumin bound FITC and FN-Cy5.5. Albumin based therapy is a current standard of care in PDAC treatment. Albumin-FITC and FN-Cy5.5 both colocalized within the established pancreatic tumors in mice (FIG. 11). The ex vivo analysis showed FN-Cy5.5 had a larger propensity to be up taken in the PanINs, as seen by colocalization with CK8 staining, while albumin-FITC had larger accumulation in the extracellular tumor microenvironment.

Figure 17:
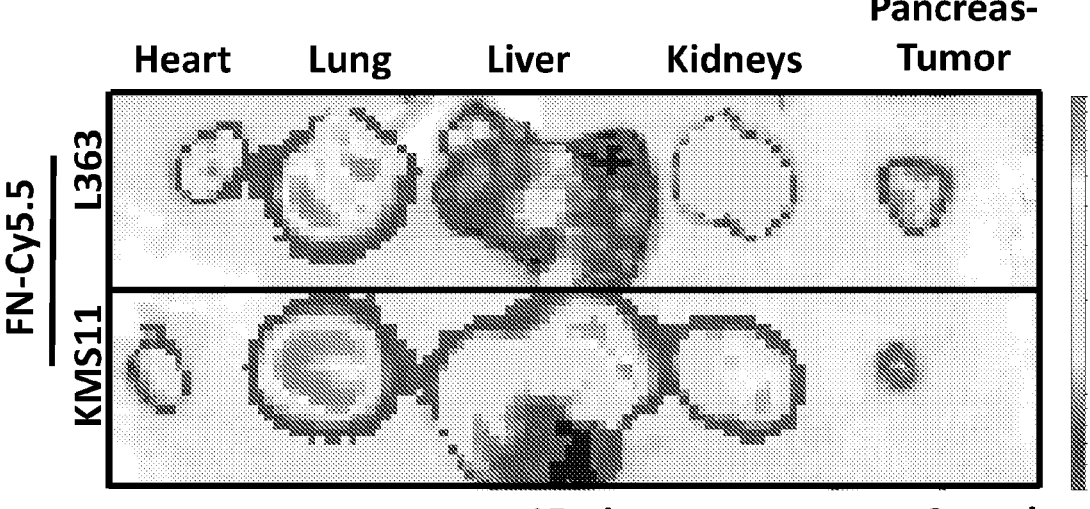
FIG. 17 shows differential tumor accumulation based on Ras status in multiple myeloma. Biodistribution of FN-Cy5.5 in mice bearing mutant NRas L363 or WT Ras KMS11 tumors. The mutant Ras tumor displayed a significant increase in FN-Cy5.5 uptake as compared to the WT tumor (bottom graph).
Figure 17:
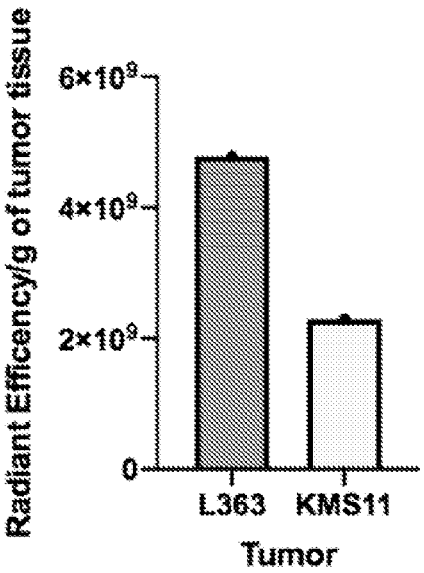

The differential tumor accumulation was established not only in solid tumors, but also in blood cancer such as multiple myeloma. The mutant NRas xenograft (L363) displays heightened tumor accumulation of FN-Cy5.5 compared to the wildtype Ras xenograft (KMS11) (FIG. 17).

The pharmacokinetic profile exhibited indicates non-binding FN domain treatment will be a superior asset for both chemotherapy and imaging. Creating a short half-life while maintaining tumor retention and enhanced penetration will allow for larger dose regiments with limited toxicities, making treatment potentially more effective.

Example 5—Imaging Using the Non-Binding Protein Conjugate

Current imaging methods have created modest solutions to detect early stages of PDAC. Specifically, current MRI imaging systems have poor spatial resolution with moderate ability to detect lesions. Investigations into traditional PET agents ([18]FDG) have reported mixed results. [18]FDG also can detect inflammatory responses, making differentiation between pancreatitis and PDAC challenging. In preliminary studies using an orthotopic implanted KPC tumor (FIGS.

Figure 12A:
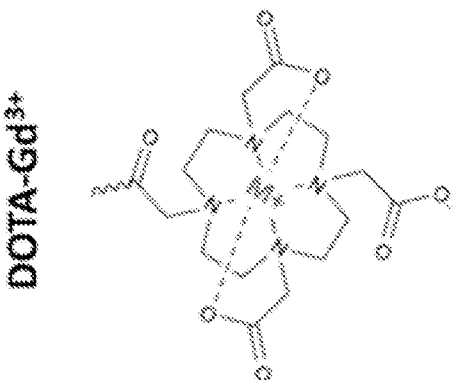
FIGS. 12A-12C show MRI detection using FN-DOTA-Gd$^{3+}$.
Figure 12A:
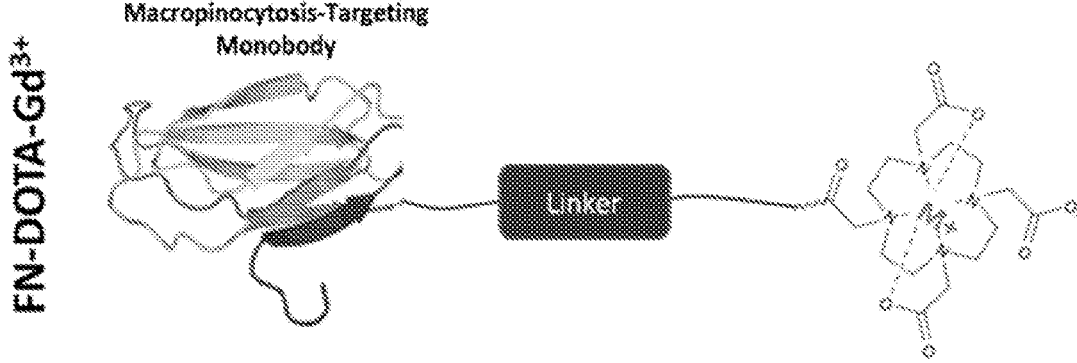
Figure 12B:
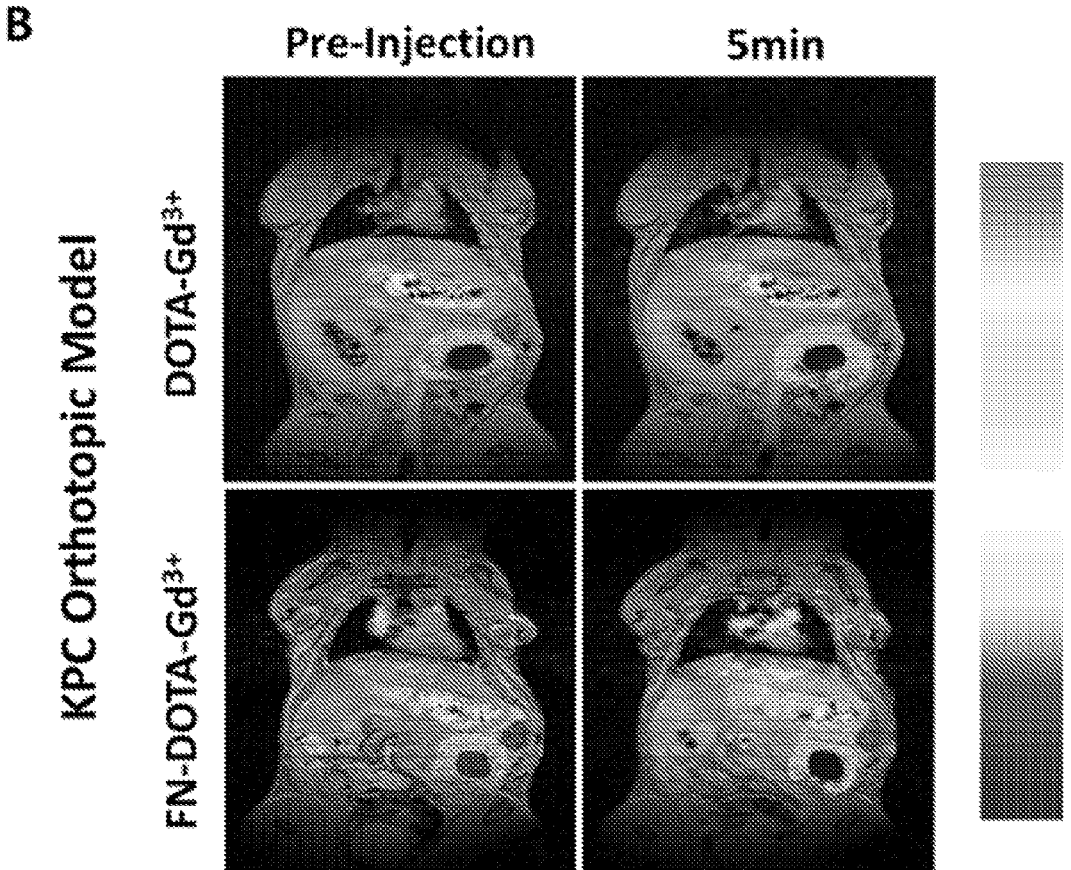
Figure 12C:
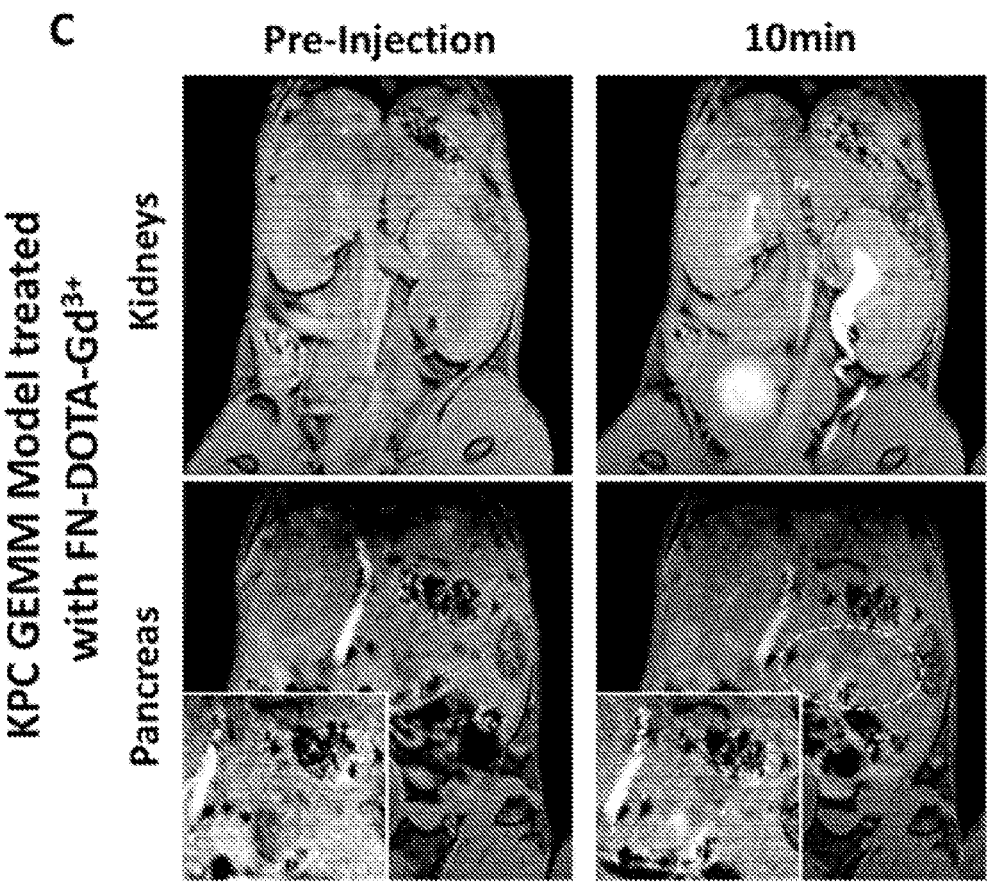
Figure 13A:
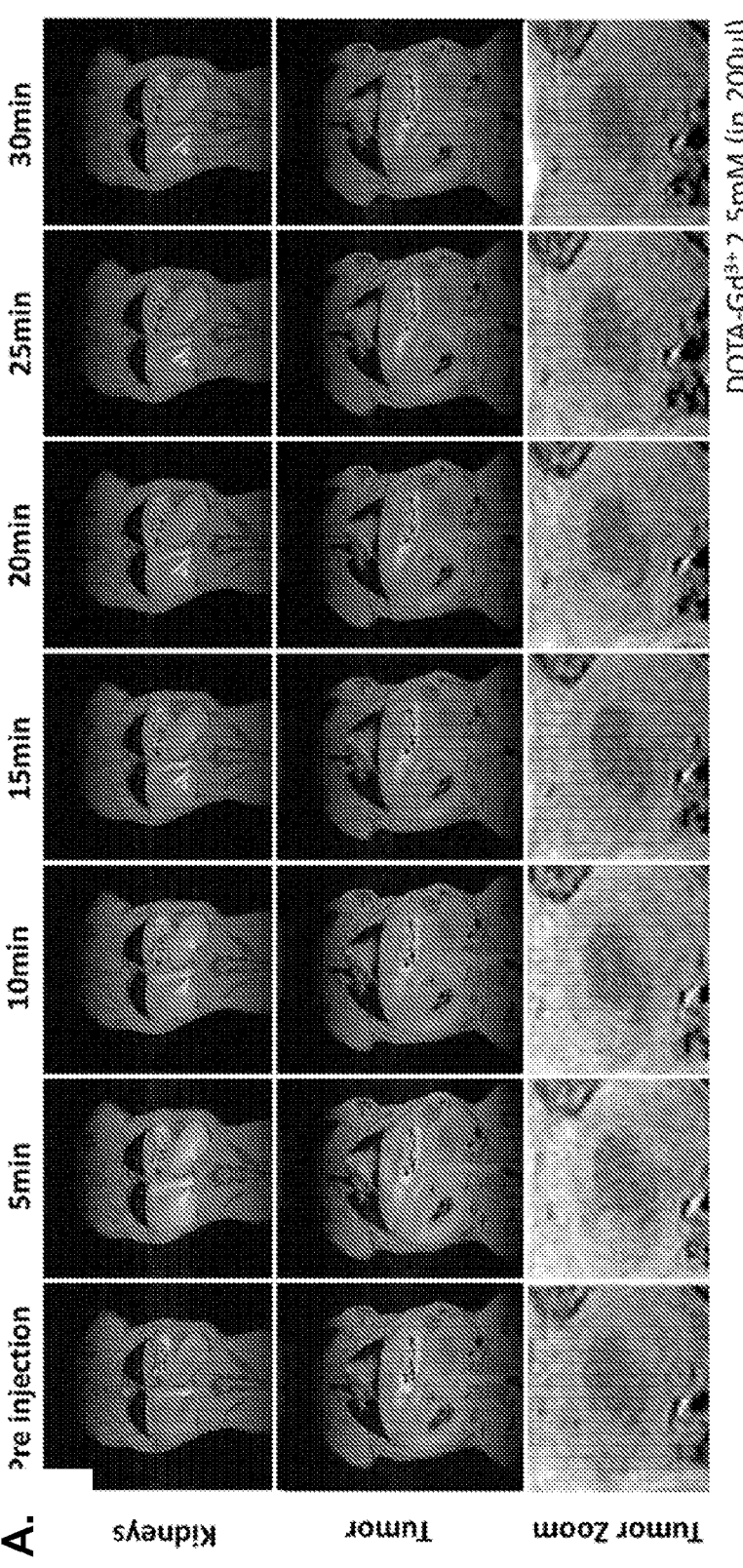
FIGS. 13A-13B show MRI imaging of KPC orthotopic tumors. MRI imaging of KPC orthotopic implanted tumors with (FIG. 13A) DOTA-Gd$^{3+}$ and (FIG. 13B) FN-DOTA-Gd$^{3+}$.
Figure 13B:
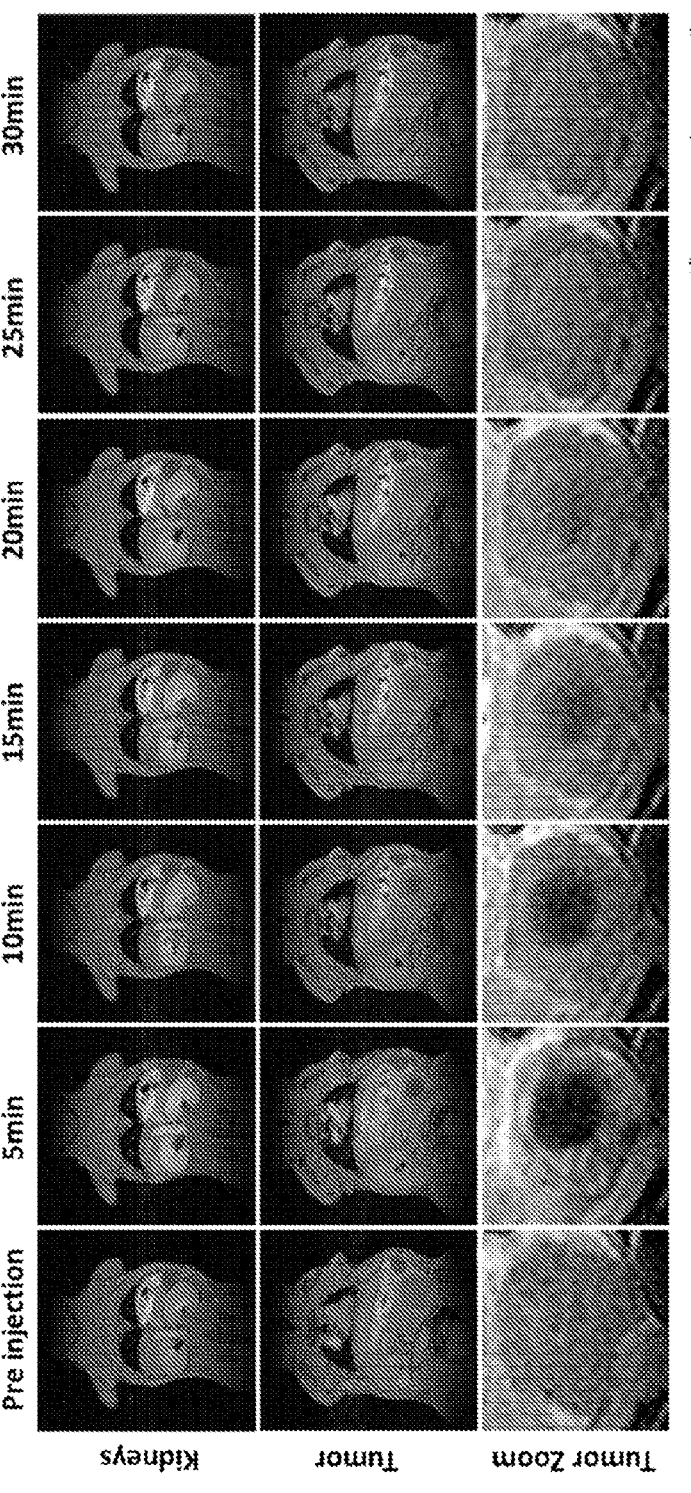

12B and 13) and an autochthonous KPC mouse model (FIGS. 12C and 13), FN-DOTA-Gd$^{3+}$ follows the same biodistribution as the fluorescent probes (FIG. 10A), with localization in the kidneys within 10 minutes post injection (FIGS. 12C and 13) and detection of tumor mass (FIG. 7B and FIG. 7C bottom-red arrowheads).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

---

What is claimed is:

1. A pharmaceutical composition comprising: a non-binding protein-drug conjugate and a pharmaceutically acceptable carrier, wherein said non-binding protein-drug conjugate comprises:
   [i] a first portion, said first portion comprising a non-binding human fibronectin type III (FN3) domain, wherein the non-binding FN3 domain comprises the amino acid sequence of SEQ ID NO: 2 or SEQ ID NO: 3, and wherein the amino acid sequence of SEQ ID NO: 2 does not comprise SEQ ID NO: 1;
   [ii] an amino acid linker within or coupled to the first portion; and
   [iii] a second portion coupled to said first portion via the amino acid linker, said second portion selected from a pharmaceutically active moiety or a diagnostic moiety.

2. The composition of claim 1, wherein:
   (a) the FN3 domain of the non-binding protein-drug conjugate further comprises one or more amino acid substitutions in its RGD amino acid sequence of its FG loop, which corresponds to amino acid residues 78-80 of SEQ ID NO: 2; and/or
   (b) the FN3 domain of the non-binding protein-drug conjugate further comprises one or more amino acid substitutions in the amino acid sequence of the BC loop, which corresponds to amino acid residues 24-30 of SEQ ID NO: 2.

3. The composition of claim 1, wherein the FN3 domain of the non-binding protein-drug conjugate is a non-binding human FN3 domain.

4. The composition of claim 1, wherein the FN3 domain of the non-binding protein-drug conjugate is a non-binding variant of the 10$^{th}$ type III fibronectin domain of human fibronectin ($^{10}$Fn3).

5. The composition of claim 1, wherein the FN3 domain comprising the amino acid sequence of SEQ ID NO: 2 comprises:
   an FG loop as set forth in SEQ ID NO: 4, which corresponds to amino acid residues 75-86 of SEQ ID NO: 2; and/or
   a BC loop as set forth in SEQ ID NO: 5, which corresponds to amino acid residues 24-30 of SEQ ID NO: 2.

6. The composition of claim 1, wherein the amino acid linker comprises a cysteine residue substitution within the FN3 domain of the first portion of the protein-drug conjugate; or wherein the amino acid linker comprises a cysteine residue addition at the FN3 domain C-terminus.

7. The composition of claim 1, wherein the amino acid linker is a cleavable linker.

8. The composition of claim 1, wherein the amino acid linker is a non-cleavable linker.

9. The composition of claim 1, wherein the first portion of the non-binding protein-drug conjugate comprises two or more FN3 domains linked together in tandem.

10. The composition of claim 1, wherein the second portion of the non-binding protein-drug conjugate is a pharmaceutically active moiety.

11. The composition of claim 10, wherein the pharmaceutically active moiety is a cancer therapeutic, an immunomodulatory agent, an oligonucleotide, or a wound healing agent.

12. The composition of claim 11, wherein the pharmaceutically active moiety is a cancer therapeutic selected from the group consisting of an antimetabolite, an alkaloid, an alkylating agent, an anti-mitotic agent, an antitumor antibiotic, a DNA binding drug, a toxin, an antiproliferative drug, a DNA antagonist, a radionuclide, a thermoablative agent, a proteolysis targeting chimera (PROTAC), a nucleic acid inhibitor, and an immune-modulatory agent.

13. The composition of claim 11, wherein the pharmaceutically active moiety is an immunomodulatory agent selected from the group consisting of a macrophage type-1 stimulating agent, a macrophage type-2 stimulating agent, a T cell stimulating agent, a dendritic cell stimulating agent, and a neutrophil stimulating agent.

14. The composition of claim 11, wherein the pharmaceutically active moiety is an oligonucleotide selected from the group consisting of an siRNA, an aptamer, an miRNA, an immunostimulatory oligonucleotide, a splice-switching oligonucleotide, and guide RNA.

15. The composition of claim 1, wherein the second portion of the non-binding protein-drug conjugate is a diagnostic moiety.

16. A method of imaging a tumor in a subject, said method comprising: selecting a subject having a tumor and administering to said subject the composition of claim 15.

17. The composition of claim 1, wherein:
   (a) the FN3 domain of the non-binding protein-drug conjugate further comprises one or more amino acid substitutions in its RGD amino acid sequence of its FG loop, which corresponds to amino acid residues 78-80 of SEQ ID NO: 2; and
   (b) the FN3 domain of the non-binding protein-drug conjugate further comprises one or more amino acid substitutions in the amino acid sequence of the BC loop, which corresponds to amino acid residues 24-30 of SEQ ID NO: 2.

* * * * *

SEQUENCE LISTING

```
<160> NUMBER OF SEQ ID NOS: 37

<210> SEQ ID NO 1
<211> LENGTH: 94
<212> TYPE: PRT
<213> ORGANISM: Homo sapiens

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 94
<212> TYPE: PRT
<213> ORGANISM: Artificial
<220> FEATURE:
<223> OTHER INFORMATION: non-binding FN3 domain consensus sequence
<220> FEATURE:
<221> NAME/KEY: MISC_FEATURE
<222> LOCATION: (3)..(3)
<223> OTHER INFORMATION: Xaa at position 3 is selected from Asp, Ser,
      Ala, Glu, Gly, Lys, Asn, and Gln
<220> FEATURE:
<221> NAME/KEY: MISC_FEATURE
<222> LOCATION: (7)..(7)
<223> OTHER INFORMATION: Xaa at position 7 is selected from Asp, Ser,
      Ala, Glu, Gly, Lys, Asn, and Gln
<220> FEATURE:
<221> NAME/KEY: MISC_FEATURE
<222> LOCATION: (24)..(24)
<223> OTHER INFORMATION: Xaa at position 24 is selected from Ser, Ala,
      Glu, Gly, Lys, Asn, Asp, and Gln
<220> FEATURE:
<221> NAME/KEY: MISC_FEATURE
<222> LOCATION: (25)..(25)
<223> OTHER INFORMATION: Xaa as position 25 is selected from Pro, Ser,
      Ala, Glu, Gly, Lys, Asn, Asp, and Gln
<220> FEATURE:
<221> NAME/KEY: MISC_FEATURE
<222> LOCATION: (26)..(26)
<223> OTHER INFORMATION: Xaa as position 26 is selected from Ala, Ser,
      Glu, Gly, Lys, Asn, Asp, and Gln
<220> FEATURE:
```

-continued

```
<221> NAME/KEY: MISC_FEATURE
<222> LOCATION: (27)..(27)
<223> OTHER INFORMATION: Xaa as position 27 is selected from Val, Ser,
      Ala, Glu, Gly, Lys, Asn, Asp, and Gln
<220> FEATURE:
<221> NAME/KEY: MISC_FEATURE
<222> LOCATION: (28)..(28)
<223> OTHER INFORMATION: Xaa as position 28 is selected from Thr, Ser,
      Ala, Glu, Gly, Lys, Asn, Asp, and Gln
<220> FEATURE:
<221> NAME/KEY: MISC_FEATURE
<222> LOCATION: (30)..(30)
<223> OTHER INFORMATION: Xaa as position 30 is selected from Arg, Ser,
      Ala, Glu, Gly, Lys, Asn, Asp, and Gln
<220> FEATURE:
<221> NAME/KEY: MISC_FEATURE
<222> LOCATION: (75)..(75)
<223> OTHER INFORMATION: Xaa as position 75 is selected from Val, Ser,
      Ala, Glu, Gly, Lys, Asn, Asp, and Gln
<220> FEATURE:
<221> NAME/KEY: MISC_FEATURE
<222> LOCATION: (76)..(76)
<223> OTHER INFORMATION: Xaa as position 76 is selected from Thr, Ser,
      Ala, Glu, Gly, Lys, Asn, Asp, and Gln
<220> FEATURE:
<221> NAME/KEY: MISC_FEATURE
<222> LOCATION: (77)..(77)
<223> OTHER INFORMATION: Xaa as position 77 is selected from Gly, Ser,
      Ala, Glu, Lys, Asn, Asp, and Gln
<220> FEATURE:
<221> NAME/KEY: MISC_FEATURE
<222> LOCATION: (78)..(78)
<223> OTHER INFORMATION: Xaa as position 78 is selected from Arg, Ser,
      Ala, Glu, Gly, Lys, Asn, Asp, and Gln
<220> FEATURE:
<221> NAME/KEY: MISC_FEATURE
<222> LOCATION: (79)..(79)
<223> OTHER INFORMATION: Xaa as position 79 is selected from Gly, Ser,
      Ala, Glu, Lys, Asn, Asp, and Gln
<220> FEATURE:
<221> NAME/KEY: MISC_FEATURE
<222> LOCATION: (80)..(80)
<223> OTHER INFORMATION: Xaa as position 80 is selected from Asp, Ser,
      Ala, Glu, Gly, Lys, Asn, and Gln
<220> FEATURE:
<221> NAME/KEY: MISC_FEATURE
<222> LOCATION: (81)..(81)
<223> OTHER INFORMATION: Xaa as position 81 is selected from Ser, Ala,
      Glu, Gly, Lys, Asn, Asp, and Gln
<220> FEATURE:
<221> NAME/KEY: MISC_FEATURE
<222> LOCATION: (82)..(82)
<223> OTHER INFORMATION: Xaa as position 82 is selected from Pro, Ser,
      Ala, Glu, Gly, Lys, Asn, Asp, and Gln
<220> FEATURE:
<221> NAME/KEY: MISC_FEATURE
<222> LOCATION: (83)..(83)
<223> OTHER INFORMATION: Xaa as position 83 is selected from Ala, Ser,
      Glu, Gly, Lys, Asn, Asp, Ala, Asn, Asp, and Gln

<400> SEQUENCE: 2

Val Ser Xaa Val Pro Thr Xaa Leu Glu Val Val Ala Ala Thr Pro Thr
1               5                   10                  15

Ser Leu Leu Ile Ser Trp Asp Xaa Xaa Xaa Xaa Xaa Val Xaa Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Xaa Xaa Xaa Xaa Xaa Xaa
65                  70                  75                  80

Xaa Xaa Xaa Ser Ser Lys Pro Ile Ser Ile Asn Tyr Arg Thr
            85                  90
```

```
<210> SEQ ID NO 3
<211> LENGTH: 94
<212> TYPE: PRT
<213> ORGANISM: Artificial
<220> FEATURE:
<223> OTHER INFORMATION: non-binding FN3 domain

<400> SEQUENCE: 3

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Ser Ser Ser Ser Ser Ser
65                  70                  75                  80

Ser Ser Ser Ser Ser Lys Pro Ile Ser Ile Asn Tyr Arg Thr
                85                  90

<210> SEQ ID NO 4
<211> LENGTH: 9
<212> TYPE: PRT
<213> ORGANISM: Artificial
<220> FEATURE:
<223> OTHER INFORMATION: FG loop variant

<400> SEQUENCE: 4

Ser Ser Ser Ser Ser Ser Ser Ser Ser
1               5

<210> SEQ ID NO 5
<211> LENGTH: 7
<212> TYPE: PRT
<213> ORGANISM: Artificial
<220> FEATURE:
<223> OTHER INFORMATION: BC loop variant

<400> SEQUENCE: 5

Ser Ser Ser Ser Ser Val Ser
1               5

<210> SEQ ID NO 6
<211> LENGTH: 93
<212> TYPE: PRT
<213> ORGANISM: Homo sapiens

<400> SEQUENCE: 6

Gly Pro Val Glu Val Phe Ile Thr Glu Thr Pro Ser Gln Pro Asn Ser
1               5                   10                  15

His Pro Ile Gln Trp Asn Ala Pro Gln Pro Ser His Ile Ser Lys Tyr
            20                  25                  30

Ile Leu Arg Trp Arg Pro Lys Asn Ser Val Gly Arg Trp Lys Glu Ala
            35                  40                  45

Thr Ile Pro Gly His Leu Asn Ser Tyr Thr Ile Lys Gly Leu Lys Pro
        50                  55                  60

Gly Val Val Tyr Glu Gly Gln Leu Ile Ser Ile Gln Gln Tyr Gly His
65                  70                  75                  80

Gln Glu Val Thr Arg Phe Asp Phe Thr Thr Thr Ser Thr
```

-continued

```
                     85                    90

<210> SEQ ID NO 7
<211> LENGTH: 91
<212> TYPE: PRT
<213> ORGANISM: Homo sapiens

<400> SEQUENCE: 7

Val Ala Thr Ser Glu Ser Val Thr Glu Ile Thr Ala Ser Ser Phe Val
1               5                   10                  15

Val Ser Trp Val Ser Ala Ser Asp Thr Val Ser Gly Phe Arg Val Glu
            20                  25                  30

Tyr Glu Leu Ser Glu Glu Gly Asp Glu Pro Gln Tyr Leu Asp Leu Pro
            35                  40                  45

Ser Thr Ala Thr Ser Val Asn Ile Pro Asp Leu Leu Pro Gly Arg Lys
        50                  55                  60

Tyr Ile Val Asn Val Tyr Gln Ile Ser Glu Asp Gly Glu Gln Ser Leu
65                  70                  75                  80

Ile Leu Ser Thr Ser Gln Thr Thr Ala Pro Asp
                85                  90

<210> SEQ ID NO 8
<211> LENGTH: 92
<212> TYPE: PRT
<213> ORGANISM: Homo sapiens

<400> SEQUENCE: 8

Ala Pro Pro Asp Thr Thr Val Asp Gln Val Asp Asp Thr Ser Ile Val
1               5                   10                  15

Val Arg Trp Ser Arg Pro Gln Ala Pro Ile Thr Gly Tyr Arg Ile Val
            20                  25                  30

Tyr Ser Pro Ser Val Glu Gly Ser Ser Thr Glu Leu Asn Leu Pro Glu
            35                  40                  45

Thr Ala Asn Ser Val Thr Leu Ser Asp Leu Gln Pro Gly Val Gln Tyr
        50                  55                  60

Asn Ile Thr Ile Tyr Ala Val Glu Glu Asn Gln Glu Ser Thr Pro Val
65                  70                  75                  80

Val Ile Gln Gln Glu Thr Thr Gly Thr Pro Arg Ser
                85                  90

<210> SEQ ID NO 9
<211> LENGTH: 90
<212> TYPE: PRT
<213> ORGANISM: Homo sapiens

<400> SEQUENCE: 9

Ser Pro Arg Asp Leu Gln Phe Val Glu Val Thr Asp Val Lys Val Thr
1               5                   10                  15

Ile Met Trp Thr Pro Pro Glu Ser Ala Val Thr Gly Tyr Arg Val Asp
            20                  25                  30

Val Ile Pro Val Asn Leu Pro Gly Glu His Gly Gln Arg Leu Pro Ile
            35                  40                  45

Ser Arg Asn Thr Phe Ala Glu Val Thr Gly Leu Ser Pro Gly Val Thr
        50                  55                  60

Tyr Tyr Phe Lys Val Phe Ala Val Ser His Gly Arg Glu Ser Lys Pro
65                  70                  75                  80

Leu Thr Ala Gln Gln Thr Thr Lys Leu Asp
                85                  90
```

-continued

<210> SEQ ID NO 10
<211> LENGTH: 90
<212> TYPE: PRT
<213> ORGANISM: Homo sapiens

<400> SEQUENCE: 10

Ala Pro Thr Asn Leu Gln Phe Val Asn Glu Thr Asp Ser Thr Val Leu
1               5                   10                  15

Val Arg Trp Thr Pro Pro Arg Ala Gln Ile Thr Gly Tyr Arg Leu Thr
            20                  25                  30

Val Gly Leu Thr Arg Arg Gly Gln Pro Arg Gln Tyr Asn Val Gly Pro
        35                  40                  45

Ser Val Ser Lys Tyr Pro Leu Arg Asn Leu Gln Pro Ala Ser Glu Tyr
    50                  55                  60

Thr Val Ser Leu Val Ala Ile Lys Gly Asn Gln Glu Ser Pro Lys Ala
65                  70                  75                  80

Thr Gly Val Phe Thr Thr Leu Gln Pro Gly
                85                  90

<210> SEQ ID NO 11
<211> LENGTH: 87
<212> TYPE: PRT
<213> ORGANISM: Homo sapiens

<400> SEQUENCE: 11

Ser Ser Ile Pro Pro Tyr Asn Thr Glu Val Thr Glu Thr Thr Ile Val
1               5                   10                  15

Ile Thr Trp Thr Pro Ala Pro Arg Ile Gly Phe Lys Leu Gly Val Arg
            20                  25                  30

Pro Ser Gln Gly Gly Glu Ala Pro Arg Glu Val Thr Ser Asp Ser Gly
        35                  40                  45

Ser Ile Val Val Ser Gly Leu Thr Pro Gly Val Glu Tyr Val Tyr Thr
    50                  55                  60

Ile Gln Val Leu Arg Asp Gly Gln Glu Arg Asp Ala Pro Ile Val Asn
65                  70                  75                  80

Lys Val Val Thr Pro Leu Ser
                85

<210> SEQ ID NO 12
<211> LENGTH: 95
<212> TYPE: PRT
<213> ORGANISM: Homo sapiens

<400> SEQUENCE: 12

Pro Pro Thr Asn Leu His Leu Glu Ala Asn Pro Asp Thr Gly Val Leu
1               5                   10                  15

Thr Val Ser Trp Glu Arg Ser Thr Thr Pro Asp Ile Thr Gly Tyr Arg
            20                  25                  30

Ile Thr Thr Thr Pro Thr Asn Gly Gln Gln Gly Asn Ser Leu Glu Glu
        35                  40                  45

Val Val His Ala Asp Gln Ser Ser Cys Thr Phe Asp Asn Leu Ser Pro
    50                  55                  60

Gly Leu Glu Tyr Asn Val Ser Val Tyr Thr Val Lys Asp Asp Lys Glu
65                  70                  75                  80

Ser Val Pro Ile Ser Asp Thr Ile Ile Pro Glu Val Pro Gln Leu
                85                  90                  95

```
<210> SEQ ID NO 13
<211> LENGTH: 89
<212> TYPE: PRT
<213> ORGANISM: Homo sapiens

<400> SEQUENCE: 13

Thr Asp Leu Ser Phe Val Asp Ile Thr Asp Ser Ser Ile Gly Leu Arg
1               5                   10                  15

Trp Thr Pro Leu Asn Ser Ser Thr Ile Ile Gly Tyr Arg Ile Thr Val
            20                  25                  30

Val Ala Ala Gly Glu Gly Ile Pro Ile Phe Glu Asp Phe Val Asp Ser
        35                  40                  45

Ser Val Gly Tyr Tyr Thr Val Thr Gly Leu Glu Pro Gly Ile Asp Tyr
    50                  55                  60

Asp Ile Ser Val Ile Thr Leu Ile Asn Gly Gly Glu Ser Ala Pro Thr
65                  70                  75                  80

Thr Leu Thr Gln Gln Thr Ala Val Pro
                85

<210> SEQ ID NO 14
<211> LENGTH: 93
<212> TYPE: PRT
<213> ORGANISM: Homo sapiens

<400> SEQUENCE: 14

Pro Pro Thr Asp Leu Arg Phe Thr Asn Ile Gly Pro Asp Thr Met Arg
1               5                   10                  15

Val Thr Trp Ala Pro Pro Pro Ser Ile Asp Leu Thr Asn Phe Leu Val
            20                  25                  30

Arg Tyr Ser Pro Val Lys Asn Glu Glu Asp Val Ala Glu Leu Ser Ile
        35                  40                  45

Ser Pro Ser Asp Asn Ala Val Val Leu Thr Asn Leu Leu Pro Gly Thr
    50                  55                  60

Glu Tyr Val Val Ser Val Ser Ser Val Tyr Glu Gln His Glu Ser Thr
65                  70                  75                  80

Pro Leu Arg Gly Arg Gln Lys Thr Gly Leu Asp Ser Pro
                85                  90

<210> SEQ ID NO 15
<211> LENGTH: 88
<212> TYPE: PRT
<213> ORGANISM: Homo sapiens

<400> SEQUENCE: 15

Thr Gly Ile Asp Phe Ser Asp Ile Thr Ala Asn Ser Phe Thr Val His
1               5                   10                  15

Trp Ile Ala Pro Arg Ala Thr Ile Thr Gly Tyr Arg Ile Arg His His
            20                  25                  30

Pro Glu His Phe Ser Gly Arg Pro Arg Glu Asp Arg Val Pro His Ser
        35                  40                  45

Arg Asn Ser Ile Thr Leu Thr Asn Leu Thr Pro Gly Thr Glu Tyr Val
    50                  55                  60

Val Ser Ile Val Ala Leu Asn Gly Arg Glu Glu Ser Pro Leu Leu Ile
65                  70                  75                  80

Gly Gln Gln Ser Thr Val Ser Asp
                85
```

```
<210> SEQ ID NO 16
<211> LENGTH: 92
<212> TYPE: PRT
<213> ORGANISM: Homo sapiens

<400> SEQUENCE: 16

Lys Pro Ser Gln Met Gln Val Thr Asp Val Gln Asp Asn Ser Ile Ser
1               5                   10                  15

Val Lys Trp Leu Pro Ser Ser Ser Pro Val Thr Gly Tyr Arg Val Thr
            20                  25                  30

Thr Thr Pro Lys Asn Gly Pro Gly Pro Thr Lys Thr Lys Thr Ala Gly
        35                  40                  45

Pro Asp Gln Thr Glu Met Thr Ile Glu Gly Leu Gln Pro Thr Val Glu
    50                  55                  60

Tyr Val Val Ser Val Tyr Ala Gln Asn Pro Ser Gly Glu Ser Gln Pro
65                  70                  75                  80

Leu Val Gln Thr Ala Val Thr Asn Ile Asp Arg Pro
                85                  90

<210> SEQ ID NO 17
<211> LENGTH: 88
<212> TYPE: PRT
<213> ORGANISM: Homo sapiens

<400> SEQUENCE: 17

Lys Gly Leu Ala Phe Thr Asp Val Asp Val Asp Ser Ile Lys Ile Ala
1               5                   10                  15

Trp Glu Ser Pro Gln Gly Gln Val Ser Arg Tyr Arg Val Thr Tyr Ser
            20                  25                  30

Ser Pro Glu Asp Gly Ile His Glu Leu Phe Pro Ala Pro Asp Gly Glu
        35                  40                  45

Glu Asp Thr Ala Glu Leu Gln Gly Leu Arg Pro Gly Ser Glu Tyr Thr
    50                  55                  60

Val Ser Val Val Ala Leu His Asp Asp Met Glu Ser Gln Pro Leu Ile
65                  70                  75                  80

Gly Thr Gln Ser Thr Ala Ile Pro
                85

<210> SEQ ID NO 18
<211> LENGTH: 94
<212> TYPE: PRT
<213> ORGANISM: Homo sapiens

<400> SEQUENCE: 18

Ala Pro Thr Asp Leu Lys Phe Thr Gln Val Thr Pro Thr Ser Leu Ser
1               5                   10                  15

Ala Gln Trp Thr Pro Pro Asn Val Gln Leu Thr Gly Tyr Arg Val Arg
            20                  25                  30

Val Thr Pro Lys Glu Lys Thr Gly Pro Met Lys Glu Ile Asn Leu Ala
        35                  40                  45

Pro Asp Ser Ser Ser Val Val Val Ser Gly Leu Met Val Ala Thr Lys
    50                  55                  60

Tyr Glu Val Ser Val Tyr Ala Leu Lys Asp Thr Leu Thr Ser Arg Pro
65                  70                  75                  80

Ala Gln Gly Val Val Thr Thr Leu Glu Asn Val Ser Pro Pro
                85                  90

<210> SEQ ID NO 19
```

-continued

```
<211> LENGTH: 87
<212> TYPE: PRT
<213> ORGANISM: Homo sapiens

<400> SEQUENCE: 19

Arg Arg Ala Arg Val Thr Asp Ala Thr Glu Thr Thr Ile Thr Ile Ser
1               5                   10                  15

Trp Arg Thr Lys Thr Glu Thr Ile Thr Gly Phe Gln Val Asp Ala Val
            20                  25                  30

Pro Ala Asn Gly Gln Thr Pro Ile Gln Arg Thr Ile Lys Pro Asp Val
        35                  40                  45

Arg Ser Tyr Thr Ile Thr Gly Leu Gln Pro Gly Thr Asp Tyr Lys Ile
    50                  55                  60

Tyr Leu Tyr Thr Leu Asn Asp Asn Ala Arg Ser Ser Pro Val Val Ile
65                  70                  75                  80

Asp Ala Ser Thr Ala Ile Asp
                85

<210> SEQ ID NO 20
<211> LENGTH: 91
<212> TYPE: PRT
<213> ORGANISM: Homo sapiens

<400> SEQUENCE: 20

Ala Pro Ser Asn Leu Arg Phe Leu Ala Thr Thr Pro Asn Ser Leu Leu
1               5                   10                  15

Val Ser Trp Gln Pro Pro Arg Ala Arg Ile Thr Gly Tyr Ile Ile Lys
            20                  25                  30

Tyr Glu Lys Pro Gly Ser Pro Pro Arg Glu Val Val Pro Arg Pro Arg
        35                  40                  45

Pro Gly Val Thr Glu Ala Thr Ile Thr Gly Leu Glu Pro Gly Thr Glu
    50                  55                  60

Tyr Thr Ile Tyr Val Ile Ala Leu Lys Asn Asn Gln Lys Ser Glu Pro
65                  70                  75                  80

Leu Ile Gly Arg Lys Lys Thr Asp Glu Leu Pro
                85                  90

<210> SEQ ID NO 21
<211> LENGTH: 95
<212> TYPE: PRT
<213> ORGANISM: Homo sapiens

<400> SEQUENCE: 21

Pro Gly Leu Asn Pro Asn Ala Ser Thr Gly Gln Glu Ala Leu Ser Gln
1               5                   10                  15

Thr Thr Ile Ser Trp Ala Pro Phe Gln Asp Thr Ser Glu Tyr Ile Ile
            20                  25                  30

Ser Cys His Pro Val Gly Thr Asp Glu Glu Pro Leu Gln Phe Arg Val
        35                  40                  45

Pro Gly Thr Ser Thr Ser Ala Thr Leu Thr Gly Leu Thr Arg Gly Ala
    50                  55                  60

Thr Tyr Asn Val Ile Val Glu Ala Leu Lys Asp Gln Gln Arg His Lys
65                  70                  75                  80

Val Arg Glu Glu Val Val Thr Val Gly Asn Ser Val Asn Glu Gly
                85                  90                  95

<210> SEQ ID NO 22
<211> LENGTH: 91
```

<212> TYPE: PRT
<213> ORGANISM: Homo sapiens

<400> SEQUENCE: 22

```
Pro Pro Lys Asp Leu Val Val Thr Glu Val Thr Glu Glu Thr Val Asn
1               5                   10                  15

Leu Ala Trp Asp Asn Glu Met Arg Val Thr Glu Tyr Leu Val Val Tyr
            20                  25                  30

Thr Pro Thr His Glu Gly Gly Leu Glu Met Gln Phe Arg Val Pro Gly
        35                  40                  45

Asp Gln Thr Ser Thr Ile Ile Gln Glu Leu Glu Pro Gly Val Glu Tyr
    50                  55                  60

Phe Ile Arg Val Phe Ala Ile Leu Glu Asn Lys Lys Ser Ile Pro Val
65                  70                  75                  80

Ser Ala Arg Val Ala Thr Tyr Leu Pro Ala Pro
                85                  90
```

<210> SEQ ID NO 23
<211> LENGTH: 89
<212> TYPE: PRT
<213> ORGANISM: Homo sapiens

<400> SEQUENCE: 23

```
Glu Gly Leu Lys Phe Lys Ser Ile Lys Glu Thr Ser Val Glu Val Glu
1               5                   10                  15

Trp Asp Pro Leu Asp Ile Ala Phe Glu Thr Trp Glu Ile Ile Phe Arg
            20                  25                  30

Asn Met Asn Lys Glu Asp Glu Gly Glu Ile Thr Lys Ser Leu Arg Arg
        35                  40                  45

Pro Glu Thr Ser Tyr Arg Gln Thr Gly Leu Ala Pro Gly Gln Glu Tyr
    50                  55                  60

Glu Ile Ser Leu His Ile Val Lys Asn Asn Thr Arg Gly Pro Gly Leu
65                  70                  75                  80

Lys Arg Val Thr Thr Thr Arg Leu Asp
                85
```

<210> SEQ ID NO 24
<211> LENGTH: 90
<212> TYPE: PRT
<213> ORGANISM: Homo sapiens

<400> SEQUENCE: 24

```
Ala Pro Ser Gln Ile Glu Val Lys Asp Val Thr Asp Thr Thr Ala Leu
1               5                   10                  15

Ile Thr Trp Phe Lys Pro Leu Ala Glu Ile Asp Gly Ile Glu Leu Thr
            20                  25                  30

Tyr Gly Ile Lys Asp Val Pro Gly Asp Arg Thr Thr Ile Asp Leu Thr
        35                  40                  45

Glu Asp Glu Asn Gln Tyr Ser Ile Gly Asn Leu Lys Pro Asp Thr Glu
    50                  55                  60

Tyr Glu Val Ser Leu Ile Ser Arg Arg Gly Asp Met Ser Ser Asn Pro
65                  70                  75                  80

Ala Lys Glu Thr Phe Thr Thr Gly Leu Asp
                85                  90
```

<210> SEQ ID NO 25
<211> LENGTH: 96
<212> TYPE: PRT

<213> ORGANISM: Homo sapiens

<400> SEQUENCE: 25

Ala Pro Arg Asn Leu Arg Arg Val Ser Gln Thr Asp Asn Ser Ile Thr
1               5                   10                  15

Leu Glu Trp Arg Asn Gly Lys Ala Ala Ile Asp Ser Tyr Arg Ile Lys
                20                  25                  30

Tyr Ala Pro Ile Ser Gly Gly Asp His Ala Glu Val Asp Val Pro Lys
            35                  40                  45

Ser Gln Gln Ala Thr Thr Lys Thr Thr Leu Thr Gly Leu Arg Pro Gly
        50                  55                  60

Thr Glu Tyr Gly Ile Gly Val Ser Ala Val Lys Glu Asp Lys Glu Ser
65                  70                  75                  80

Asn Pro Ala Thr Ile Asn Ala Ala Thr Glu Leu Asp Thr Pro Lys Asp
                85                  90                  95

<210> SEQ ID NO 26
<211> LENGTH: 85
<212> TYPE: PRT
<213> ORGANISM: Homo sapiens

<400> SEQUENCE: 26

Leu Gln Val Ser Glu Thr Ala Glu Thr Ser Leu Thr Leu Leu Trp Lys
1               5                   10                  15

Thr Pro Leu Ala Lys Phe Asp Arg Tyr Arg Leu Asn Tyr Ser Leu Pro
                20                  25                  30

Thr Gly Gln Trp Val Gly Val Gln Leu Pro Arg Asn Thr Thr Ser Tyr
            35                  40                  45

Val Leu Arg Gly Leu Glu Pro Gly Gln Glu Tyr Asn Val Leu Leu Thr
        50                  55                  60

Ala Glu Lys Gly Arg His Lys Ser Lys Pro Ala Arg Val Lys Ala Ser
65                  70                  75                  80

Thr Glu Gln Ala Pro
                85

<210> SEQ ID NO 27
<211> LENGTH: 90
<212> TYPE: PRT
<213> ORGANISM: Homo sapiens

<400> SEQUENCE: 27

Glu Leu Glu Asn Leu Thr Val Thr Glu Val Gly Trp Asp Gly Leu Arg
1               5                   10                  15

Leu Asn Trp Thr Ala Ala Asp Gln Ala Tyr Glu His Phe Ile Ile Gln
                20                  25                  30

Val Gln Glu Ala Asn Lys Val Glu Ala Ala Arg Asn Leu Thr Val Pro
            35                  40                  45

Gly Ser Leu Arg Ala Val Asp Ile Pro Gly Leu Lys Ala Ala Thr Pro
        50                  55                  60

Tyr Thr Val Ser Ile Tyr Gly Val Ile Gln Gly Tyr Arg Thr Pro Val
65                  70                  75                  80

Leu Ser Ala Glu Ala Ser Thr Gly Glu Thr
                85                  90

<210> SEQ ID NO 28
<211> LENGTH: 90
<212> TYPE: PRT
<213> ORGANISM: Homo sapiens

<400> SEQUENCE: 28

Asn Leu Gly Glu Val Val Val Ala Glu Val Gly Trp Asp Ala Leu Lys
1               5                   10                  15

Leu Asn Trp Thr Ala Pro Glu Gly Ala Tyr Glu Tyr Phe Phe Ile Gln
            20                  25                  30

Val Gln Glu Ala Asp Thr Val Glu Ala Ala Gln Asn Leu Thr Val Pro
        35                  40                  45

Gly Gly Leu Arg Ser Thr Asp Leu Pro Gly Leu Lys Ala Ala Thr His
    50                  55                  60

Tyr Thr Ile Thr Ile Arg Gly Val Thr Gln Asp Phe Ser Thr Thr Pro
65                  70                  75                  80

Leu Ser Val Glu Val Leu Thr Glu Glu Val
                85                  90

<210> SEQ ID NO 29
<211> LENGTH: 93
<212> TYPE: PRT
<213> ORGANISM: Homo sapiens

<400> SEQUENCE: 29

Asp Met Gly Asn Leu Thr Val Thr Glu Val Ser Trp Asp Ala Leu Arg
1               5                   10                  15

Leu Asn Trp Thr Thr Pro Asp Gly Thr Tyr Asp Gln Phe Thr Ile Gln
            20                  25                  30

Val Gln Glu Ala Asp Gln Val Glu Glu Ala His Asn Leu Thr Val Pro
        35                  40                  45

Gly Ser Leu Arg Ser Met Glu Ile Pro Gly Leu Arg Ala Gly Thr Pro
    50                  55                  60

Tyr Thr Val Thr Leu His Gly Glu Val Arg Gly His Ser Thr Arg Pro
65                  70                  75                  80

Leu Ala Val Glu Val Val Thr Glu Asp Leu Pro Gln Leu
                85                  90

<210> SEQ ID NO 30
<211> LENGTH: 89
<212> TYPE: PRT
<213> ORGANISM: Homo sapiens

<400> SEQUENCE: 30

Gly Asp Leu Ala Val Ser Glu Val Gly Trp Asp Gly Leu Arg Leu Asn
1               5                   10                  15

Trp Thr Ala Ala Asp Asn Ala Tyr Glu His Phe Val Ile Gln Val Gln
            20                  25                  30

Glu Val Asn Lys Val Glu Ala Ala Gln Asn Leu Thr Leu Pro Gly Ser
        35                  40                  45

Leu Arg Ala Val Asp Ile Pro Gly Leu Glu Ala Ala Thr Pro Tyr Arg
    50                  55                  60

Val Ser Ile Tyr Gly Val Ile Arg Gly Tyr Arg Thr Pro Val Leu Ser
65                  70                  75                  80

Ala Glu Ala Ser Thr Ala Lys Glu Pro
                85

<210> SEQ ID NO 31
<211> LENGTH: 92
<212> TYPE: PRT
<213> ORGANISM: Homo sapiens -continued

```
<400> SEQUENCE: 31

Glu Ile Gly Asn Leu Asn Val Ser Asp Ile Thr Pro Glu Ser Phe Asn
1               5                   10                  15

Leu Ser Trp Met Ala Thr Asp Gly Ile Phe Glu Thr Phe Thr Ile Glu
            20                  25                  30

Ile Ile Asp Ser Asn Arg Leu Leu Glu Thr Val Glu Tyr Asn Ile Ser
        35                  40                  45

Gly Ala Glu Arg Thr Ala His Ile Ser Gly Leu Pro Pro Ser Thr Asp
    50                  55                  60

Phe Ile Val Tyr Leu Ser Gly Leu Ala Pro Ser Ile Arg Thr Lys Thr
65                  70                  75                  80

Ile Ser Ala Thr Ala Thr Thr Glu Ala Leu Pro Leu
                85                  90

<210> SEQ ID NO 32
<211> LENGTH: 89
<212> TYPE: PRT
<213> ORGANISM: Homo sapiens

<400> SEQUENCE: 32

Glu Asn Leu Thr Ile Ser Asp Ile Asn Pro Tyr Gly Phe Thr Val Ser
1               5                   10                  15

Trp Met Ala Ser Glu Asn Ala Phe Asp Ser Phe Leu Val Thr Val Val
            20                  25                  30

Asp Ser Gly Lys Leu Leu Asp Pro Gln Glu Phe Thr Leu Ser Gly Thr
        35                  40                  45

Gln Arg Lys Leu Glu Leu Arg Gly Leu Ile Thr Gly Ile Gly Tyr Glu
    50                  55                  60

Val Met Val Ser Gly Phe Thr Gln Gly His Gln Thr Lys Pro Leu Arg
65                  70                  75                  80

Ala Glu Ile Val Thr Glu Ala Glu Pro
                85

<210> SEQ ID NO 33
<211> LENGTH: 90
<212> TYPE: PRT
<213> ORGANISM: Homo sapiens

<400> SEQUENCE: 33

Glu Val Asp Asn Leu Leu Val Ser Asp Ala Thr Pro Asp Gly Phe Arg
1               5                   10                  15

Leu Ser Trp Thr Ala Asp Glu Gly Val Phe Asp Asn Phe Val Leu Lys
            20                  25                  30

Ile Arg Asp Thr Lys Lys Gln Ser Glu Pro Leu Glu Ile Thr Leu Leu
        35                  40                  45

Ala Pro Glu Arg Thr Arg Asp Ile Thr Gly Leu Arg Glu Ala Thr Glu
    50                  55                  60

Tyr Glu Ile Glu Leu Tyr Gly Ile Ser Lys Gly Arg Arg Ser Gln Thr
65                  70                  75                  80

Val Ser Ala Ile Ala Thr Thr Ala Met Gly
                85                  90

<210> SEQ ID NO 34
<211> LENGTH: 90
<212> TYPE: PRT
<213> ORGANISM: Homo sapiens

<400> SEQUENCE: 34
```

```
Ser Pro Lys Glu Val Ile Phe Ser Asp Ile Thr Glu Asn Ser Ala Thr
1               5                   10                  15

Val Ser Trp Arg Ala Pro Thr Ala Gln Val Glu Ser Phe Arg Ile Thr
            20                  25                  30

Tyr Val Pro Ile Thr Gly Gly Thr Pro Ser Met Val Thr Val Asp Gly
        35                  40                  45

Thr Lys Thr Gln Thr Arg Leu Val Lys Leu Ile Pro Gly Val Glu Tyr
    50                  55                  60

Leu Val Ser Ile Ile Ala Met Lys Gly Phe Glu Glu Ser Glu Pro Val
65                  70                  75                  80

Ser Gly Ser Phe Thr Thr Ala Leu Asp Gly
                85                  90
```

<210> SEQ ID NO 35
<211> LENGTH: 87
<212> TYPE: PRT
<213> ORGANISM: Homo sapiens

<400> SEQUENCE: 35

```
Pro Ser Gly Leu Val Thr Ala Asn Ile Thr Asp Ser Glu Ala Leu Ala
1               5                   10                  15

Arg Trp Gln Pro Ala Ile Ala Thr Val Asp Ser Tyr Val Ile Ser Tyr
            20                  25                  30

Thr Gly Glu Lys Val Pro Glu Ile Thr Arg Thr Val Ser Gly Asn Thr
        35                  40                  45

Val Glu Tyr Ala Leu Thr Asp Leu Glu Pro Ala Thr Glu Tyr Thr Leu
    50                  55                  60

Arg Ile Phe Ala Glu Lys Gly Pro Gln Lys Ser Ser Thr Ile Thr Ala
65                  70                  75                  80

Lys Phe Thr Thr Asp Leu Asp
                85
```

<210> SEQ ID NO 36
<211> LENGTH: 89
<212> TYPE: PRT
<213> ORGANISM: Homo sapiens

<400> SEQUENCE: 36

```
Ser Pro Arg Asp Leu Thr Ala Thr Glu Val Gln Ser Glu Thr Ala Leu
1               5                   10                  15

Leu Thr Trp Arg Pro Pro Arg Ala Ser Val Thr Gly Tyr Leu Leu Val
            20                  25                  30

Tyr Glu Ser Val Asp Gly Thr Val Lys Glu Val Ile Val Gly Pro Asp
        35                  40                  45

Thr Thr Ser Tyr Ser Leu Ala Asp Leu Ser Pro Ser Thr His Tyr Thr
    50                  55                  60

Ala Lys Ile Gln Ala Leu Asn Gly Pro Leu Arg Ser Asn Met Ile Gln
65                  70                  75                  80

Thr Ile Phe Thr Thr Ile Gly Leu Leu
                85
```

<210> SEQ ID NO 37
<211> LENGTH: 94
<212> TYPE: PRT
<213> ORGANISM: Homo sapiens

<400> SEQUENCE: 37

-continued

```
Val Pro Arg Asp Leu Glu Val Val Ala Ala Thr Pro Thr Ser Leu Leu
1             5             10             15

Ile Ser Trp Asp Ala Pro Ala Val Thr Val Arg Tyr Tyr Arg Ile Thr
             20             25             30

Tyr Gly Glu Thr Gly Gly Asn Ser Pro Val Gln Glu Phe Thr Val Pro
         35             40             45

Gly Ser Lys Ser Thr Ala Thr Ile Ser Gly Leu Lys Pro Gly Val Asp
     50             55             60

Tyr Thr Ile Thr Val Tyr Ala Val Thr Gly Arg Gly Asp Ser Pro Ala
65             70             75             80

Ser Ser Lys Pro Ile Ser Ile Asn Tyr Arg Thr Glu Ile Asp
             85             90
```